(12) United States Patent
Shamloo et al.

(10) Patent No.: US 9,849,134 B2
(45) Date of Patent: Dec. 26, 2017

(54) METHOD OF IMPROVING COGNITION AND SOCIAL BEHAVIOR IN HUMANS HAVING DEFICITS THEREIN DUE TO NEURODEGENERATIVE DISORDERS AND COMPOUNDS AND COMPOSITIONS THEREFOR

(71) Applicant: The Board of Trustees of the Leland Stanford Junior University, Stanford, CA (US)

(72) Inventors: Mehrdad Shamloo, Stanford, CA (US); Bitna Yi, San Mateo, CA (US); Pooneh Memar Ardestani, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/625,170

(22) Filed: Feb. 18, 2015

(65) Prior Publication Data

US 2016/0184315 A1   Jun. 30, 2016

Related U.S. Application Data

(60) Provisional application No. 61/940,980, filed on Feb. 18, 2014.

(51) Int. Cl.
*C07D 265/32* (2006.01)
*A61K 31/17* (2006.01)
*A61K 31/5375* (2006.01)
*A61K 9/00* (2006.01)
*A61K 9/08* (2006.01)
*A61K 47/48* (2006.01)
*G01N 33/50* (2006.01)

(52) U.S. Cl.
CPC ........ *A61K 31/5375* (2013.01); *A61K 9/0019* (2013.01); *A61K 9/08* (2013.01); *A61K 47/48023* (2013.01); *G01N 33/502* (2013.01)

(58) Field of Classification Search
CPC ............................. C07D 265/32; A61K 31/17

USPC ............................................. 514/230.8, 595
See application file for complete search history.

(56) References Cited

U.S. PATENT DOCUMENTS

| 2003/0216413 | A1 | 11/2003 | Root-Bernstein et al. |
| 2004/0224368 | A1 | 11/2004 | Marks |
| 2005/0118286 | A1 | 6/2005 | Suffin et al. |
| 2010/0130566 | A1 | 5/2010 | Purpura et al. |
| 2010/0298431 | A1 | 11/2010 | Salehi et al. |
| 2013/0053350 | A1 | 2/2013 | Colca et al. |

FOREIGN PATENT DOCUMENTS

| EP | 0227339 A2 | 7/1987 |
| EP | 0307115 A1 | 3/1989 |
| WO | WO 98/09523 | 3/1998 |

OTHER PUBLICATIONS

Dierssen, et al. Alterations of central noradrenergic transmission in Ts65Dn mouse, a model for Down Syndrome.Brain Research, 1997, vol. 749, pp. 238-244.
Murchison, et al. A distinct role for epinephrine in memory retrieval. Cell, 2004, vol. 117, pp. 131-143.
Salehi, et al. Restoration of norepinephrine-modulated contextual memory in a mouse model of Down syndrome.Science Translational Medicine, 2009, vol. 1 Issue 7, 7ra17.
Mehlsen, et al. Xamoterol, a new selective beta-1 adrenoreceptor partial agonist, in the treatment of postural hypotension. Acta Med. Scand. 1986. 219:173-7.
Michel, et al. The beta-1 adrenoreceptor agonist xamoterol protects dopaminergic neurons from apoptosis.Society for Neuroscience Abstracts, 1999, vol. 25, No. 1-2, pp. 2018, Oct. 23-28, 1999.
Kemppainen, et al. Hippocampal dopamine D2 receptors correlate with memory functions in Alzheimer's disease. European Journal of Neuroscience, vol. 18, pp. 149-154 2003.

*Primary Examiner* — Raymond Henley, III
(74) *Attorney, Agent, or Firm* — Glenn J. Foulds; Bozicevic, Field & Francis LLP

(57) ABSTRACT

A $\beta_1$-ADR agonist prodrug compound, which is hydrolysable in vivo to release a β1-ADR agonist compound, and which prodrug compound contains a group which imparts greater lipophilicity and CNS bioavailability to the prodrug compound relative to the β1-ADR agonist compound.

36 Claims, 34 Drawing Sheets

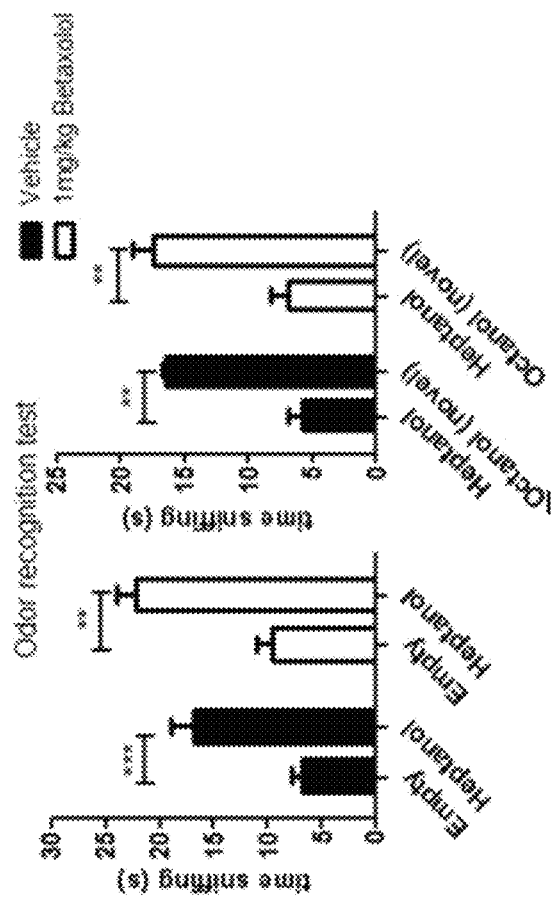
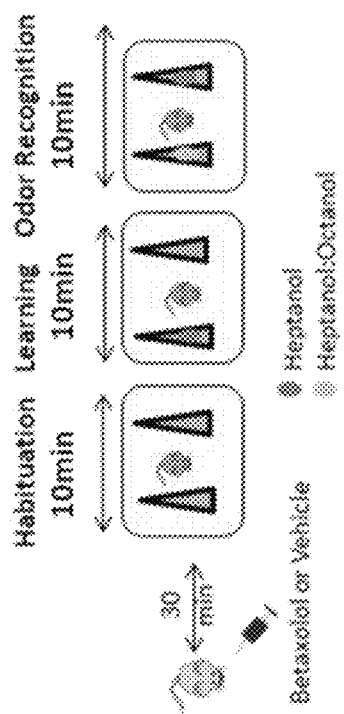
FIG. 2C
FIG. 2D

Overview of the therapeutic strategy.

contextual memory is impaired in C57Bl/6 mice treated with a single dose of In 1mg/kg of the β1-ADR antagonist betaxolol Upregulation of β1-ADR expression in the medial amygdala of Thy1-APP$^{Lond/Swe+}$ (Tg) mice is detected by DAB-staining. (*p<0.05; Non-Tg: non-transgenic).

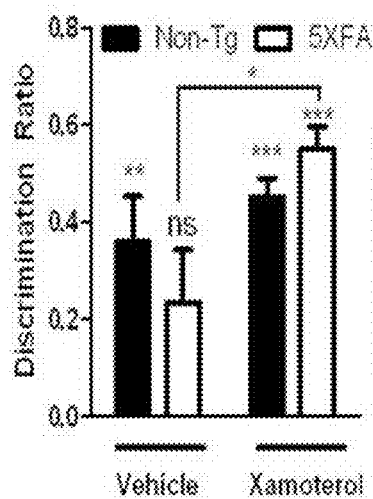 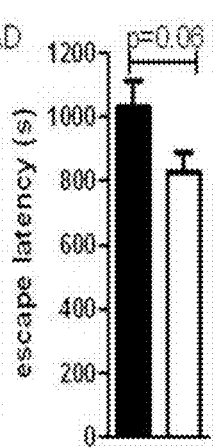 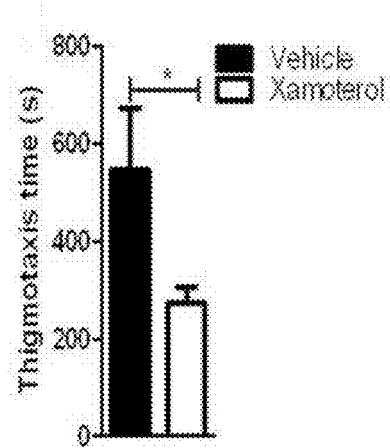
FIG. 15A  FIG. 15B  FIG. 15C
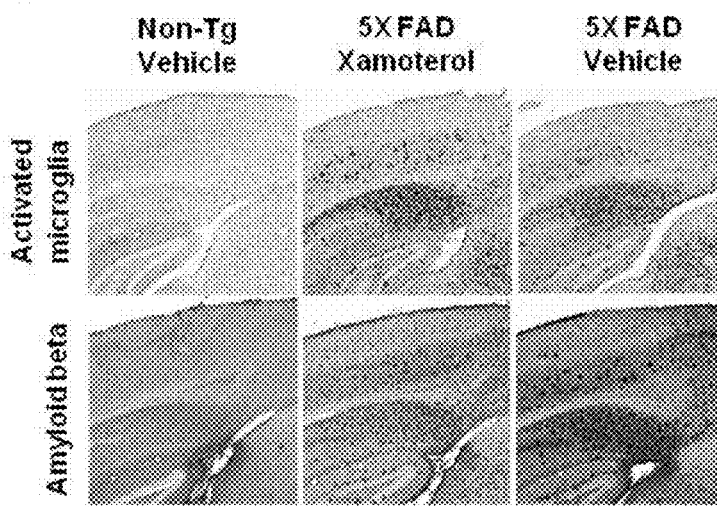
FIG. 15D

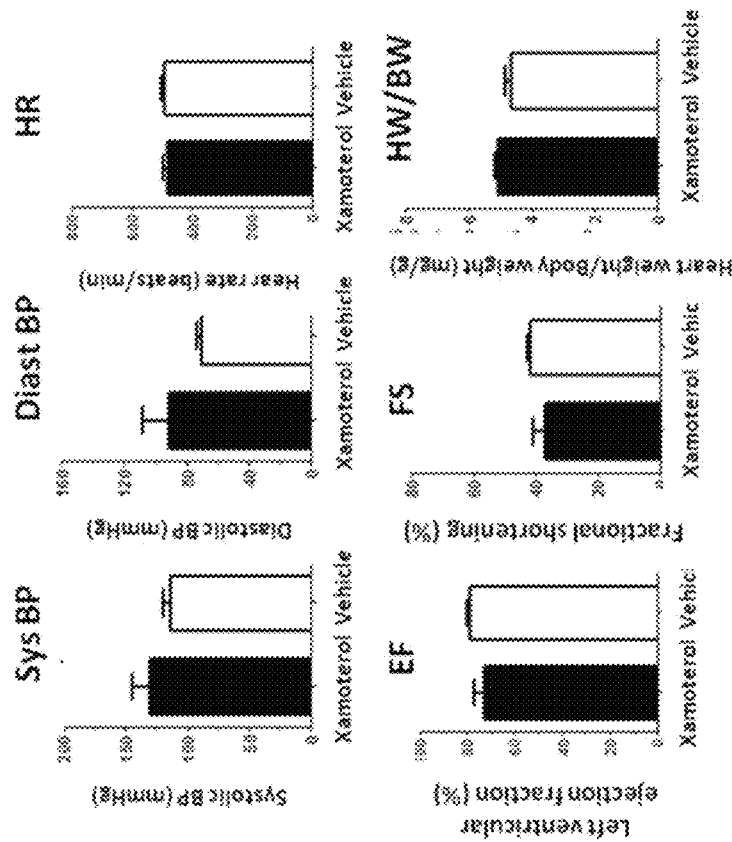
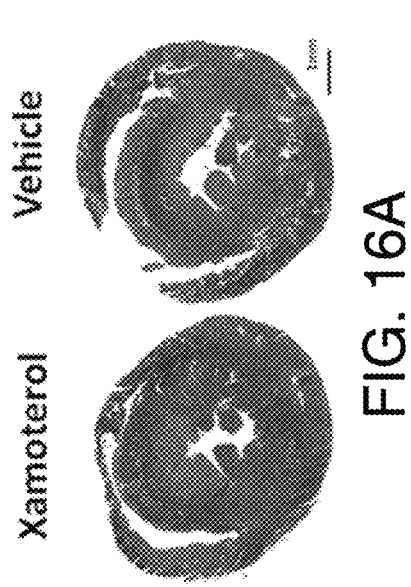
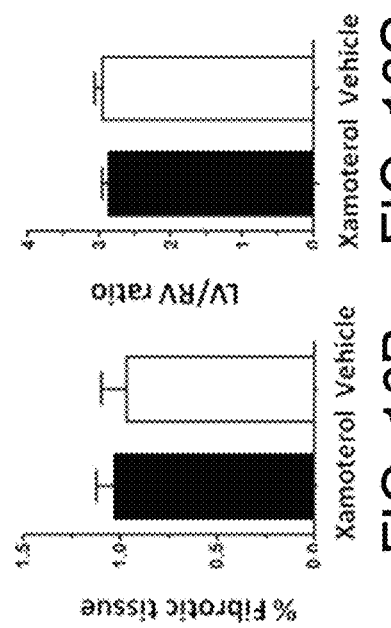
FIG. 16A  FIG. 16B  FIG. 16C  FIG. 16D

The structure of xamoterol and locations for structural modifications with the addition of –R₁ and –R₂ groups Examples of potential lipophilic prodrugs (1-4) of Xamoterol and their ClogP values.

| | R₁ | R₂ | ClogP |
|---|---|---|---|
| 1 | propanoate ester | propanoate ester | 0.89 |
| 2 | isopropyl carbamate | isobutyl carbamate | 1.28 |
| 3 | isobutyrate ester | isobutyrate ester | 2.03 |
| 4 | benzoate ester | benzoate ester | 3.38 |

FIG. 18

Specific exemplary prodrugs of xamoterol in accordance with the present invention.

METHOD OF IMPROVING COGNITION AND SOCIAL BEHAVIOR IN HUMANS HAVING DEFICITS THEREIN DUE TO NEURODEGENERATIVE DISORDERS AND COMPOUNDS AND COMPOSITIONS THEREFOR

STATEMENT REGARDING FEDERALLY SPONSORED RESEARCH OR DEVELOPMENT

This invention was made with Government support under contracts NS069375 and TR001085 awarded by the National Institutes of Health. The Government has certain rights in the invention.

BACKGROUND OF THE INVENTION

Neurodegenerative disorders, conditions and diseases, such as Alzheimer's disease (AD), are an ever-increasing concern in modern society. AD alone affects at least 24 million people world-wide and its prevalence is expected to increase exponentially due to both an aging population and higher rates of diagnosis. Currently available AD medications approved by the FDA, such as cholinesterase inhibitors and memantine, only provide symptomatic relief. AD remains incurable at present. Without a doubt, the lack of an effective therapy for AD might be attributable to the complex array of factors involved in the development and progression of the disease. For example, AD development and progression is characterized by loss of neurons and synapses, alterations of various neurotransmitter systems, accumulation of amyloid plaques and neurofibrillary tangles, and chronic inflammation evidenced by the presence of activated microglia and reactive astrocytes surrounding the amyloid plaques observed at various stages of AD. This array of symptoms underscores the complex difficulties involved in developing an effective therapy for humans having AD, and indicates that the simultaneous modulation of different key target points of AD pathology might represent the most comprehensive therapy therefor.

The inability to recognize faces (social recognition) is a defined endophenotype of several neurological disorders including Alzheimer's disease (AD). Yet, the underlying causes of this symptom remain elusive. Several studies have highlighted the role of oxytocin and vasopressin in social recognition and have shown that low levels of oxytocin could be responsible for deficit in face recognition in autistic patients. However, in AD patients, postmortem studies failed to show difference in central vasopressin and oxytocin concentration except in the hippocampus where it seems higher than levels in normal patients. This indicates that variations in oxytocin levels do not underlie the deficit in social recognition in AD and points to our incomplete understanding of the neural circuitries responsible for social recognition. Additionally, the long term effects of oxytocin use by humans is unknown and may well prove to be harmful.

A well-defined pathological hallmark of AD is the degeneration of the neurons in the locus coeruleus, the main source of noradrenaline (NA) in the brain. This degeneration is associated with a subsequent reduction of NA and reduced activation of the adrenergic receptors. Adrenergic receptors mediate distinctive actions of NA via various intracellular signaling pathways and play important roles in learning and memory processes. Recently, the contribution of the β-adrenergic system specifically the $\beta_1$-adrenergic receptor ($\beta_1$-ADR) in cognitive functions has received interest. For instance, NA action on β-ADR modulates inhibitory synaptic function. Other studies have shown that the $\beta_1$-selective antagonist betaxolol produces spatial navigation retrieval deficit in wild-type mice and rats, while the retrieval deficit observed in mice with NA deficiency can be rescued by the $\beta_1$-partial agonist xamoterol. These results indicate that the NAergic neurotransmission mediated by the $\beta_1$-ADR may be critically involved in the cognitive deficits observed in neurological disorders characterized by NAergic degeneration.

Unfortunately, the currently incomplete understanding of the neural and, ultimately, molecular causes underlying Alzheimer's disease has contributed to a lack of effective therapies therefor. An effective therapy for improving both cognition and social recognition/social memory would also be a useful therapy for Autism. Similarly, as the present invention provides a means for improving both cognition and social behavior, it also affords a method of treating both ADD and ADHD.

SUMMARY OF THE INVENTION

The present invention provides a method of improving cognition and social recognition in humans having Alzheimer's disease, Down syndrome, ADD, ADHD or Autism, which entails administering at least one compound, which is a β1-adrenergic receptor agonist or prodrug-compound thereof, or both, or a pharmaceutically-acceptable salt of either or both in an amount sufficient to improve said cognition and social recognition.

The present invention also provides numerous prodrug β1-adrenergic receptor agonist compounds which release β1-adrenergic receptor agonists upon hydrolysis in vivo, and compositions containing the same. The β1-ADR agonist prodrugs have an improved lipophilicity and CNS bioavailability relative to the β1-ADR agonist compound.

The present invention further provides R- and S-enantiomeric compounds of β1-ADR agonist compounds having a chiral center, which may be used separately instead of the racemic mixture of such compounds, as well as methods for making these enantiomeric compounds.

The present invention also provides methods for improving social memory and other cognitive traits in humans exhibiting Alzheimer's disease, Down syndrome, ADD, ADHD and/or Autism.

BRIEF DESCRIPTION OF THE DRAWINGS

FIG. 2(A)-(F): Activation of the $\beta_1$-ADR is necessary for social recognition. In the left, representative diagram of the experimental design followed to assess social recognition. Blockage of the $\beta_1$-ADR with various doses of betaxolol ranging from 0.01 to 1 mg/kg (n=8 per group) did not affect social learning but impaired social recognition. (A) All mice injected betaxolol or vehicle preferred a cup containing an unfamiliar C57B1/6 mouse over an empty cup (* p<0.0001 by paired t-test). (B) However, mice injected with 0.1 or 1 mg/kg of betaxolol did not show a preference for a novel C56B1/6 intruder mouse over a familiar one (ns by paired t-test), indicative of impaired social recognition, while mice injected with vehicle or 0.01 mg/kg of betaxolol showed this preference ( p=0.003 and 0.008 by paired t-test, respectively); Betaxolol did not impair non-social order recognition; (C) In a test of non-social odor recognition, betaxolol did not affect the preference of mice for a tube containing a heptanol solution over an empty tube (vehicle n=7 * p=0.0004; betaxolol n=7  p=0.0016 by paired t-test) and (D) did not affect the ability of mice to discriminate between a familiar odor (heptanol) versus a new but similar odor (a solution of heptanol:octanol) (vehicle  p=0.019; betaxolol  p=0.0015 by paired t-test). (E) Systemic injection of xamoterol (3 mg/kg) prior to social recognition testing did not affect the preference of WT (n=10) and APP (n=10) mice for an unfamiliar intruder over an empty cup *** p<0.0001 by paired t-test); but (F) rescued the social recognition deficit observed previously in APP mice (see FIG. 1B); similarly to their WT control littermates injected with xamoterol (n=10), xamoterol injected APP mice (n=10) showed preference for a novel intruder over a familiar one (WT; * p=0.0198; APP: ***p=0.0001, by paired t-test.

Figure 7A:
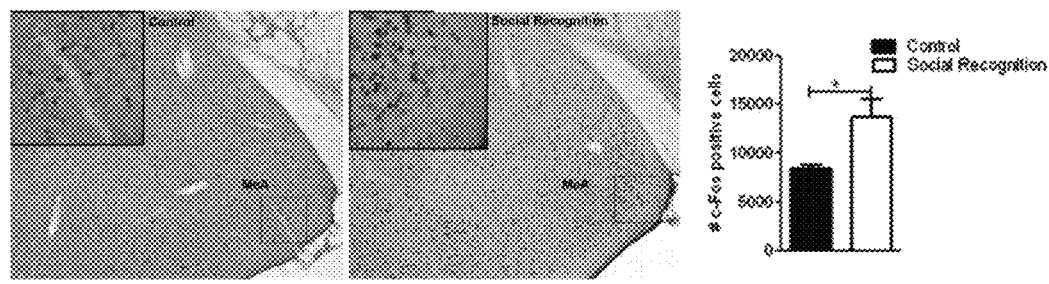
Figure 7B:
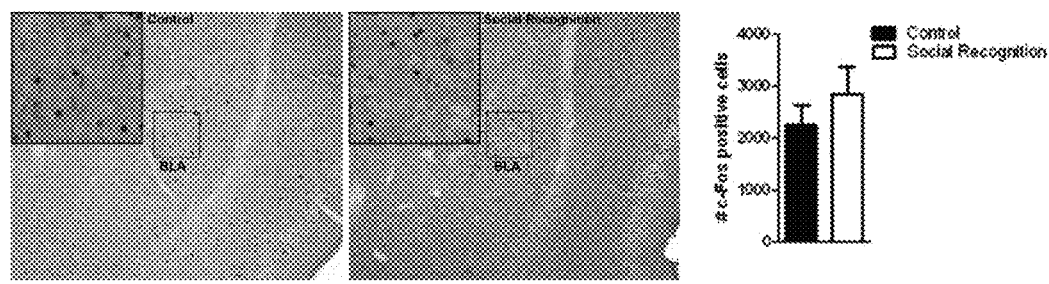
Figure 7C:
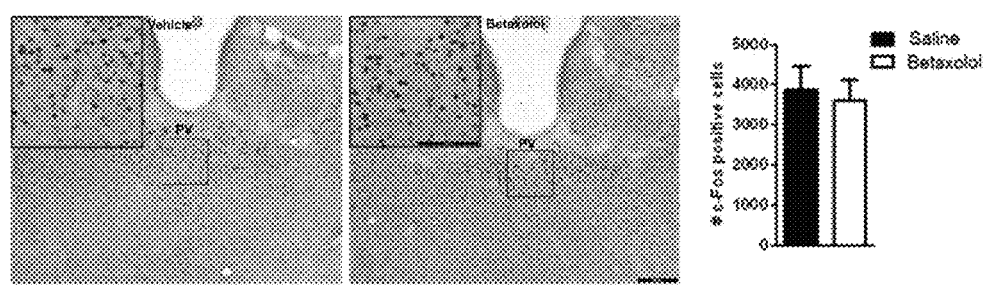

FIG. 7(A)-(C): (A) c-Fos expression is induced in the MeA 90 minutes after social recognition. Quantification of c-Fos positive cells was performed using a non-biased stereological method. In control mice (n=4) and mice exposed to a social recognition task (n=$) (* p–0.0303 by t-test). (B) c-Fos expression was not induced in the basolateral amygdala (BLA) after social recognition. Quantification of c-Fos positive cells was performed using a non-biased stereological method in control mice (n=4) and mice exposed to a social recognition task (n=4) (p=0.4857 by Mann-Whitney test). (C) Injection of betaxolol prior to testing in a social recognition task did not affect the number of c-Fos positive cells in the thalamus (PV), brain region not involved in social memory and poor in $\beta_1$-ADR (vehicle-injected mic n=4; betaxolol-injected mice n=4; p=0.8571 by Mann-Whitney test). Data are presented as mean±SEM. Scale bars, 100 μm (magnified box) and 200 μm.

Figure 8:
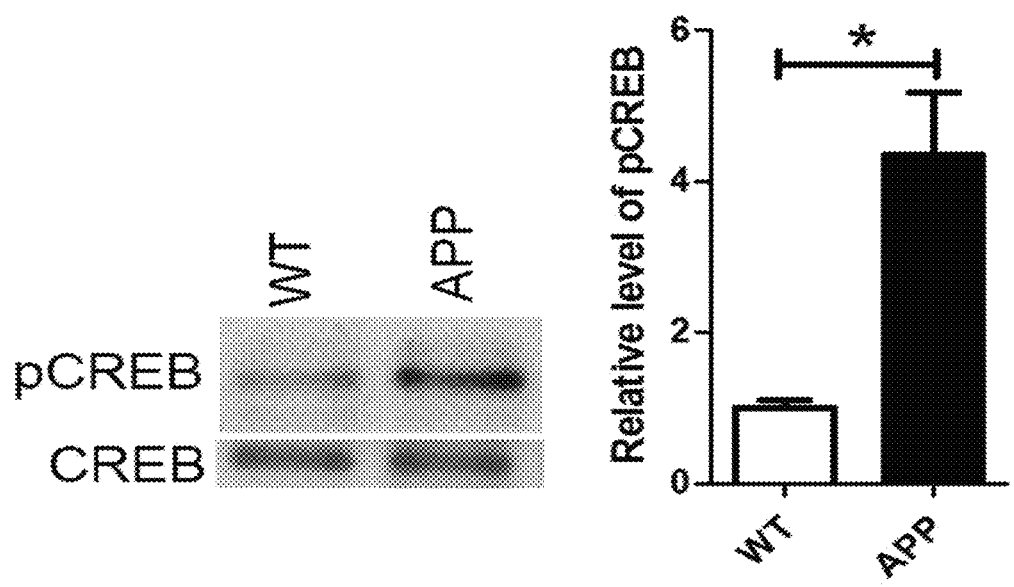

FIG. 8: Western blot analysis of pCREB performed on whole tissue homogenates from medial amygdala of control mice and APP mice (n=4 per group), pCREB level was significantly higher in APP mice (*, p=0.0286 by Mann-Whitney test). The relative optical density is normalized to CREB. Data are presented as mean±SEM.

Figure 9:
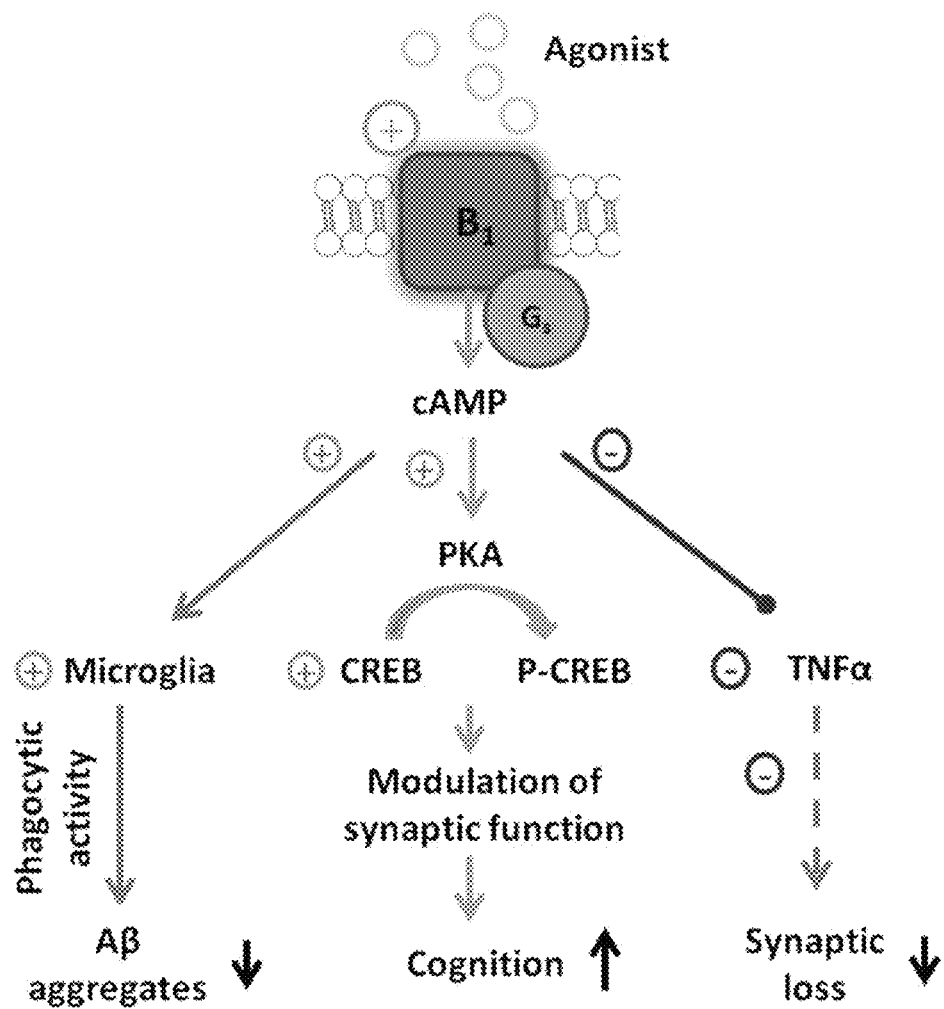

FIG. 9: illustrates a working model of β1-ADR agonist compounds (or their prodrugs or derivatives) as therapeutic agents for AD, for example. Activation of β1-ADR can provide unique disease modifying effects in addition to restoration of cognitive function.

Figure 10:
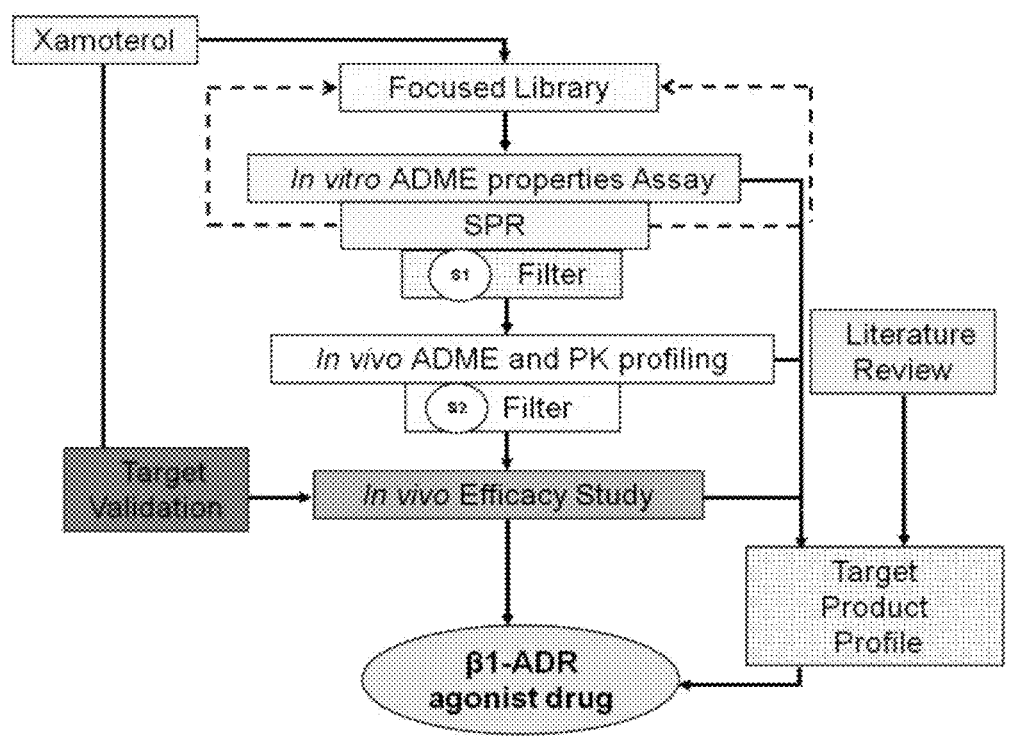

FIG. 10: illustrates a schematic of the methodology used to determine effectiveness of individual compounds and prodrugs thereof as therapeutic compounds for the treatment of AD, DS, ADD, ADHD and Autism.

Figures 11A, 11B:
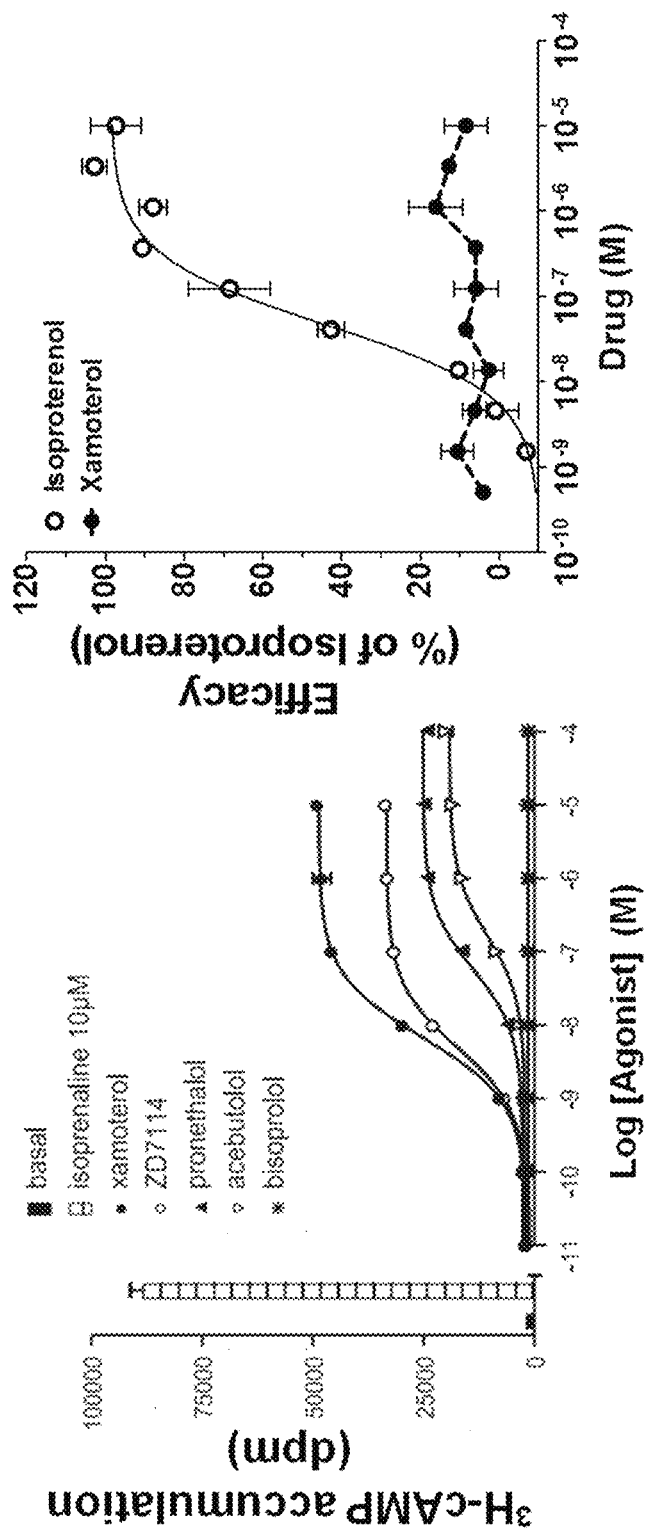

FIG. 11(A)-(B): illustrates (A) the pharmacology of xamoterol, whereby xamoterol does stimulate cAMP signaling as a β1-ADR agonist (A), while having no effect on the β-arrestin pathway (B). In contrast, isoprenaline activates both cAMP and β-arrestin pathways. Xamoterol is a partial agonist for the β1-ADR that stimulates cAMP signaling to elicit about 60% of maximal response to the full agonist isoprenaline. On the other hand, xamoterol has no effect on the β-arrestin pathway as opposed to the unbiased isoprenaline, which activates both cAMP and β-arrestin pathways.

Figure 12:
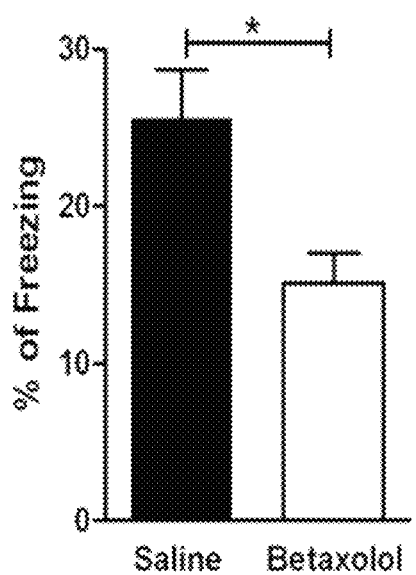

FIG. 12: C57Bl/6 mice treated with a single dose (1 mg/kg) of the β1-ADR antagonist betaxolol which results in impairment of contextual memory.

Figure 13A:
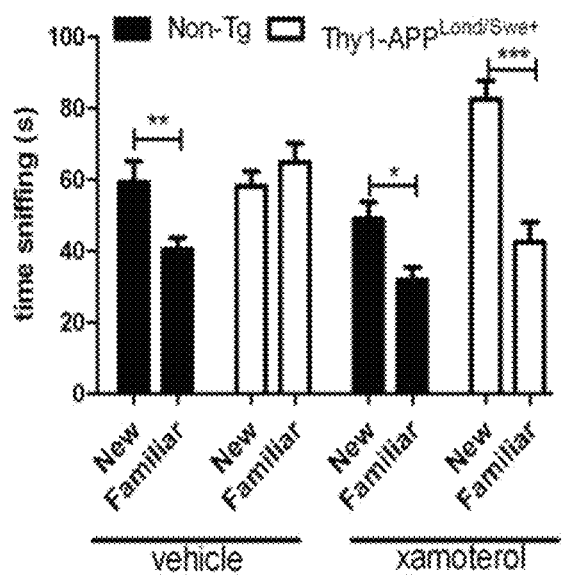
Figure 13B:
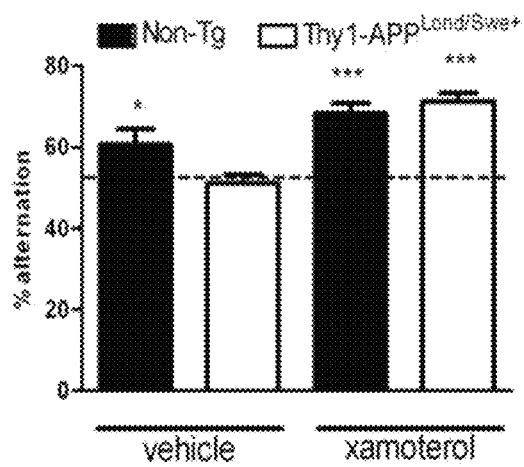

FIG. 13(A)-(B): illustrates that deficits in social memory (A) and working memory (B) observed in Thy1-APP$^{Lond/Swe+}$ mice are rescued by acute subcutaneous dosing of xamoterol. (*p<0.05; p<0.01; *p<0.001. Non-tg: non-transgenic).

Figure 14:
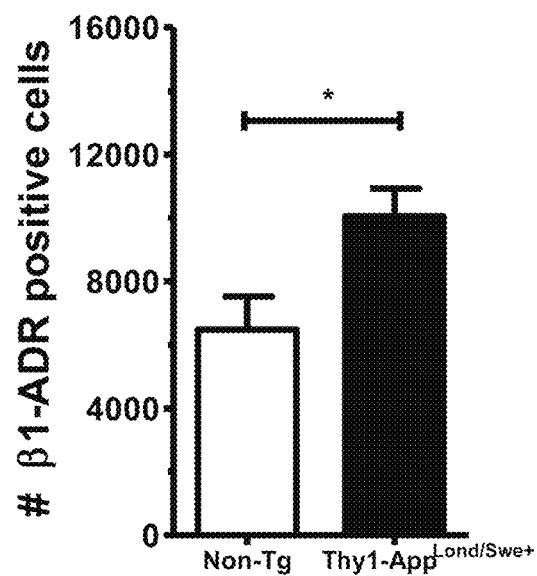

FIG. 14: illustrates upregulation of β1-ADR expression in the medial amygdale of Thy1-APP$^{Lond/Swe+}$ (Tg) mice is detected by DAB-staining (*p<0.05; Non-Tg=non-transgenic).

FIG. 15(A)-(D): illustrates the effect of chronic dosing with xamoterol in SXFAD mice: (A) the deficit in declarative memory (discrimination ratio not significantly above chance level) is rescued by xamoterol treatment. (B and C) Performance in the Morris-Water Maze (escape latency—B and time in thigmotaxis—C) are improved with the treatment. Ns: non-significantly above chance level; *p=0.05; p<0.001; *p<0.001. Chronic dosing with xamoterol increased activated microglia and Aβ plaque clearance. (D) DAB staining on 50 μm coronal sections stained with: upper row, anti-Iba1 antibody (against activated microglia); lower row, 6E10 anti-amyloid AB antibody.

FIG. 16(A)-(D): illustrates chronic treatment with xamoterol (3 mg/kg, s.c., 3 months) did not produce changes in myocardial structure as measured by Masson's trichrome staining of the sectioned heart (A). Wild type mice treated with xamoterol/vehicle for 3 months did not show significant difference in myocardial fibrosis (B) and the left ventricular to right ventricular (LV/RV) ratio (C). Wild type mice treated with xamoterol/vehicle for 3 months did not show significant difference in cardiovascular functions (D). Systemic blood pressure: sys BP; diastolic blood pressure: diast BP; heart rate; ejection fraction: EF; fractional shortening: FS; heart weight/body weight: HW/BW (n=3).

Figure 17:
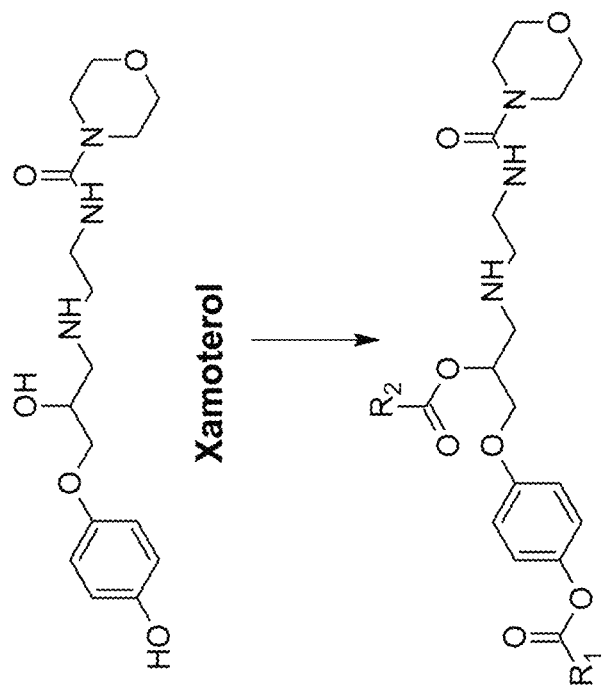

FIG. 17: illustrates the structure of xamoterol and some locations for structural modifications with the addition of groups designated as $R_1$ and $R_2$. Examples of $R_1$ and $R_2$ are acyl, carbamyl and oxoazolidyl. Additionally, in the xamoterol molecule, hydrolysable prodrugs may be formed by derivatizing —NH— groups. For example, the —NH— groups may be acylated as described in U.S. Pat. No. 8,865,920, which is incorporated herein in the entirety. In the present invention, the groups used to form the structural modifications are used to form prodrugs of xamoterol and other β1-ADR agonists, which render the prodrug to be more lipophilic with greater CNS bioavailability than the β1-ADR agonist.

FIG. 18: illustrates examples of lipophilic prodrugs (1-4) of xamoterol and their C log P values. In this figure, both $R_1$ and $R_2$ are used, but prodrugs having either $R_1$ or $R_2$ alone are contemplated.

Figure 19:
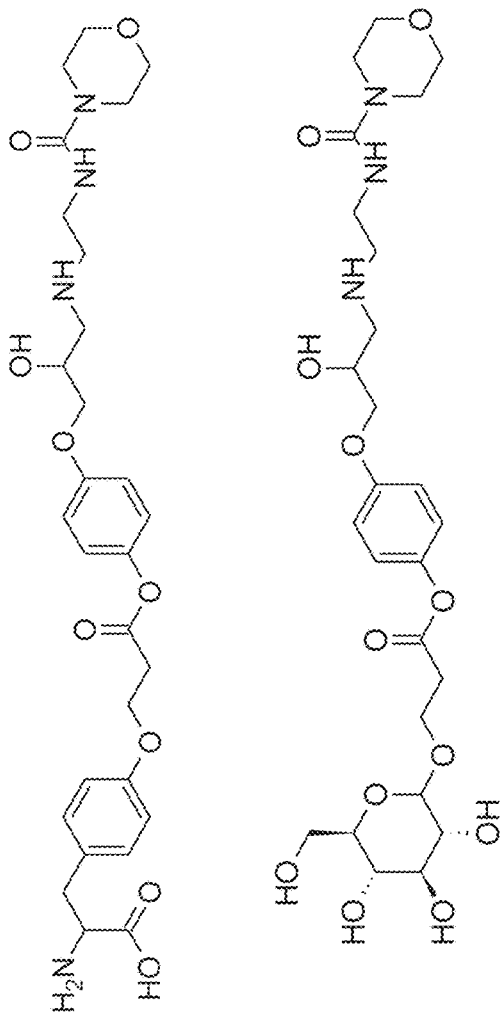

FIG. 19: illustrates specific exemplary prodrugs of xamoterol in accordance with the present invention where only $R_1$ is used. $R_2$ is not used in these two examples.

Figure 20:
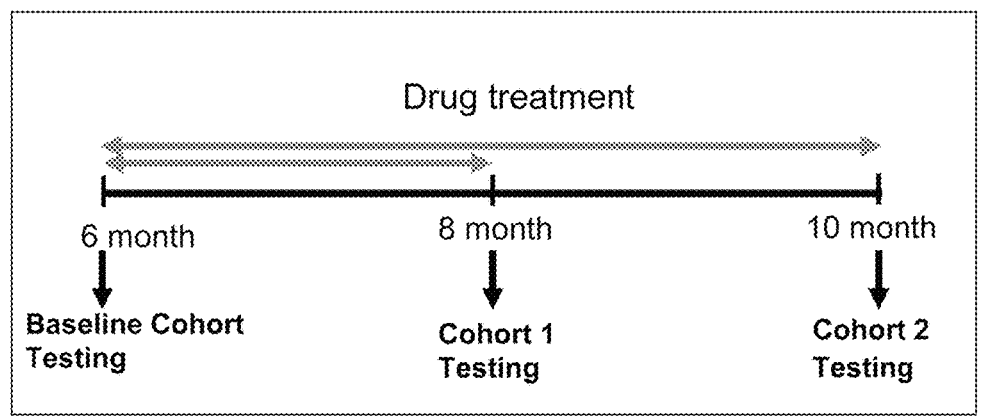

FIG. 20: illustrates a scheme for the testing of prodrugs in a pre-clinical animal model of AD.

Figure 21A:
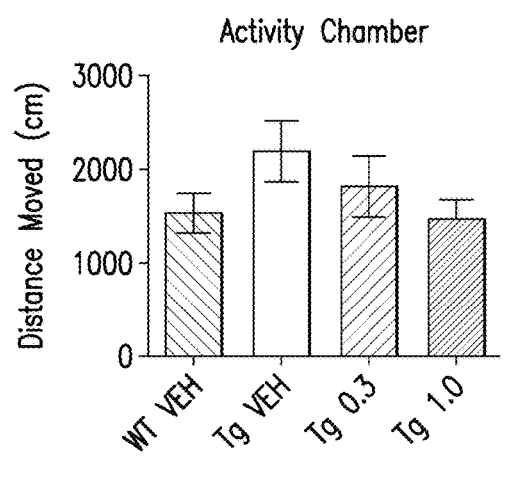
Figure 21B:
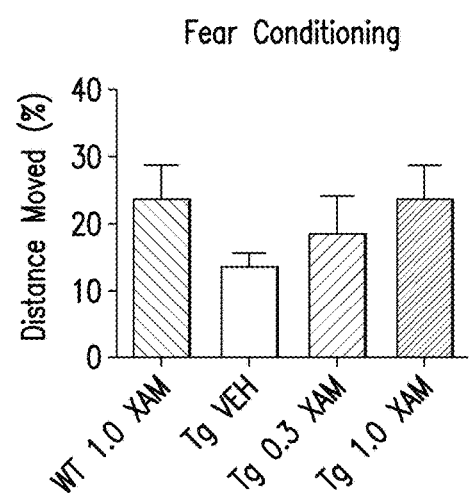

FIG. 21(A)-(B): illustrates the behavioral effects of xamoterol in the transgenic mouse model of Alzheimer's disease, Thy1-hAPP$^{Lond/Swe+}$ line transgenic mice. (A) shows that chronic treatment with xamoterol produces dose-dependent reversal of hyperactivity phenotype in these transgenic mice. (B) shows that chronic treatment with xamoterol produces dose-dependent improvement in cognitive functioning as determined by fear conditioning test. This demonstrates the potential usefulness of the prodrugs in the treatment of ADD and ADHD. Xamoterol produces dose-dependent effects on behavioral phenotype of the transgenic mouse model of Alzheimer's disease, which suggests β1-ADR agonists may offer symptomatic relief for Alzheimer's patients. Chronic treatment with xamoterol (0.3 mg/kg and 1 mg/kg, subcutaneous) produces dose-dependent reversal of hyperactivity phenotype shown in Thy1-hAPP$^{Lond/Swe+}$ line transgenic mice (n=9-10). Locomotor activity of mice was determined by activity chamber test after 1 month of xamoterol treatment (A). Chronic treatment with xamoterol (0.3 mg/kg and 1 mg/kg, subcutaneous) produces dose-dependent improvement in Thy1-hAPP$^{Lond/Swe+}$ line transgenic mice as well as in wild-type littermate (n=9-10). The cognitive function was determined by fear conditioning test after 2.5 months of xamoterol treatment (B).

Figure 22A:
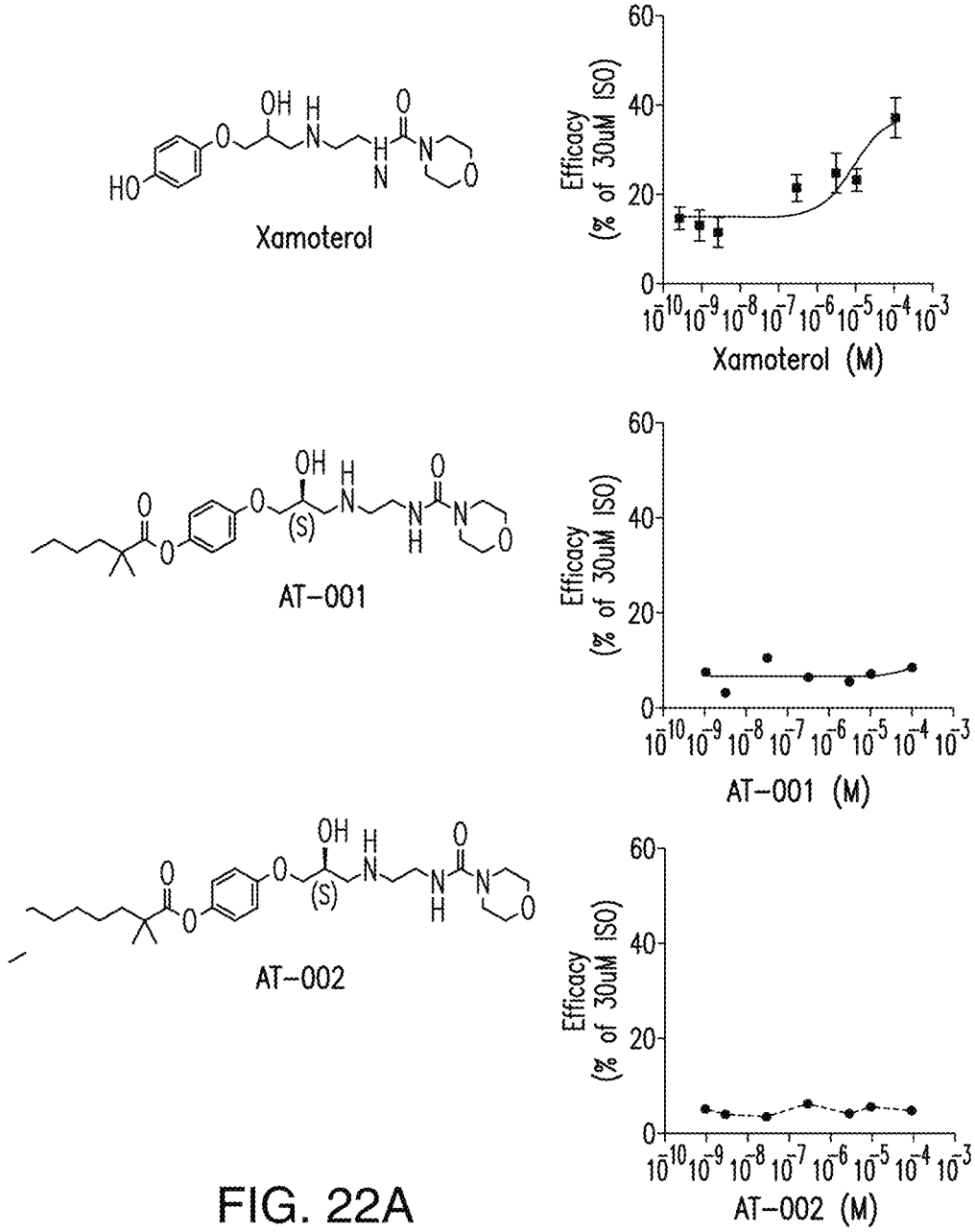
Figure 22B:
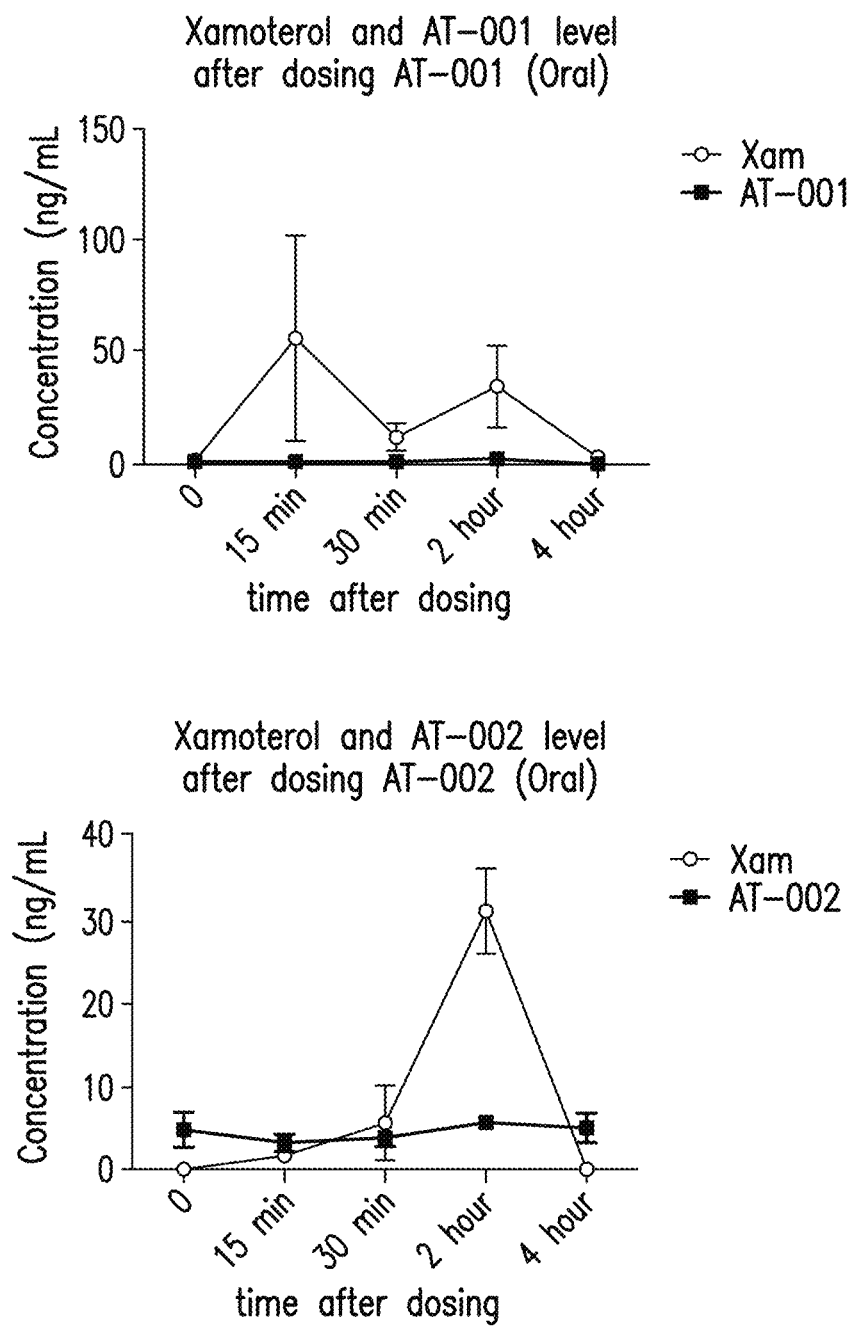

FIG. 22(A)-(B): illustrates that prodrugs of xamoterol do not activate the cAMP signaling pathway, and that the prodrugs are converted to xamoterol in vivo. (A) shows the molecular structures of xamoterol and two prodrugs (AT-001) and (AT-002), and their pharmacological effects on cAMP signaling pathway. (B) shows plasma concentration versus time profiles of xamoterol and AT-001 (upper) and AT-002 (lower) following oral injection of the two prodrugs. The xamoterol plasma level reflects the time required for, and the extent of, hydrolysis of the prodrugs to produce xamoterol in vivo. For both prodrugs, dosing was done orally.

Figure 23:
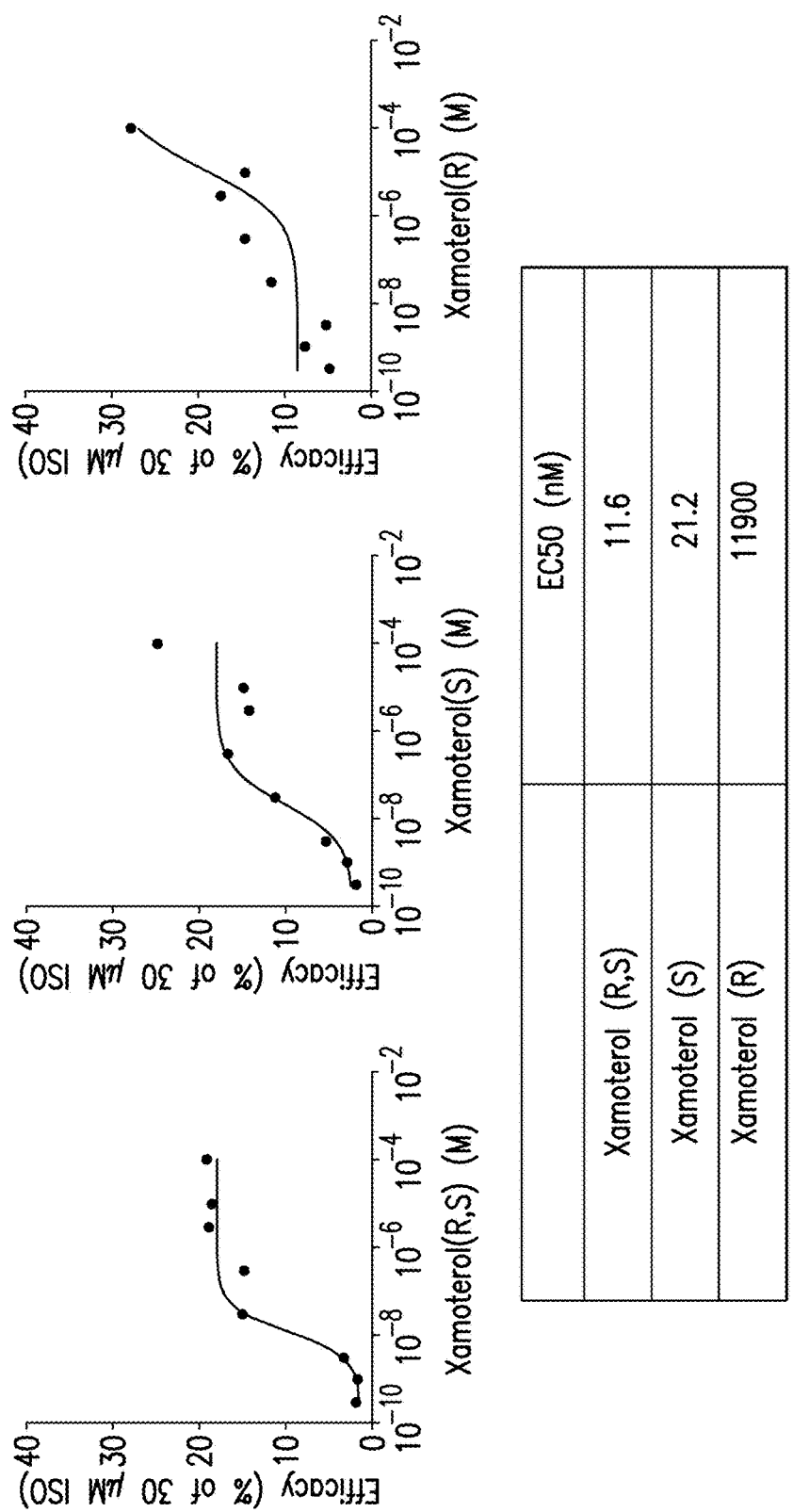

FIG. 23: illustrates that the R- and S-enantiomers of xamoterol have distinctly different pharmacological activities as the S-enantiomer is about 500 times more potent than the R-enantiomer in β1-ADR agonism. The EC$_{50}$ (nM) values for xamoterol (R,S), xamoterol (S) and xamoterol (R) are 11.6, 21.2 and 11900, respectively. These are concentration-response curves for xamoterol (racemate), and R- and S-enantiomers of xamoterol.

Figure 24:
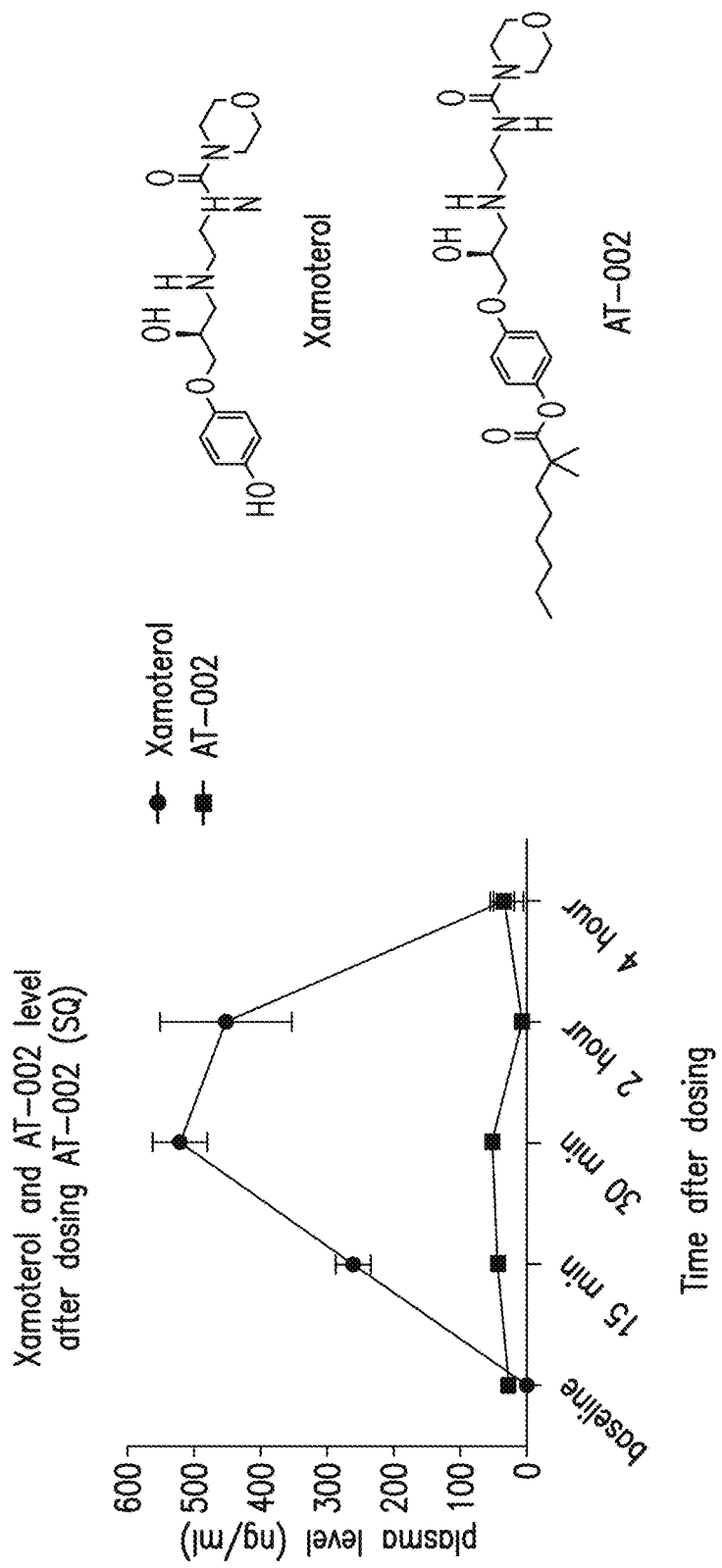

FIG. 24: illustrates the rapidity with which subcutaneous (subQ) dosing with AT-002 affords high plasma levels of xamoterol from in vivo hydrolysis. SubQ injection is, perhaps, the the fastest and most effective means of administering lipophilic prodrugs of xamoterol to attain high plasma levels of xamoterol.

DETAILED DESCRIPTION OF THE EMBODIMENTS

The present invention is based upon several fundamental discoveries. First, the present inventors have discovered that β$_1$-noradrenergic signaling regulates the cognitive function of social recognition, and may be used as a therapeutic target for treating neurodegenerative diseases, such as AD, DS, ADD, ADHD and/or Autism.

Second, the present inventors have also discovered that Thy1-hAPP$^{Lond/Swe+}$ mice display social recognition deficit. They have also discovered that WT mice treated with betaxolol, a selective β$_1$-ADR antagonist, displayed social recognition deficit associated with reduced c-Fos activation in β$_1$-ADR expressing cells and a reduced pCREB level in MeA. Additionally, it was observed that direct injection of the PKA inhibitor in MeA leads to a similar social recognition deficit.

Third, the present inventors have discovered that β$_1$-adrenergic receptor agonists, such as xamoterol, for example, rescues the social recognition deficit of Thy1-hAPP$^{Lond\ Swe+}$ mice by increasing the level of nuclear pCREB.

Fourth, the present inventors have also discovered that activation of β$_1$-ADR by agonists reduces or inhibits hyperactivity, and, thus, provide a method of treating attention deficit disorder (ADD) and/or attention deficit hyperactivity disorder (ADHD).

Fifth, the present inventors have also discovered that agonistic stimulation of the β$_1$-ADRs affords a mechanism for enhancing social memory, which is an advantageous method for treating the observable declines in social memory occurring with DS and/or Autism. In fact, the present inventors have discovered that activation of the β$_1$-ADRs is necessary for social recognition.

Sixth, the present inventors have discovered that various prodrugs of xamoterol having enhanced lipophilicity provide increased bioavailability for the uses disclosed herein.

Seventh, the present inventors have also discovered that differences in activity between the R- and S-enantiomers of the various prodrugs of xamoterol may be used advantageously to provide enantiomers having high β1-ADR agonist activity to produce enhanced improvement of cognition and reversal of hyperactivity.

Eighth, the present inventors have further discovered an enantioselective synthesis for preparing either R- or S-enantiomer prodrugs of xamoterol, as well as a synthetic procedure for preparing racemc xamoterol or prodrugs thereof.

The present invention pertains, in part, to lipophilic prodrugs of any β1-ADR agonist. However, of particular advantage are the lipophilic prodrugs of xamoterol. Xamoterol has the formula:

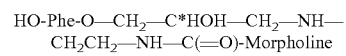

HO-Phe-O—CH$_2$—C*HOH—CH$_2$—NH—CH$_2$CH$_2$—NH—C(=O)-Morpholine where Phe is phenyl, with the terminal OH and OCH$_2$ para to each other, morpholine is the morpholine ring, and * denotes a chiral carbon. —C(=O)— represents a carbonyl group. See the top formula in FIG. 17, for the structural representation of xamoterol.

Generally, the lipophilic compounds of xamoterol are prepared by covalently bonding a hydrolyzable group to the terminal —OH group bonded to the phenyl ring or to the hydroxy group bonded to the chiral carbon or both provided that the hydrolysable group is both lipophilic and enhances the lipophilicity of the entire molecule, and which hydrolysable group is hydrolysable in vivo. Non-limiting examples of such hydrolysable groups are acyl, carbamate ester and oxoazolidine groups. Generally, all of these groups may be used, in essence, as a lipophilic blocking group for the terminal phenyl hydroxyl group or for the hydroxy group bonded to the chiral carbon or both which is group is hydrolysable in vivo to release free xamoterol, either as a racemate or as the (R)- or (S)-enantiomer. These same groups may also be used to form esters at the terminal hydroxy groups of any β1-ADR agonist compound, such as noradrenaline, isoprenaline or dobutamine, for example, to improve lipophilicity, and, thus, bioavailability and CNS availability. Both nordrenalin and isoprenaline have two terminal phenyl hydroxy groups and one secondary hydroxy group. Dobutamine has three terminal phenyl hydroxy groups, but no secondary hydroxy group. Hence, the methodology as described below for xamoterol is specifically contemplated for use with any other β1-ADR agonist compounds, such as noradrenalin, isoprenaline and dobutamine, for example.

The NA system represents the most underestimated, but important, neuropharmalogical target in AD. Postmortem brains from AD patients show progressive and extensive degeneration of locus coeruleus (LC), the primary source of NA in the brain. Biochemical changes such as decreased cortical levels of NA and changed expression of adrenergic receptors (ADRs) and NA transporter have also been described in both human AD patients and AD mouse models. Importantly, NA pathology has been found to correlate with several key aspects of AD. Further, since NA has well-established effects on cortical circuitry and synaptic function that are related to learning and memory.

The reduction of NA neurons has been shown to be positively correlated with the severity of dementia and chemical ablation of the LC using the neurotoxin N[2-chloroethyl]-N-ethyl-2-bromobenzylamine has been shown to exacerbate cognitive deficits in transgenic mouse models of AD. Moreover, NA system dysfunction has been implicated in other diseases characterized by memory impairment including dementia pugilistica, mild cognitive impairment, Wernicke-Korsakov syndrome and Down syndrome. It has also been shown that LC neuron degeneration and NA deficiency are strongly correlated with several pathological features of AD including tissue load of amyloid plaques and neurofibrillary tangles. In fact, the correlation between NA deficiency and neuropathological hallmarks of AD can be explained by the important role of the former in inflammatory response. For example, it has been shown that NA can activate microglia, which may have a neuroprotective function both by secreting proteolytic enzymes degrading β-amyloid peptides (Aβ) and by mediating endocytosis of Aβ.

The present inventors have discovered that $\beta_1$-ADRs play an important role in social recognition and memory, and thus may be utilized in therapies intended to improve cognition and social recognition/social memory in humans having deficiencies in these traits due to a neurodegenerative disorder, such as Alzheimer's disease. We investigated the social recognition/memory in the Thy1-APP$^{Lond/Swe}$ (APP) mouse model of AD using pharmacological and molecular tools and showed the social recognition deficit observed in APP mice is associated with abnormalities in $\beta_1$-ADR signaling in the MeA. Pharmacological activation of the $\beta_1$-ADR and restoring the pCREB levels in APP mice rescues the social memory deficit otherwise detected in this model of AD. Our results for the first time demonstrate that the $\beta_1$-ADR and CREB phosphorylation in the MeA is an essential signaling cascade for social learning under normal brain function.

Many different compounds and combinations of these compounds and their pharmacologically-acceptable salts are explicitly contemplated for use as $\beta_1$-ADR agonists in accordance with the claimed invention.

For example, compounds, such as xamoterol, isoprenaline, dobutamine and dopamine or salts thereof maybe used as $\beta_1$-ADR agonists. Additionally, prodrug-derivatives or prodrug-compounds, such as acyl- or amide-derivatives by functionalization at molecular hydroxyl groups may be used as well, and also the salts thereof. Of particular interest, however, are prodrug compounds of xamoterol having an acylated terminal phenyl hydroxyl group and the R- and S-enantiomers of these prodrug compounds of xamoterol. These compounds are described further below in more detail.

TERM DEFINITIONS

The terms indicated below are used throughout this specification, and have the meanings as defined below.

Neurodegenerative disorder: Means any neurodegenerative condition, disorder or disease that causes a mammal, including a human, who exhibits the condition, disorder or disease to display a diminished cognition or social recognition or social memory relative to a normal or control mammal, including human, exhibiting normal or typical cognition or social memory or social memory as would be expected for that class of mammal, including human, by conventional wisdom and knowledge. Non-limiting examples of such condition, disorder or disease are Alzheimer's disease (AD), and/or Autism.

Social recognition: means the ability of a mammal, including a human, to recognize other mammals, including humans, as measured by established tests in the case of non-human mammals, and by facial recognition by humans as indicated by behavior or speech.

MeA: means medial amygdala.

PKA: means protein kinase A, a family of enzymes.

CREB: means cAMP response element-binding protein, which is a cellular transcription factor binding to certain DNA sequences called cAMP response elements (CRE). Genes whose transcription is regulated by CREB include, for example, c-fos, the neurotrophin BDNF and many neuropeptides, such as somatostatin.

cAMP: means cyclic adenosine-3',5'-monophosphate. The cAMP dependent pathway means the adenylyl cyclase pathway.

Beta-1 ADR or β1-ADR: means β1-adrenergic receptor.

Beta-1 ADR agonist or β1-ADR agonist: means any compound or pharmaceutically-acceptable salt thereof that exhibits either complete or partial agonism for β1-ADRs. Examples of such compounds include xamoterol, isoprenaline (also known as isoproterenol), dobutamine, noradrenalin or dopamine.

Prodrug-compound: means chemically-modified versions of a pharmacologically active compound that undergo in vivo chemical or enzymatic transformation to release the active compound or parent drug. More specifically, functional moieties amenable to chemical or enzymatic transformation are attached to pharmacologically active compounds to improve drug targeting. For example, acyl- or amide-derivatives functionalized from hydroxyl groups of the $\beta_1$-ADR parent (i.e., underivatized) compounds may be noted as examples of prodrug derivatives or compounds. By adding acyl- or amide-moieties to the parent compound, the bioavailability of the parent compound can be improved relative to the underivatized parent compound. In the present specification, the term "derivative" is used interchangeably with "prodrug compound." Of particular advantage for the present invention are prodrug compounds of xamoterol having an acylated terminal phenyl hydroxyl group or secondary hydroxy group or both, wherein the $R_1$ or $R_2$ group of the acyl group may be from 5 to 30, preferably 9 or 10 to 30 carbons total for both. Both $R_1$ and $R_2$ are defined further below in more detail. The term "derivatized" as used herein means the formation of $R_1$ or $R_2$ group containing prodrug β1-ADR compounds from the corresponding β1-ADR agonist compound.

Salts: means pharmaceutically-acceptable salts, including both organic- and inorganic-acid addition salts. Examples of organic acid salts include, for example, acetate, citrate, succinate, oxalate, fumarate, hemifumarate, lactic, salicylic, benzoate and adipate. Examples of inorganic acid salts include, for example, hydrochloric, hydrobromic, phosphate and sulfate.

c log P: means computed log P, a measure of differential solubility or rather hydrophobicity as the octanol/water partition coefficient. Generally, a negative value for log P, such as −0.50, is indicative of poor bioabsorption and poor bioavailability. A positive value for log P, such as 1.00, indicates better bioabsorption and better bioavailability. The present invention specifically discloses the preparation and use of $\beta_1$-ADR agonist compounds derivatives or prodrugs having enhanced lipophilicity relative to the lead or parent $\beta_1$-ADR agonist compounds, and generally with a c log P value for the derivative or prodrug that has at least +0.50, and preferably at least +1.00 log P value greater than that for the lead or parent compound. More preferably, the c log P difference is at least +1.50 log P value. The higher the c log P value the better.

The present invention provides $\beta_1$-ADR agonist compounds as well as prodrugs or derivatives thereof. Specific examples of $\beta_1$-ADR agonist compounds include isoprenalin, dobutamine, noradrenalin, dopamine and xamoterol, for example. Various prodrugs of these $\beta_1$-ADR agonist compounds include compounds, for example, where terminal phenyl hydroxyl groups or secondary hydroxy groups of these agonist molecules are derivatized to form $R_1$ or $R_2$ groups, respectively, which groups may be, for example, —O—(C=O)-lower alkyl, —O—(C=O)-aminoalkyl or —O—(C=O)-phenyl or —O—(C=O)-substituted phenyl. Where these agonist molecules also have secondary hydroxyl groups, these groups may be derivatized to form $R_2$ groups, where $R_2$ may be as defined for $R_1$. For both $R_1$ and $R_2$, lower alkyl means $C_1$-$C_6$ alkyl which may be linear of branched alkyl. Aminoalkyl means —NH-alkyl, where alkyl means $C_1$-$C_6$ linear or branched alkyl. Phenyl is self-defining, and substituted phenyl means a phenyl substituted one or more lower alkyl, halo or hydroxyl groups. Here, lower alkyl means $C_1$-$C_6$ alkyl which may be linear or branched. It is again noted that in the present specification the term "derivative" is used interchangeably with "prodrug" as the derivatization is for the purpose of increasing the lipophilicity of the parent $\beta_1$-ADR agonist compound. The term "parent" simply means the $\beta_1$-ADR agonist compound before derivatization or "lead compound". Of particular advantage are the prodrug compounds of xamoterol having an acylated terminal phenyl hydroxyl group of the general formula R—(C=O)—O—, wherein R is a lipophilic group which improves the lipophilicity of the entire prodrug molecule relative to xamoterol, and wherein R has from 5 to 30 carbon atoms which are linear, branched or cyclic or a combination thereof, which are unsubstituted or optionally substituted with 1 to 4 lower alkyl, lower alkoxy, hydroxy or halo, and wherein the cyclic group is a 5- or 6-membered ring that contains 0, 1 or 2 heteroatoms, said heteroatoms being —O— or —N— or both, said cyclic group being saturated or unsaturated. The 5- or 6-membered rings may be, for example, pyrrole, furan, imidizoline, imidazole, pyrazolidine, pyrazole, pyridine or pyran, which as noted may be unsubstituted or optionally substituted by 1 to 4 lower alkyl, lower alkoxy, hydroxy or halo. Halo may be chloro or fluoro, but is preferably fluoro. The term "lower" means $C_1$-$C_6$ in all structural definitions and formulae herein, such as lower alkyl or lower alkoxy, for example. Bonded within the prodrug compound, the rings pyrrole, furan, imidizoline, imidazole, pyrazolidine, pyrazole, pyridine and pyran are, of course, pyrrolyl, furanyl, imidizolinyl, imidazolyl, pyrazolidinyl, pyrazolyl, pyridinyl and pyranyl.

For the sake of convenience, $R_1$ and $R_2$ groups used to form prodrugs of $\beta_1$-ADR agonist compounds will be consistently designated throughout this application such that $R_1$ refers to the hydrolysable group attached to terminal phenyl hydroxy groups, and $R_2$ to the hydrolysable group attached to the secondary hydroxy group as shown in the lower structure in FIG. 17.

KO: means knockout (mice).

Short term memory: means primary or active memory from short term storage, and is sometimes referred to as working memory.

Long term memory: means a continuously stored information, which can be called into working memory when needed. In humans, long term memory is divided into declarative memory, which includes all of the memories that are available in consciousness; and procedural memory, which involves memories of body movement and how to use objects in the environment. Declarative memory may be further divided into episodic memory for specific events, and semantic memory for knowledge about the world.

Social memory: means an ability to retrieve recognition of names, faces or physical locations from working memory whether derived from short term or long term memory.

Bioreversible: means prodrugs or derivatives of the pharmacologically active agent can be readily transformed back to the original active compound through in vivo transformation, such as by hydrolysis, which may be either by enzyme or by pH/redox. As used herein, the terms bioreversible and/or hydrolysable do not imply one mechanism over the other.

Autism (or Autistic) Spectrum Disorder (ASD): means a group of developmental disabilities that can cause significant social, communication and behavioral challenges. ASD affects different people in different ways, such as the nature of the symptoms, when the symptoms start and the severity of the symptoms. For example, ASD symptoms may include varying measured intelligence (IQ), but poor ability to socialize and verbally communicate as well as manifestations of repetitive behavior. There may also be varying degrees of sensory sensitivity.

ANOVA: means analysis of variance

ADD: means attention deficit disorder

ADHD: means attention deficit hyperactivity disorder

ADME: means absorption, distribution, metabolism and excretion.

The Noradrenalin (NA) System and $\beta_1$-ADR Compounds and Their Lipophilic Derivatives The present invention is based, at least in part, upon the recognition that NA deficiency has been linked to multiple pathological features of AD, such as synaptic dysfunctions, as well as cognitive symptoms. The present invention is based, in part, upon the discovery that pharmacological modulation that would increase NA transmission can provide a more comprehensive and more comprehensive approach to treating AD, for example, than current methodologies. FIG. 9 illustrates the approach disclosed herein where activation of $\beta_1$-ADR provides both AD disease modifying effects in addition to restoration of cognitive function.

Specifically, in FIG. 9, restoration of NA signaling through $\beta_1$-ADR rescues cognitive decline associated with AD by increasing the level of cAMP response element-binding protein (CREB) phosphorylation and brain-derived neurotrophic factor (BDNF) necessary for the regulation of depolarization in interneurons and downstream modulation of neurotransmission needed for cognitive functions. Activation of $\beta_1$-ADR provides additional benefit by conferring neuroprotective potential against Aβ pathology through its effects on microglia activity. Further, increases in cAMP through $\beta_1$-ADR activation ameliorates cell and synaptic loss as well as possible neuroinflammation by inhibiting the release of cytokine tumor necrosis factor-alpha (TNFα).

Additionally, in addition to use of $\beta_1$-ADR as a therapeutic target for treating AD, the present invention also specifically also discloses targeting the signaling cascade downstream of the $\beta_1$-ADR in the central nervous system while maintaining minimal unwanted peripheral effects on cardiac function. A detailed schematic for use in evaluating prodrugs prepared in accordance with the present invention is shown in FIG. 10. The procedures illustrated in the schematic allow for both the identification and further development of $\beta_1$-ADR agonist derivatives that have improved brain distribution due to improved lipophilicity with minimal peripheral effects. This also provides for the preparation of a library or catalogue of synthesized bioreversible, i.e., hydrolysable derivatives of $\beta_1$-ADR compounds. The term "bioreversible" as used herein means hydrolysable in vivo to release the parent $\beta_1$-ADR compound from the prodrug of that $\beta 1$-ADR agonist compound.

The synthesized prodrugs are subjected to a battery of tests, such as in vitro absorption, distribution, metabolism and excretion (collectively known as ADME tests), and structure-property relationships (SPR) are developed based upon ADME properties. These studies or evaluations are conducted in an iterative manner and the obtained SPR is used to guide the design of additional prodrug compounds, and even new synthetic $\beta_1$-ADR agonist compounds in conjunction and the formation of prodrugs thereof. Derivatized $\beta_1$-ADR compounds that exhibit promising ADME properties are advanced to in vivo biodistribution and pharmacokinetic studies. Two compounds with the most favorable ADME and pharmacokinetic (PK) properties are tested in pre-clinical models for AD. Target product profiles (TPP) that contain data on both in vitro and in vivo PK properties as well as in vivo efficacy obtained from preclinical animal model studies are prepared for each derivative $\beta_1$-ADR agonist compound subjected to these tests.

Additionally, known $\beta_1$-ADR agonist compounds or other ligands that exhibit an agonistic effect on $\beta_1$-ADRs may be obtained from the literature and derivatized for subjection to the tests indicated above. TPP are also prepared for these derivatives as well in order to form a comprehensive catalog or library.

Xamoterol:

While any $\beta_1$-ADR agonist compound or ligand exhibiting agonistic effects on $\beta_1$-ADR may be used for derivatization, xamoterol has been found to exhibit several distinguishing pharmacological properties of use in the treatment of AD. First, the present inventors have discovered that xamoterol selectively activates a cAMP cascade while exhibiting only minimal activity on the β-arrestin signaling pathway. FIG. 8 illustrates this pharmacology of xamoterol. Notably, xamoterol, as an agonist for the $\beta_1$-ADR, stimulates cAMP signaling to elicit about 60% of the maximal response to the agonist isoprenaline (A). On the other hand, xamoterol has no effect on the β-arrestin pathway as opposed to indiscriminate isoprenaline, which activates both cAMP and β-arrestin pathways (B). The β-arrestins are a family of proteins that regulate signal transduction to $\beta 2$-ADRs, which has a role in regulating cardiac function.

The functional selectivity of xamoterol, for example, in lacking β-arrestin signaling activity has second important implication, which is consistent and sustained efficacy. More specifically, the therapeutic utility of agonist therapies has often been limited by the development of tolerance and tachyphylaxis, which are mediated by β-arrestin signaling dependent receptor desensitization. In fact, an animal study using rat ventricles has shown that prolonged administration of xamoterol did not induce reduction in $\beta_1$-ADR density or adenylate cyclase coupling efficiency.

A third important property of xamoterol is the sub-type selectivity for the $\beta_1$-ADR over the closely related receptor $\beta_2$-ADR. $\beta_1$-ADR is universally coupled to adenylyl cyclase and its activation lead to increases the level of CREB phosphorylation. As such, activation of $\beta_1$-ADR would be expected to rescue CREB-dependent memory deficits. Thus, the sub-type selectivity of xamoterol, in particular, would be expected to enhance cognitive function through $\beta_1$-ADRs while avoiding interaction with the $\beta_2$-ADRs.

A fourth important property of xamoterol is that it passes the BBB and reach the central nervous system, as demonstrated by the present inventors, where it induces an increase in CREB phosphorylation and mediates pro-cognitive effects. See Table 1 below and FIG. 9.

TABLE 1

Analysis of xamoterol concentration in plasma and brain samples after s.c. injection of 3 mg/kg of xamoterol in mice

| Time point | Plasma (ng/ml) | Brain (ng/ml) | P/B ratio |
| --- | --- | --- | --- |
| 30 minutes | 273.7 ± 75.9 | 168.0 ± 6.4 | 1.1 ± 0.4 |
| 1 hour | 45.1 ± 6.1 | 116.0 ± 9.1 | 0.4 ± 0.04 |
| 2 hours | 4.7 ± 0.7 | 124.7 ± 7.4 | 0.04 ± 0.01 |

FIG. 8 illustrates the effects of xamoterol on pCREB expression in mice brain s.c. injection of 3 mg/kg of xamoterol in mice induces a significant increase of pCREB in the brain after 15 minutes. *** p<0.001.

All of the above data indicates that xamoterol, for example, has significant therapeutic value for the treatment of AD. Thus, the derivatization of xamoterol, for example, to enhance its pharmacokinetic properties and CNS availability yields an even more potent compound for the treatment of AD.

Finally, an additional advantage of xamoterol is that it is well-tolerated by humans without any significant side effects.

Experiments with Xamoterol:

Previously, the present inventors showed that injection of the selective $\beta_1$-ADR antagonist betaxolol impairs social and contextual memory in wild type (WT) animals. Notably, social recognition and contextual memory became impaired in C57B1/6 mice treated with a single dose of 1 mg/kg of betaxolol. $\beta_1$-ADR KO mice have impaired social recognition while their control littermates or $\beta_2$-ADR KO mice performed normally  p<0.01; * p<0.0001 vs. chance level (zero) as observed by experiment.

Besides the social and contextual memory, studies with betaxolol on a Y-maze test also demonstrated important roles of $\beta_1$-ADR in spatial memory. Additionally, $\beta_1$-ADR KO mice display impaired social and contextual memory while $\beta_2$-ADR KO mice have normal memory function.

Collectively, these results indicate the essential roles of $\beta 1$-ADR in various forms of cognitive functions, and that restoration of $\beta 1$-ADR signaling provides a therapeutic strategy to improve cognitive function in AD.

Furthermore, the present inventors have demonstrated that an acute subcutaneous (s.C.) injection of 3 mg/kg of xamoterol rescues working memory and social recognition deficits in Thy1-APP$^{Lond/Swe+}$ mouse model of AD. Importantly, an unregulated expression of $\beta_1$-ADR has been observed in specific brain regions of Thy1-APP$^{Lond/Swe+}$ mice, such as the medial amygdala. The increased expression of β1-ADR indicates that postsynaptic expression for NA remain functional despite the degeneration of the LC and impaired NA signaling can be restored with β$_1$-ADR agonists and their lipophilic derivatives having improved ADME and bioavailability. In the 5xFAD mouse model of AD, the effects of chronic oral dosing with xamoterol on cognitive impairment have also been observed. Notably, a daily oral dose of 6 mg/kg of xamoterol over 3 months rescues the declarative and spatial memory deficits observed in 5xFAD mice.

No Side Effects Resulting from β1-ADR Activation

In a pilot study, histological examination of cardiac tissue showed that chronic treatment with xamoterol (3 mg/kg s.c. for 3 months) did not induce cardiac fibrosis. Similarly, wild type mice treated with xamoterol did not (3 mg/kg s.c. for 3 months0 did not develop pathological changes in cardiac functions measured by blood pressure (BP), heart rate (HR), ejection fraction (EF), fractional shortening (FS) and heart weight:body ration. Furthermore, clinical studies in humans with heart failure have shown the efficacy of chronic treatment with xamoterol (200 mg twice daily for 2-12 months) without any significant side effects. This indicates that chronic treatment with xamoterol, for example, for AD will not be associated with unwarranted side effects on cardiac functions in humans.

The present invention will be further exemplified by certain non-limiting examples:

EXAMPLES

Materials and Methods

Animals. Adult C57B1/6 mice (Jackson Laboratory, #000664), β$_2$-ADR (knockout) KO mice (provided by Dr. R G Giffard), β$_1$-ADR KO mice (provided by Dr. D. Bernstein) and their age-matched controls (FVB/NJ mice from Jackson Laboratory, #001800), and Thy1-hAPP$^{Lond/Swe+}$ mice (APP), model of AD were used. Experiments were in accordance with protocols approved by the Institutional Animal Care and Use Committee of Stanford University and were performed based on the National Institutes of Health Guide for the Care and Use of Laboratory Animals.

Behavioral testing. Social recognition was tested in two different tests: the 3-chamber social test developed by Nadler et al and the in-home cage social discrimination task developed by Macbeth et al. To differentiate between social recognition and recognition of non-social odors/objects non-social odor discrimination tests (olfactory habituation/dishabituation and olfactory recognition test) and an object recognition test were used.

Drug treatment. The β$_1$-ADR partial agonist, xamoterol, the β$_1$-ADR antagonist, betaxolol and the protein kinase A (PKA) inhibitor, PKI 14-22 amide myristoylated (Tocris bioscience, Minneapolis, Minn., USA) were used. Xamoterol was injected sub-cutaneously (3 mg/kg). Betaxolol was injected sub-cutaneously (1 mg/kg) or in the MeA (30 nmole/side). PKI 14-22 amide was dissolved in 30% acetonitrile and injected in the MeA (2.75 nmole/side).

Molecular analyses. Immunohistochemistry was used to assess c-Fos, tyrosine hydroxylase (TH) and β$_1$-ADR. The quantitative analysis of stained cells was done in different brain regions according to the Mouse Brain Atlas. Cell counting was achieved using the unbiased-stereologic method. The total number of positive cells was quantified with the optical fractionator method using the StereoInvestigator software (MBF Bioscience, Williston, Vt., USA). The counting criteria were determined so as to obtain a mean coefficient of error ≤0.10. Analysis of pCREB was performed by western blot.

Statistics. Data were analyzed using the software Prism 5.01 (GraphPad Software Inc., CA, USA). For behavioral and pharmacological testing a minimum of 5 animals per group and for immunohistochemistry and western blot 3 to 4 animals per group were used.

Results

Figure 1B:
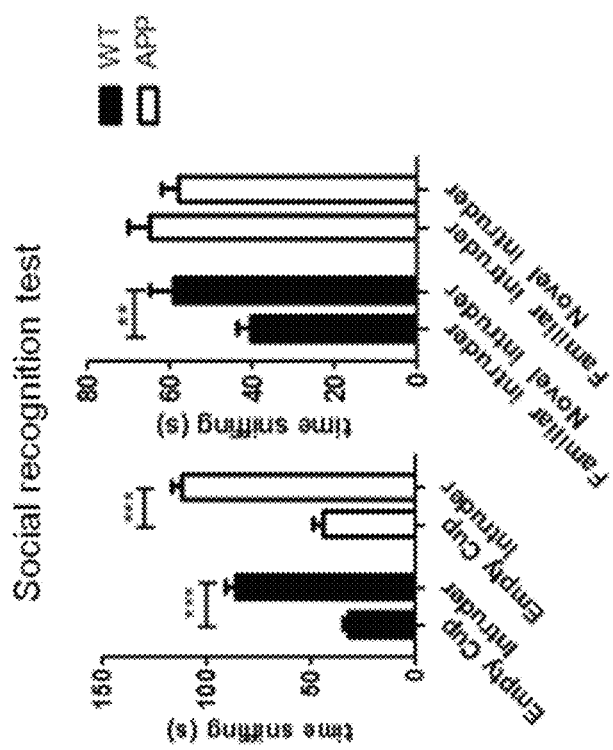
FIG. 1 (A)-(D): APP mouse model of Alzheimer's disease are characterized by impaired social recognition, and upregulation of the $\beta_1$-ADR expression in the MeA. In the left, the schematic Representations of the experiments are shown. (A) Both Wild-type (WT; n=11) and APP (n=9) Mie explored a cup containing an unfamiliar C57B1/6 intruder mouse over an empty cup Showing normal sociability (* p<0.0001 by paired t-test): (B) However, while WT showed a preference for a novel C56B1/6 intruder over a familiar one ( p<0.0067 by paired t-test), APP mice did not display this preference (p=0.2780 by paired t-test), indicative of social recognition deficits. This deficit in social recognition is not associated with deficit in non-social odor recognition. (C) Both WT (n=7) and APP (n=8) mice sniffed more a tube containing a heptanol solution over an empty tube ( p<0.01 by paired t-test); (D) Similarly, both WT and APP mice showed a preference for a tube containing a novel alcohol odor (heptanol:octanol solution) over the familiar one (heptanol alone) ( p=0.0062 and *** p=0.0001 by paired t-test), indicative that both genotypes can remember a familiar non-social odor. Data are presented as mean±SEM.
Figure 1A:
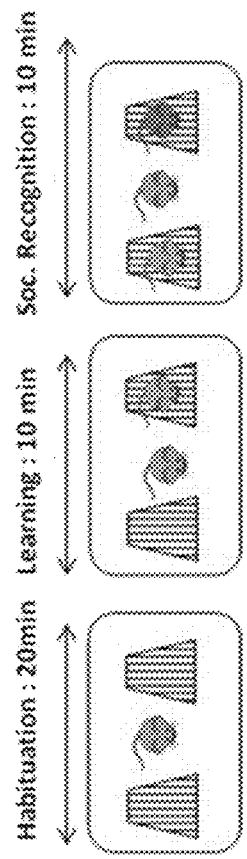
Figure 1D:
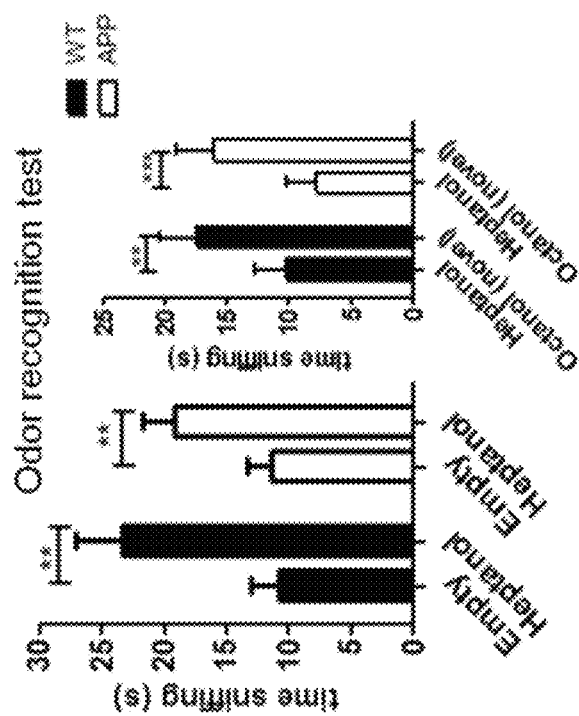
Figure 1C:
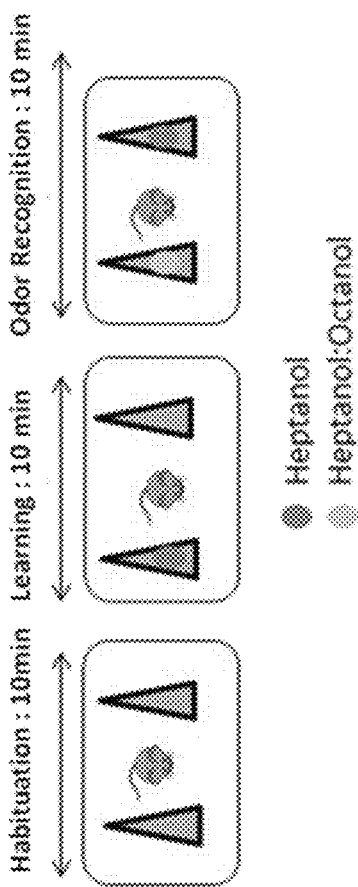

Social Recognition and β$_1$-Noradrenergic Neurotransmission are Impaired in a Mouse Model of Alzheimer's Disease In rodents, social recognition can be measured by a higher amount of time investigating a never-met conspecific compared to a previously-met one. We first investigated the ability of the APP mice, to recognize a previously-met conspecific. While they showed a preference for an unfamiliar intruder over an empty cup (FIG. 1A), they failed to demonstrate a preference for a new intruder over a familiar one, indicative of social recognition deficit (FIG. 1B). This deficit was not linked to a deficit in olfactory abilities or in discriminating between non-social odors (FIGS. 1C and 1D).

We then tested whether abnormalities in the expression of the β$_1$-ADR are present in APP mice and showed a significant higher number of β$_1$-ADR expressing cells in the MeA of APP mice compared to their control littermates. We have shown for the first time that this APP mouse model of AD recreates one important symptom characteristic of AD, the inability to recognize a previously met individual as well as abnormalities in the β$_1$-noradrenergic circuits in the MeA, the region known to be important for social memory.

β$_1$-ADR and its Downstream Signaling is Essential for Learning of Social Cues

Figures 2A, 2B:
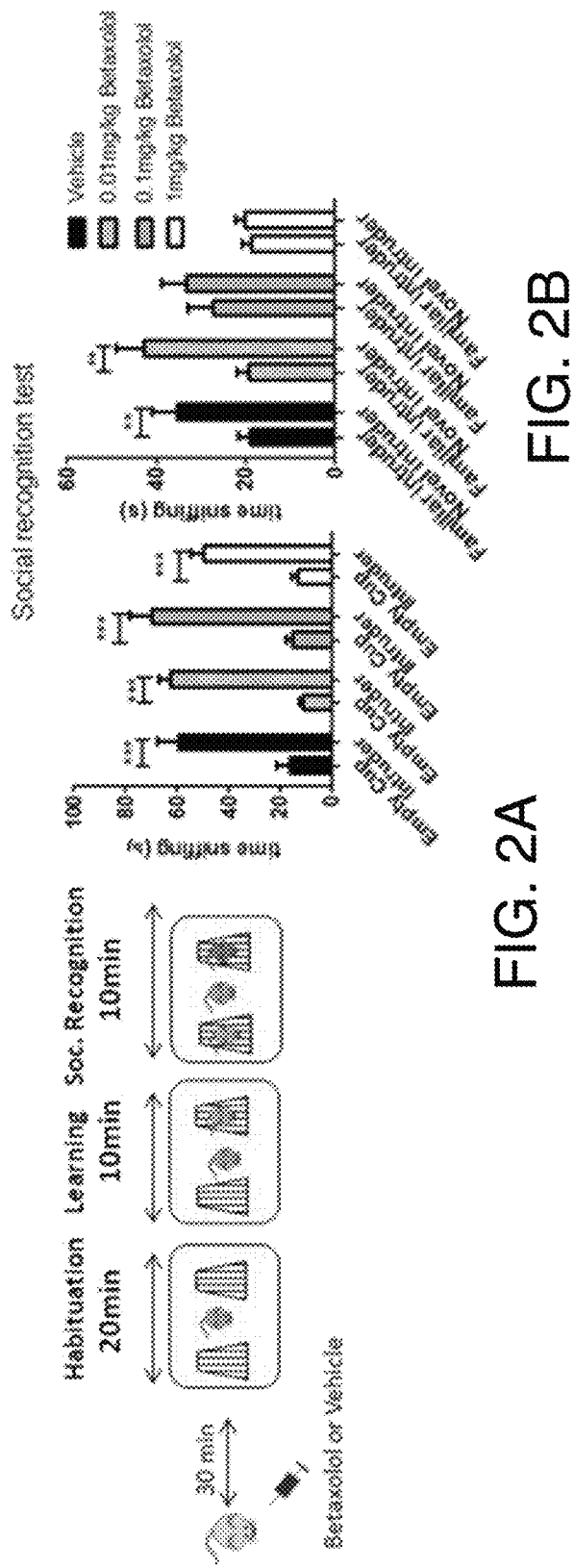

We then investigated the potential contribution of the β$_1$-ADR in social recognition to determine whether the abnormalities in the β$_1$-noradrenergic neurotransmission in APP mice could be responsible for their social memory deficit. We assessed the ability of C57B1/6 mice to recognize a previously-met conspecific after an acute subcutaneous injection of various doses of a selective β$_1$-ADR antagonist, betaxolol (0.01, 0.1 and 1 mg/kg). Although betaxolol, did not affect the preference for an unfamiliar intruder over an empty cup, 0.1 and 1 mg/kg of betaxolol resulted in an inability of mice to distinguish between a new and a familiar conspecific without affecting the total time spent exploring the two conspecifics (1-way ANOVA p=0.153) (FIGS. 2A and 2B). This finding was reproduced in a different behavioral paradigm that also assesses social recognition, the 3-chamber test. We then demonstrated that blockade of β1-ADR affects the recognition of social cues without affecting general olfactory abilities and discrimination (FIGS. 2C and 2D). These results were confirmed in an odor habituation/dishabituation paradigm. Finally, we observed that the ability to remember a familiar object was not different in the mice injected with betaxolol or vehicle.

Figures 2E, 2F:
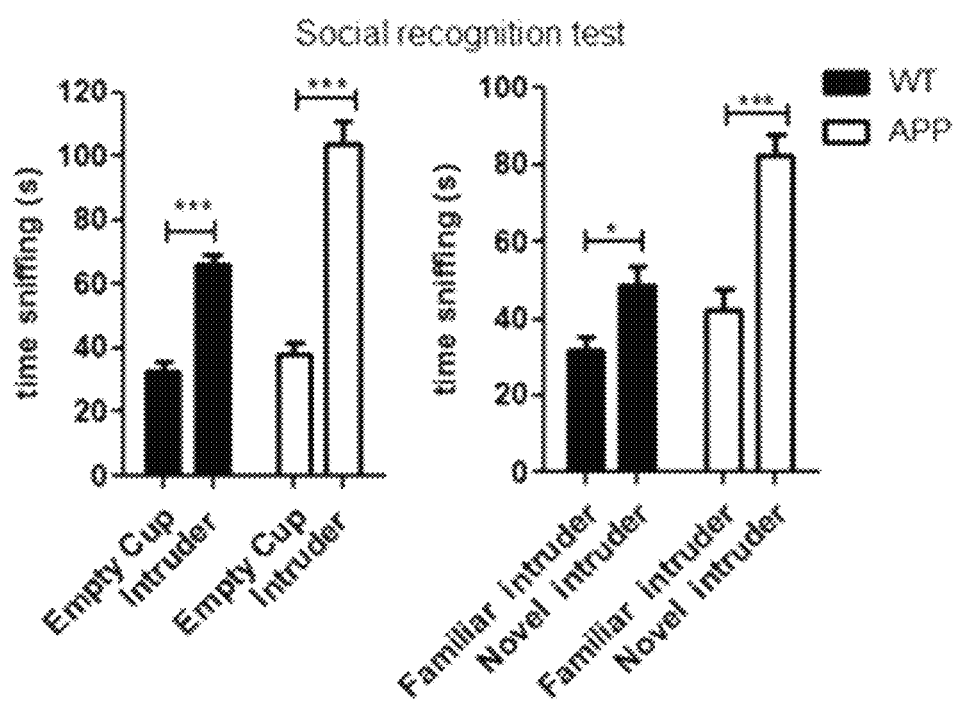

These results suggest that the β$_1$-ADR activation is necessary for social learning and recognition in mice. We thus propose that the abnormalities in the β$_1$-ADR expression level observed in the APP mice are responsible for their deficit in social recognition and restoring the function of the β1-ADR in APP mice would rescue the social recognition deficit. Injection of the β$_1$-ADR partial agonist, xamoterol in APP mice prior to social learning rescued the deficit previously observed (FIGS. 2E and 2F).

Figures 3A, 3B:
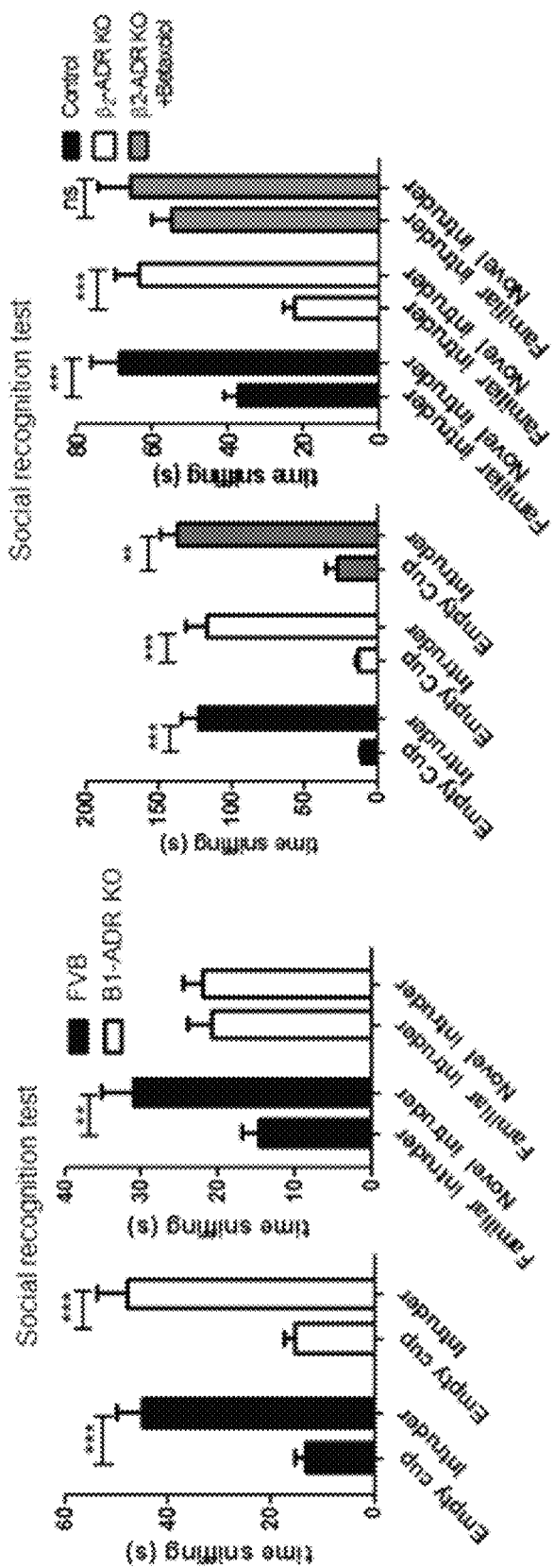
FIG. 3 (A)-(E): Activation of the $\beta_1$-ADR is necessary for the acquisition of social cues. (A) $\beta_1$-ADR KO mice (n=17) tested in the 3-chamber test show a preference for a cup containing an unfamiliar intruder over an empty cup (* p<0.0001), similarly to control mice (FVB mice n=16) (* p=0.0002). However, $\beta_1$-ADR KO mice failed to recognize a novel intruder over a familiar one, while their WT controls made this discrimination ( p=0.005 by paired t-test) (B) $\beta_2$-ADR KO mice (n=8) show a preference for a cup containing an unfamiliar intruder over an empty cup (* p=0.0002), similarly to control FVB mice (n=8; * p<0.0001) or $\beta_2$-ADR KO mice treated with 3 mg/kg of betaxolol (n=8;  p=0.001). Both FVB control and $\beta_2$-ADR KO mice show a preference for a novel intruder over a familiar one (* p=0.0004 by paired t-test) indicative of normal social recognition abilities even in mice lacking the $\beta_2$-ADR; in addition, betaxolol effectively impaired social recognition abilities in $\beta_2$-ADR KO mice (ns by paired t-test) suggesting that betaxolol effects on social recognition are not modulated by the $\beta_2$-ADR. Data are presented as mean±SEM. (C) Systemic injection of betaxolol (1 mg/kg) 30 minutes prior to the retrieval phase of the test did not impair social recognition; both vehicle-injected and Betaxolol-injected mice (n=8) preferred a novel intruder over a familiar one ( p=0.0023 and * p=0.0136, respectively, by paired t-test). (D) Systemic injection of betaxolol (1 mg/kg) 20 minutes prior to the learning phase of the test impaired short term social recognition; betaxolol-injected mice (n=8) did not prefer a novel intruder over a familiar one (ns p=0.3889 by paired t-test) indicative of social recognition deficit, while vehicle-injected mice (n=8) showed this preference (*** p=0.0007 by paired t-test). (E) Systemic injection of betaxolol (1 mg/kg) 20 minutes prior to the learning phase of the test impaired long-term social memory; 24 hours after the learning phase, betaxolol-injected mice (n=8) showed this preference (* p=0.0119). Data are presented as mean±SEM.

Our pharmacological data indicate that the β1-ADR is necessary for social recognition. However, drug selectivity for a specific receptor is often controversial. To confirm that betaxolol targets specifically the $\beta_1$-ADR, and $\beta_1$-ADR (vs $\beta_2$-ADR) in social recognition we tested social recognition abilities in both $\beta_1$-ADR KO and $\beta_2$-ADR KO mice and their FVB controls. All mice showed a preference for a cup with an unfamiliar intruder over an empty cup. Then, while $\beta_1$-ADR KO mice have impaired social recognition (FIG. 3A), $\beta_2$-ADR KO mice perform correctly the task (FIG. 3B). In addition, betaxolol injection in $\beta_2$-ADR KO mice prior to social learning resulted in impaired social recognition (FIG. 3B). This suggests that the social recognition deficit induced by betaxolol is dependent on the $\beta_1$-ADR and not $\beta_2$-ADR and that the $\beta_1$-ADR is essential for social recognition.

Figure 3C:
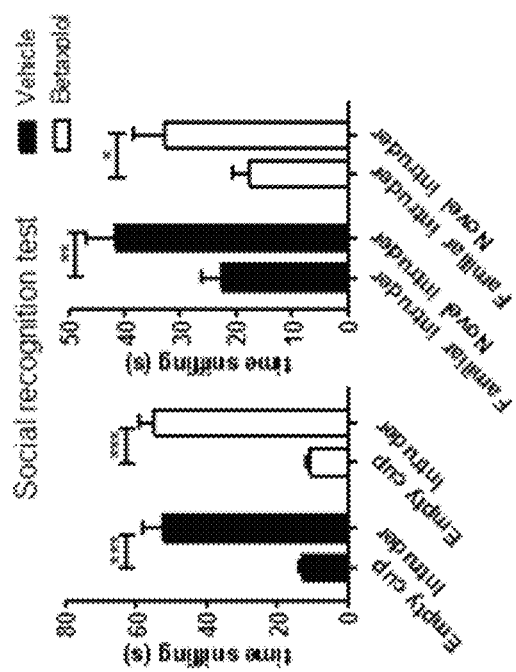
Figure 3C:
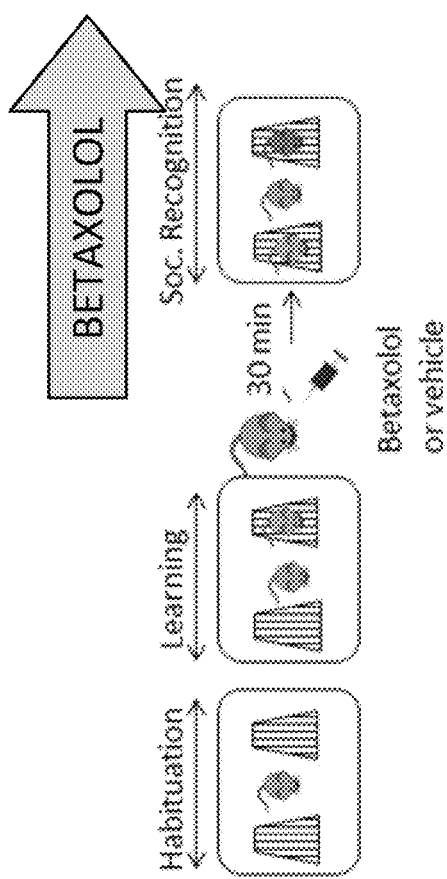
Figure 3D:
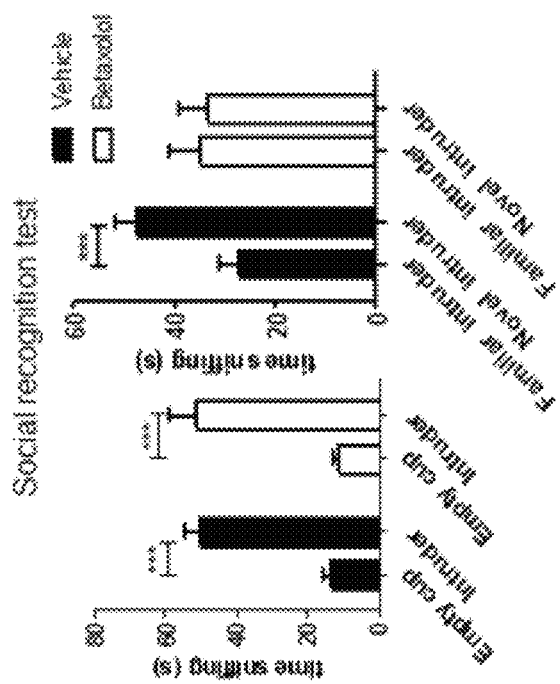
Figure 3D:
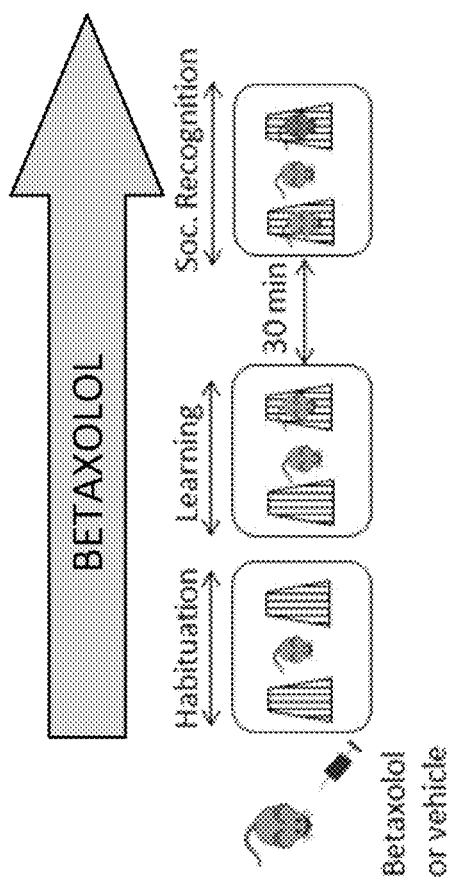
Figure 3E:
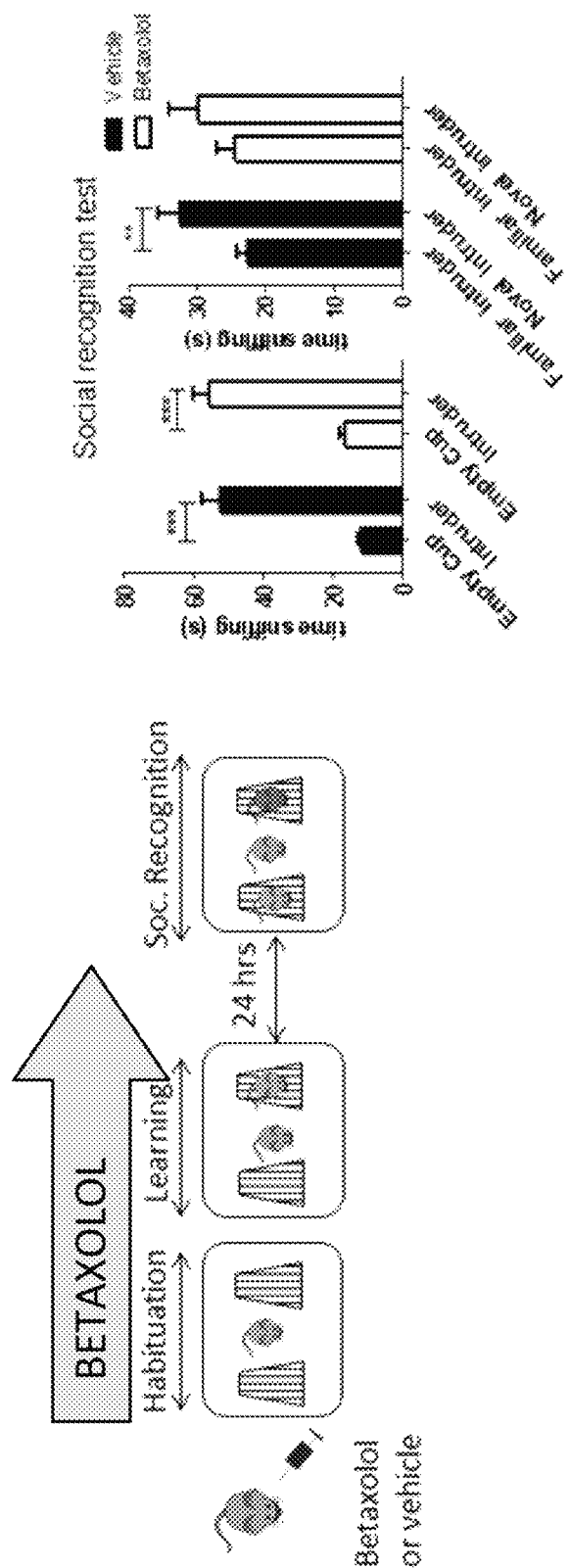

We next evaluated if the activation of the $\beta_1$-ADR is important during the acquisition of social cues (social learning) or during the retrieval of this information. We injected betaxolol either 20 minutes before the learning phase of the test or 30 minutes before the retrieval phase of the test. Inhibition of $\beta_1$-ADR during the learning phase led to social recognition deficit (FIG. 3C), while inhibition of $\beta_1$-ADR during the retrieval phase of the test did not impair social recognition (FIG. 3D). We then confirmed the importance of the $\beta_1$-ADR for learning of social cues by injecting betaxolol before the learning phase of a test of long-term social recognition. Mice injected with betaxolol prior learning and tested 24-hours later showed impaired social recognition while vehicle-injected mice had intact social recognition (FIG. 3E). Collectively, these data highlight for the importance of $\beta_1$-ADR for the learning of social cues, which is necessary for social recognition.

The $\beta_1$-ADR in the Medial Amygdala is Essential for Social Recognition

Figure 4A:
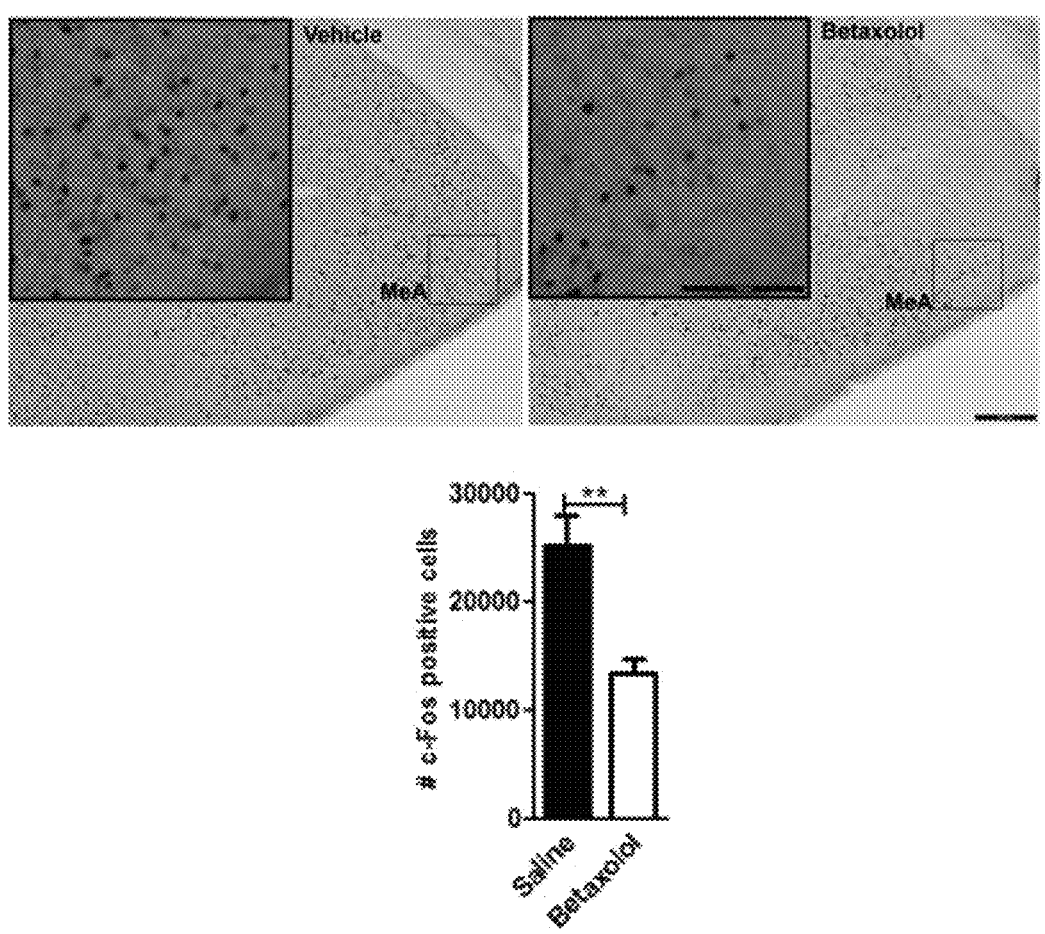
FIG. 4(A)-(D): Activation of the $\beta1$-ADR in medial amygdala (MeA) is necessary for social recognition. (A) Injection of betaxolol (1 mg/kg) prior to testing in a social recognition task decreased the number of c-Fos positive cells in the MeA (vehicle-injected mice n=4; betaxolol-injected mice n=4; ** p=0.0076 by t-test). (B) Schematic representation of coronal section shows the injection in the MeA. (C) Mice were injected in the MeA with either vehicle (n=5) or with 30 nmole of betaxolol (n=5). Betaxolol impairs social recognition in mice without affecting the social learning. Data are presented as mean±SEM. Scale bars, 50 µm. (D) Mice were injected in the MeA with either vehicle (n=4) or a PKA inhibitor (2.75 nmole–n=5). PKA inhibition did not affect the presence of mice for an unfamiliar conspecific over an empty cup (vehicle treated mice: * p=0.047 and PKA inhibitor treated mice: * p=0.02 by paired t-test) but impaired the ability of mice to recognize between a new and familiar conspecific (vehicle treated mice * p=0.031 and PKA inhibitor treated mice: ns by paired t-test).
Figure 4B:
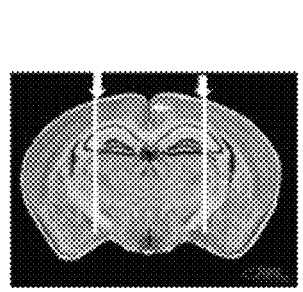

Brain regions involved in social recognition have already been defined. Among them are the lateral septum, prefrontal cortex and MeA. We first confirmed the importance of the MeA for social recognition. We used c-Fos as a marker of neuronal activity and compared its expression in a group of C57Bl/6 mice after social learning with a group of mice after both social learning and social recognition. Unbiased stereological counting revealed higher level of c-Fos expression after social recognition in the MeA but not in the basolateral amygdala confirming the importance of the MeA for the processing of social cues. We then observed that after injection of betaxolol, c-Fos expression in MeA was significantly reduced after social recognition (vs. vehicle injection) (FIG. 4A). This reduction was specific to regions activated during social recognition such as the MeA since we did not observe such an effect in the paraventricular nucleus of the thalamus, which is poorly expressed in $\beta_1$-ADR and not preferentially activated by social recognition. We also observed that the lower expression of c-Fos in the MeA induced by betaxolol is associated with lower c-Fos expression in $\beta_1$-ADR expressing cells: double immunostaining showed that the percent of $\beta_1$-ADR cells expressing c-Fos is significantly reduced in betaxolol-injected mice compared to vehicle-injected ones (FIG. 4B).

Figure 4C:
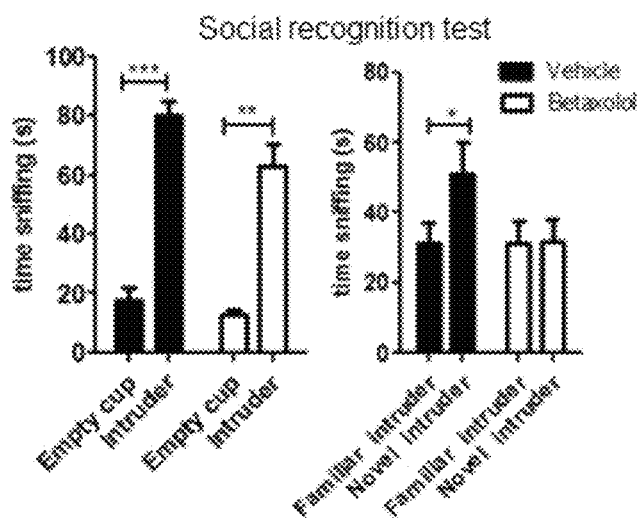
Figure 4D:
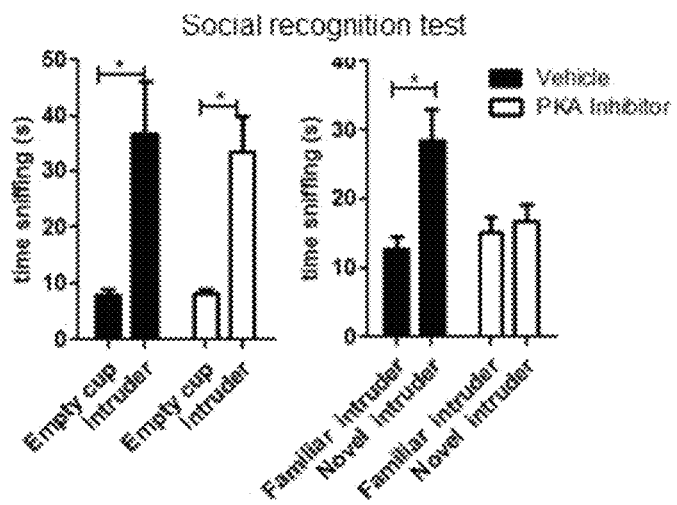

To further confirm the role of the $\beta_1$-ADR in the MeA for social recognition, betaxolol was directly injected in the MeA (FIG. 4C) of C57Bl/6 mice prior to social learning. Mice treated with betaxolol in the MeA were not able to recognize a familiar conspecific (FIG. 4D). Our results demonstrated that the MeA is an important structure for social recognition, that activation of $\beta_1$-ADR in the MeA is necessary for mice social learning and recognition.

The $\beta_1$-ADR is a G-protein coupled receptor associated with the Gs heterotrimeric G-protein. As such, one of the signaling pathways downstream of the $\beta_1$-ADR involves activation of the cAMP/PKA cascade resulting in cAMP response element-binding (CREB) phosphorylation. We thus analyzed whether the blockade of the pathway downstream of $\beta_1$-ADR by betaxolol impairs social learning and recognition. We first injected a PKA inhibitor in the MeA of C57Bl/6 mice prior to social learning to determine whether blockade of the PKA/CREB/pCREB cascade affects social recognition. We observed that blocking PKA impairs the ability of mice to recognize a familiar conspecific (FIG. 4E) without affecting the preference for an unfamiliar intruder over an empty cup during social learning. These results show that PKA activity is necessary for social learning and recognition. Together our results show that inhibition of $\beta_1$-ADR signaling pathway in MeA by betaxolol or a PKA inhibitor results in social recognition deficits.

$\beta_1$-ADR Modulates CREB Phosphorylation

Figures 5A, 5B:
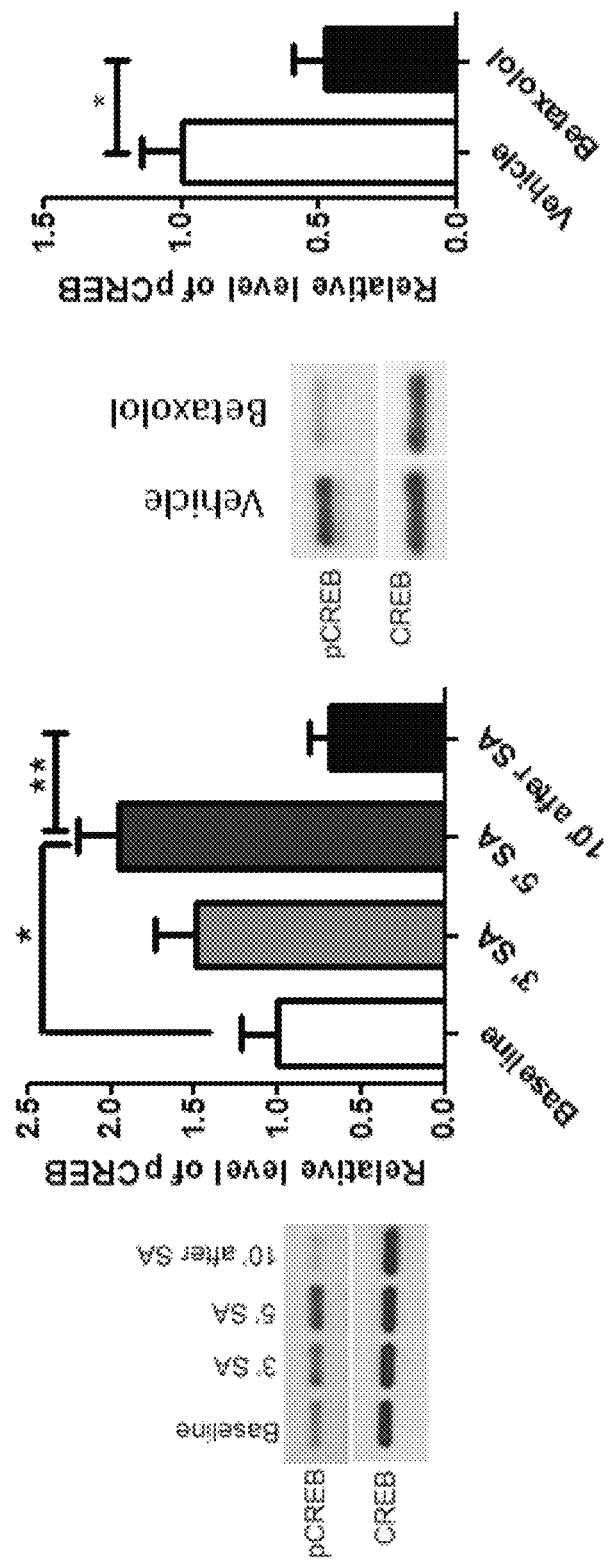
FIG. 5(A)-(D): CREB phosphorylation is necessary for social recognition. (A) Western blot analysis of pCREB performed on MeA extracts of C57B1/6 mice before social acquisition (SA) (baseline)(n=6), directly after 3 (n=6) or 5 minutes (N=5) of social acquisition and 10 minutes after a 5 minute social acquisition (n=6). pCREB expression was significantly increased after 5 minutes of social learning when compared to baseline values *, post hoc test following one-way ANOVA ((, p=0.0333)) and decreased 10 minutes after social learning was finished (, post hoc test following one-way ANOVA ((** p=0.0333)). The relative optical density is normalized To CREB. (B) Western blot analysis of pCREB performed on MeA extracts of C57B1/6 mice injected systematically 60 minutes before social learning with betaxolol (1 mg/kg) or vehicle (n=5 per group) and euthanized after 5 minutes of social interaction. pCREB expression was significantly decreased in the betaxolol-injected (* p=0.0113 by t-test). (C) Western blot analysis of pCREB performed on MeA extracts of C57B1/6 mice injected systematically with the $\beta1$-ADR partial agonist xamoterol (3 mg/kg) 5 min (N=6), 15 min (n=6) and 30 min (n=5) before euthanasia. pCREB expression was increased 5 min after injection when compared to baseline (n=5)(*, post hoc test following one way NOVA (* p=0.0415)). The relative optical density is normalized to CREB. (D) Western blot analysis of the nuclear fraction of medial amygdale of APP mice and the WT controls injected with xamoterol (n=4 APP, n=5 WT) or vehicle (n=4 APP, n=4 WT) prior to social learning showed that the level of nuclear pCREB was lower in APP mice (*, post hoc test following one-way ANOVA) and was significantly higher in the xamoterol injected group (, post hoc test following one-way ANOVA (, p=0.011)). The relative optical density is normalized to histone H3. Data are presented as mean±SEM.
Figures 5C, 5D:
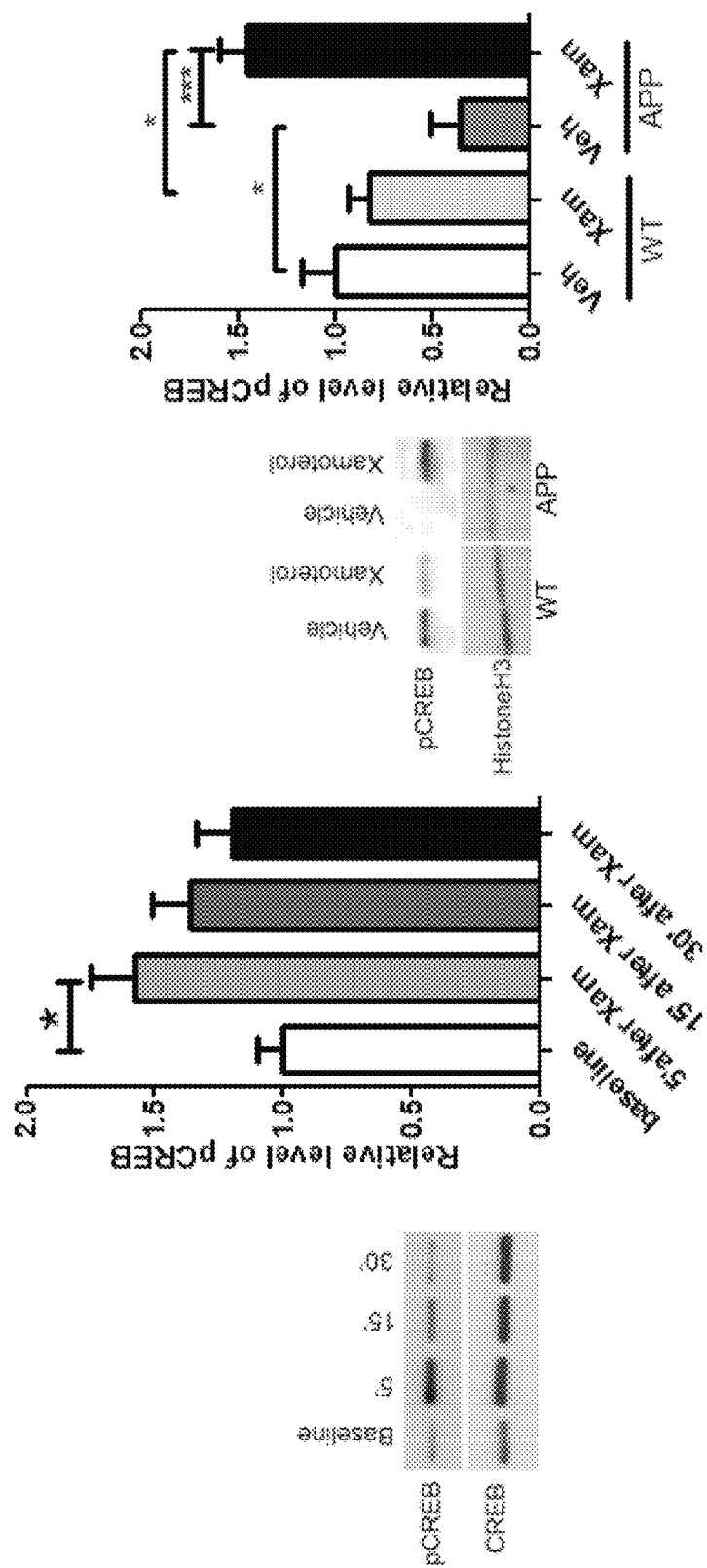
Figures 6A, 6B:
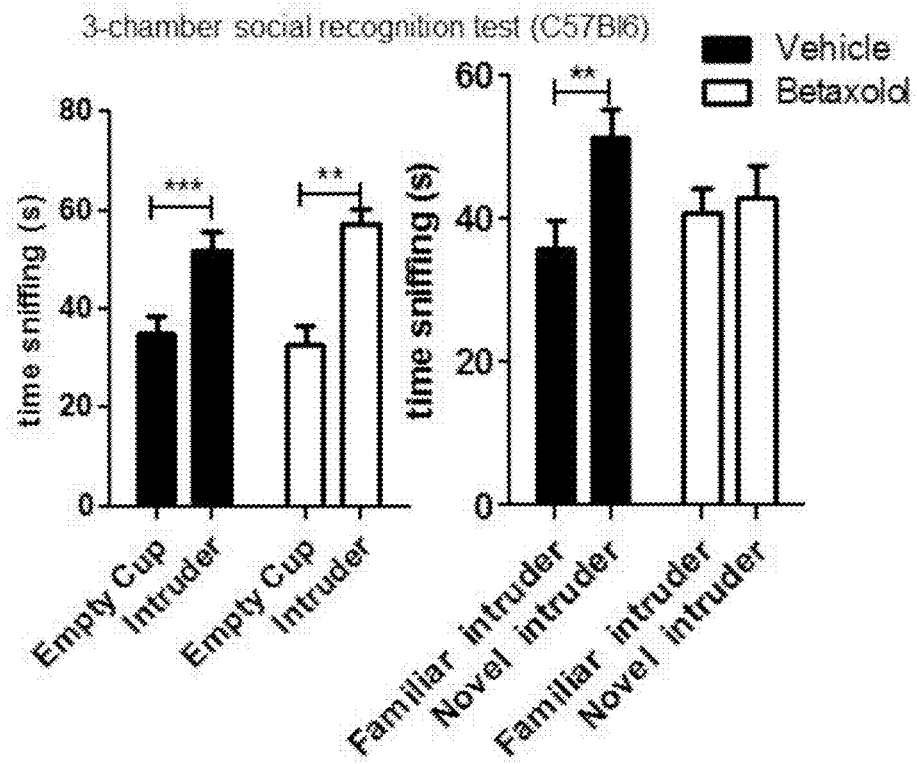
FIG. 6(A)-(D): Blocking the $\beta1$-ADR with betaxolol (1 mg/kg) impaired social recognition independently of non-social odor recognition and object recognition. (A) In the 3-chamber social recognition test, systemic injection of betaxolol prior to the learning phase of the test did not alter the preference of mice for an unfamiliar intruder in a cup over an empty cup (vehicle-τττβinjected mice n=10 *** p=0.0005 by paired t-test; betaxolol-injected mice n=10  p=0.0015 by paired t-test). However, betaxolol impairs social recognition: betaxolol-injected mice did not show a preference for a new intruder over a familiar one (p=0.7127 by paired t-test) while vehicle-injected mice show this preference ( p=0.0082 by paired t-test). (B) Betaxolol did not impair non-social odor recognition: in a test of non-social odor habituation, dishabituation and recognition, both vehicle-injected (n=10) and betaxolol-injected (n=10) mice habituated to non-social odors (water and vanilla) over the course of 3 successive exposures and dishabituated when presented to a new odor (Water habituation: vehicle * p<0.0001; betaxolol ᵀᵀᵀ p<0.001; Water habituation: vehicle  p=0.0011; betaxolol ᵀᵀᵀ p<0.001; Vanilla habituation: vehicle 888 p=0.0001; betaxolol ᵀᵀᵀ p=0.0029). All mice were also able to discriminate between a previously presented odor (vanilla) and a new odor (mint) as indicated by the higher sniffing time when presented with the mint odor versus sniffing time when presented with the vanilla odor for a $3^{rd}$ time (vehicle  p=0.0025; betaxolol ᵀᵀ p=0.0017). (C and D) The ability of mice to recognize a familiar odor or object, respectively, over a new one was not affected by betaxolol. Both vehicle-injected (n=10 * p<0.0001 by paired t-test) and betaxolol-injected (n=10 ** p=0.0015 by paired t-test) mice preferred a new odor or object over a familiar one in an object recognition test. Data are presented as mean±SEM.
Figure 6C:
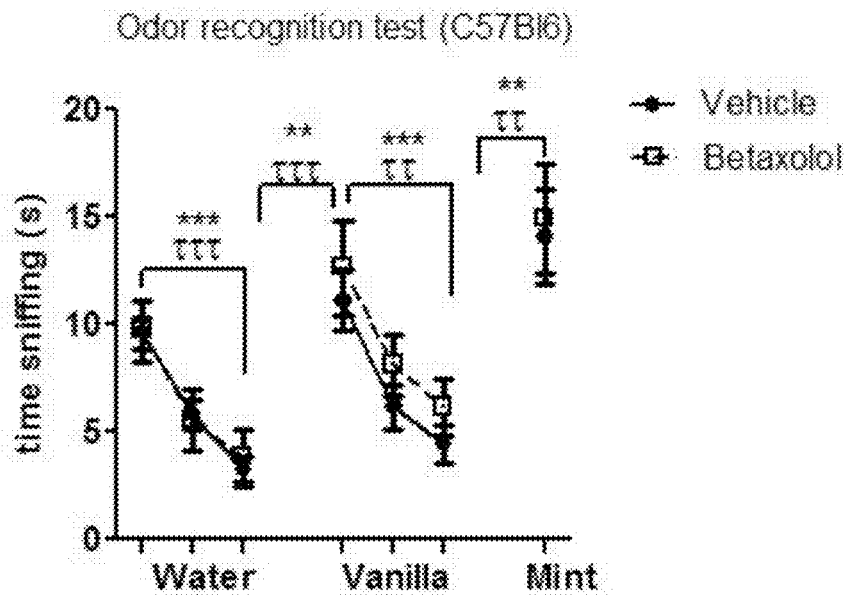
Figure 6D:
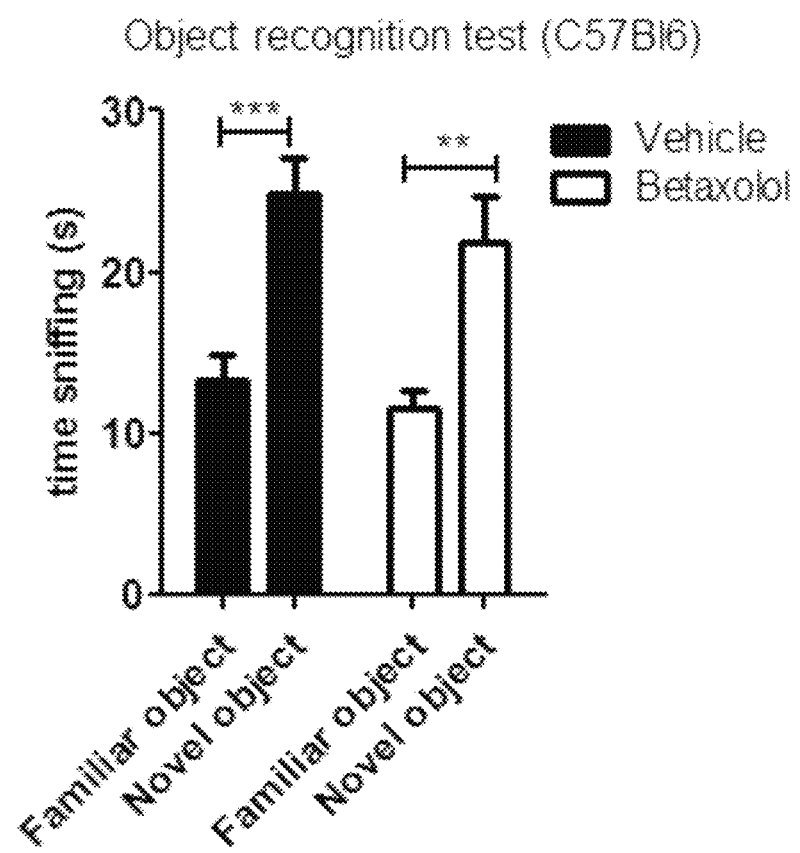

Because one well-known downstream target of PKA is CREB phosphorylation, we aimed at evaluating the possible role of pCREB in social learning; we performed a series of experiments: we first observed that in C57Bl/6 mice learning of social cues induced a strong increase of pCREB in the MeA which picked 5 minutes after the onset of social learning and returned to baseline after 10 minutes (FIG. 5A). We then tested whether pharmacological modulation of $\beta_1$-ADR affects CREB phosphorylation in the MeA in the context of social learning. We showed that blockade of the $\beta_1$-ADR by an acute systemic injection of 1 mg/kg of betaxolol before social learning inhibits the induction of pCREB after social learning (FIG. 5B) while activation of the $\beta_1$-ADR with 3 mg/kg of the partial agonist xamoterol increases pCREB (FIG. 5C). With the present data, we show that activation of the PKA/pCREB cascade downstream of the $\beta_1$-ADR is mediating the social learning and recognition.

To assess whether the rescuing effects of xamoterol on social memory in APP mice is associated with modifications in the level of pCREB, we measured the level of pCREB in the MeA of APP mice and their WT littermates after injection of xamoterol and social learning. As previously found in C57Bl/6 mice (FIG. 5C) xamoterol induced an increase in pCREB after social learning in WT animals. However, there was no significant increase in APP mice. It was reported that in Alzheimer's disease several phosphorylated proteins and transcription factors are preferentially located in the cytoplasm (vs. the nucleus) and are thus inefficient in inducing expression of genes important for learning and memory. We thus determined whether the level of pCREB in the nucleus of APP mice (effective pCREB) was affected by xamoterol. We observed that xamoterol increased pCREB level in the nuclear fraction of the MeA in APP mice (FIG. 5D). This indicates that activation of the $\beta_1$-ADR in a mouse model of AD using the partial agonist xamoterol, leads to improved social recognition, which is associated with an increased level of nuclear pCREB in the MeA.

Many neurological disorders, such as AD, are characterized by deficits in social memory and recognition. The causes of this particular symptom are not yet well defined and as a consequence, no treatment currently exists to rescue this disabling deficit. We have now identified a molecular pathway involved in social learning and recognition and have shown pathological changes in this cascade in the model of AD. We found severe abnormalities in the $\beta_1$-noradrenergic system in the MeA of the Thy1-hAPP$^{Lond/Swe+}$ mice. Specifically, we have identified the $\beta_1$-ADR and it downstream PKA/pCREB signaling cascade as key modulators of social learning and recognition. Moreover, we have shown a selective partial agonist of the $\beta_1$-ADR can restore this selective deficit highlighting a possible approach for improving or restoring social function in AD.

We have reported that Thy1-hAPP$^{Lond/Swe+}$ mice display social recognition deficit, despite demonstrating normal recognition for non-social olfactory cues. Even if at the level of the olfactory bulb, noradrenaline has been shown to be important for the processing of neutral and social olfactory information by promoting selective attention to olfactory stimuli, our results indicate that two independent pathways downstream of the olfactory bulb regulate memory for social and non-social cues. For the first time, we show that the blockade of the $\beta_1$-ADR prior to learning social or neutral olfactory cues leads to impaired social recognition without affecting non-social olfactory recognition. In addition, our results indicate that the $\beta_1$-ADR pathway is necessary for the learning of social cues but not for their recall.

The MeA has been known to be involved in the processing of sensory information necessary for the regulation of social and sexual behaviors in both humans and non-human mammals. While many rodent studies have shown the central role of the MeA for social recognition, our results demonstrate the importance of $\beta_1$-ADR noradrenergic neurotransmission in the MeA for social recognition, and suggest that the abnormal expression of this receptor/signaling cascade in this brain region in Thy1-hAPP$^{Lond/Swe+}$ mice could be responsible for their social recognition deficit.

Our data indicate that the $\beta_1$-ADR in MeA regulates social learning by activation of the PKA/CREB phosphorylation-signaling cascade. Indeed, pharmacological inhibition of PKA in the MeA prior to social learning impairs social recognition. We also demonstrate that blockade of $\beta_1$-ADR with a selective antagonist which induces social recognition deficit results in a severe decrease of CREB phosphorylation in the MeA. These results indicate a direct link between the PKA/pCREB cascade and social learning in mice. Generally it is assumed that pCREB is necessary for long-term memory, rather than short-term memory, because of its known effect on gene expression and protein synthesis that are required for long-term memory. Recently, Suzuki et al demonstrated that an up-regulation of CREB activity leading to higher expression of BDNF enhances social and non-social short-term memory in mice. Here, we are suggesting that a similar phenomenon is occurring as a consequence of activation of the $\beta_1$-ADR. Social learning induces the release of noradrenaline, which activates $\beta_1$-ADR in the MeA, leading to activation of the cAMP/PKA/pCREB signaling cascade. We have shown that activation of $\beta_1$-ADR and its downstream signaling is necessary for the learning of social cues.

While a treatment with the $\beta_1$-ADR partial agonist xamoterol rescues the social recognition deficit of APP mice, it did not affect their total level of pCREB but increased level of nuclear pCREB significantly. We thus suggest that the social recognition deficit observed in APP mice is explained rather by a lack of inappropriate level of nuclear pCREB. It has been shown in cellular system that A$\beta$ causes high level of pCREB and lack of nuclear translocation. We thus suggest that activation of the $\beta_1$-ADR with xamoterol affects the nuclear level of pCREB in the MeA of APP mice and activates mechanisms allowing the processing of social cues necessary for further social recognition.

Our findings indicate that the $\beta_1$-ADR can be used as a therapeutic target to improve the social memory and other cognitive deficits in AD. However, due to significant involvement of noradrenergic system in the cardiovascular function, safety and translational studies may be used to ensure the safety and efficacy of this approach when identifying additional compounds for use in the disclosed threrapies herein. The objective for additional compounds is developing a molecule with minimal systemic activity and high CNS penetration in order to enhance the positive CNS effects of adrenergic system while minimizing the cardiovascular effects.

Identification and Evaluation of $\beta_1$-ADR Prodrugs and Derivatives for Use in Therapies for AD, DS, ADD, ADHD and Autism Given the enhancement of social memory as well as other cognitive deficits in administering the compounds and compositions of the present invention, it is explicitly contemplated that these compounds and compositions may be used to enhance social memory and other cognitive traits in humans exhibiting AD, DS, ADD, ADHD and Autism. Given that NA pathology is known to be linked to multiple pathological features of AD in both human patients and mouse models, one important basis for the present invention is the realization that increasing NA transmission can provide a broader and more effective therapeutic approach than conventional approaches using compounds targeting a single signaling pathway. Specifically, the present invention entails restoring NA signaling through agonistic stimulation of $\beta_1$-ADRs in order to rescue cognitive decline associated with the AD by increasing the level of cAMP response element-binding protein (CREB) phosphorylation and brain-derived neurotrophic factor (BDNF) necessary for the regulation of depolarization in interneurons and downstream modulation of neurotransmission needed for cognitive functions.

Thus, the present inventors provide herein both compounds and compositions for treating AD, DS, ADD, ADHD and Autism, as well as methods of treating these diseases and ameliorating the symptoms thereof.

Guidelines for Selection of Additional Compounds for Use in Treating AD, DS, ADD and ADHD and Autism Other than Those Exemplary Compounds Disclosed Herein The present invention also provides a process and guidelines used in identifying $\beta_1$-ADR agonists (partial or complete) and prodrugs thereof that exhibit minimal or non-existent peripheral effects on cardiac function. The overall process is depicted in FIG. 10. Another overall objective of this process is to identify $\beta_1$-ADR agonists (partial or complete), and prodrugs thereof, and more particularly xamoterol prodrugs, with improved brain distribution and minimal peripheral effects. One result of this procedure is the production of an expanded library of β1-ADR agonist prodrugs that are bioreversible, and in particular xamoterol prodrugs. The following procedure is used to produce the expanded library of $\beta_1$-ADR agonist prodrugs that are bioreversible, i.e., hydrolysable in vivo, and even new, synthetic β1-ADR agonist compounds.

1. Step 1: A candidate β1-ADR agonist prodrug compound is selected based upon estimated favorable c log P value, and subject the compound to a battery of in vitro absorption, distribution, metabolism and excretion (ADME) tests. Compounds selected for this initial testing may be originally designed or may result from a search of the relevant literature. For example, xamoterol prodrugs, such as acylated xamoterol compounds as shown generally in FIGS. 17-19, are prepared using known acylation reactions. The xamoterol prodrugs may be prepared as racemates (racemic mixture) or as (R)- and (S)-enatiomers by enantioselective synthesis.

2) Step 2: A structure-property relationship (SPR) for tested compounds is developed based upon their ADME properties with each of absorption, distribution, metabolism and excretion being determined by known methodologies.

3) Step 3: A compound exhibiting favorable ADME properties from step 2, is advanced to in vivo biodistribution and pharmacokinetic (PK) studies. Two compounds having the most favorable ADME, biodistribution and PK properties are selected for testing in pre-clinical animal model studies.

4) Step 4: Target Product Profiles (TPP) are produced for each compound progressing through Steps 1-3 containing data all in vitro and in vivo data from animal model studies.

5) Step 5: TPPs are then used as a strategic planning tool to guide further drug development.

As noted above, the five steps described above are also shown in FIG. 10.

Xamoterol

Xamoterol is an advantageous and preferred $\beta_1$-ADR lead compound from which various prodrugs are produced. There are several reasons for this. First, results obtained by the present inventors indicate that xamoterol selectively activates a cAMP cascade while maintaining minimal activity on the β-arrestin signaling pathway. See FIG. 9. Among signaling pathways downstream of $\beta_1$-ADR activation, the cAMP signaling casade has been shown to play a key role in synaptic function, neurotransmission and cognitive functions.

Second, since β-arrestin-mediated signaling through activation of the $\beta_1$-ADR is involved in a variety of cardiac processes, it is highly advantageous that xamoterol can specifically target the signaling pathway involved in cognitive function with only minimal actions or effect on cardiac function.

Third, the functional avoidance of β-arrestin signaling activity by xamoterol has the additional advantage of avoiding limitations on agonist therapies by the development of tolerance and tachyphylaxis. Specifically, β-arrestin is involved in receptor desensitization and down-regulation. Increased tolerance occurring in agonist therapies are mediated by β-arrestin signaling dependent receptor desensitization. This problem is greatly minimized by use of xamoterol as a $\beta_1$-ADR lead compound.

Fourth, xamoterol is advantageous given its subtype-selectivity for $\beta_1$-ADR over the closely related receptor $\beta_2$-ADR because β1-ADR is universally coupled to adenylyl cyclase and increases the level of CREB phosphorylation. As such, activation of $\beta_1$-ADR has the ability to rescue CREB-dependent memory deficits. On the other hand, $\beta_2$-ADR can couple to AC inhibiting G protein $G_{i/o}$ and oppose the signaling and cognitive actions of $\beta_1$-ADR. Thus, the subtype selectivity of xamoterol as a lead compound is important. Xamoterol also passes though the blood-brain barrier and reaches the central nervous system where it induces an increase in CREB phosphorylation and mediated pro-cognitive effects. See Table 1 above and FIG. 9. Hence, xamoterol is advantageous as a lead agonist compound for the preparation of numerous xamoterol prodrugs having enhanced properties, such as bioavailability.

Examples of Compound Selections:

The overall objective of the selection procedure steps outlined above is the provision of $\beta_1$-ADR prodrugs, particularly xamoterol prodrugs, having maximized therapeutic usefulness but with minimal systemic or peripheral side effects. The general steps (1-5) described above, will now be described in more detail below:

Step 1: Design and Synthesis of Structural Analogs of β1-ADR Agonist Compounds, Such as Xamoterol, as Prodrugs A focused library of bioreversible derivatives of $\beta_1$-ADR agonist compounds, such as xamoterol, that may be enzymatically or non-enzymatically converted to the lead or agonist compound, such as xamoterol, is generated. In order to improve CNS bioavailability and enhance BBB penetration different strategies may be used and broken into separate studies. Furthermore, it is explicitly recognized that many $\beta_1$-ADR compounds, like xamoterol, are racemic mixtures and may be resolved into their enantiomeric components and separately evaluated as lead compounds as described below. $\beta_1$-ADR racemic mixtures may be resolved using a variety of known methodologies, such as gas chromatography and countercurrent extraction. For example, see EP 0 663 897 (1997). In the alternative, both (R)- and (S)-enatiomeric compounds of xamoterol and xamoterol prodrugs may be enantioselectively synthesized. See also the enantioselective syntheses provided by the present invention below in the Examples in Scheme 1. A procedure is also provided by the present invention for the synthesis of racemic xamoterol and xamoterol prodrugs in the Examples in Scheme 2. These procedures may be used to prepare any of the prodrugs disclosed herein including not only prodrugs of xamoterol, but also of other β1-ADR agonists, such as noradrenalin, isoprenaline or dobutamine, for example.

Further, in the preparation of the structural analogues, reaction progress in analyzed by LCMS, and compounds with less than 90% purity are purified by HPLC. All product compounds are characterized by $^1$H and $^{13}$C NMR. Validated compounds are dissolved in DMSO, and stored as 50 mM DMSO solutions at −25° C.

For example, in study 1 improved lipophilicity of the lead or agonist compound is the objective which is obtained by modifying structures of the lead compound. Inasmuch as xamoterol has poor absorption and low bioavailability (highly hydrophilic with a calculated log P (c log P) value of −0.62), structural analogs are prepared to have improved lipophilicity. In order to do this, enzymatically labile groups, such as esters, carbamates, and oxazolidines, for example, are covalently linked to hydroxyl and/or amino groups of xamoterol. Examples of specific lipophilic prodrugs of xamoterol are shown in FIGS. 17-19. Prodrugs of xamoterol formed by acylation of the terminal phenyl hydroxyl group are particularly advantageous. Below are several schemes illustrating the preparation of xamoterol prodrugs, and, notably, the enantioselective synthesis of R- and S-enantiomers of the xamoterol prodrugs. Also described is the biosensor and protocol used for the cAMP assay.

Method and Synthesis of Xamoterol Enantiomers cAMP Assay

For the cAMP assay, the GloSensor cAMP biosensor (Promega) utilizing a modified form of firefly luciferase containing a cAMP-binding motif was used. Upon cAMP binding, the modified form of GloSensor cAMP biosensor undergoes a conformational change, which leads to enzyme complementation and provide luminescence readout after a luciferase substrate reaction. To quantify the β1-adrenergic receptor (β-ADR)-mediated response, Chinese Hamster Ovary (CHO) cells stably expressing β1-ADR were used. Briefly, cells were plated at a density of $2.0 \times 10^4$ cells per well in clear 94-well culture plates and incubated at 37° C. in 5% $CO_2$ in DMEM/F12 medium supplemented with 10% fetal bovine serum. Twenty-four hour after plating, cells were transfected with pGloSensor™-20F cAMP (Promega) plasmid using Lipofectamine™ 2000 (Invitrogen). Transfected cells were kept in 37° C. in 5% $CO_2$. After 48 hours, cells were incubated in equilibration medium ($CO_2$ independent media, 3% GloSensor™ cAMP reagent) at 37° C. for two hours. After the two hour incubation, test compounds prepared in $CO_2$ independent media were added and changes in luminescence signal were measured for 20 mins from the bottom of the plate using plate reader (FlexStation; Molecular Devices). Functional responses were quantified by calculating the difference between basal luminescence values before the compound addition and the peak luminescence values after the compound addition. Results were expressed as a percentage of 30 uM isoproterenol.

Below are several reaction schemes and associated experimental procedures as non-limiting examples of preparatory procedures for racemic xamoterol and (R)- and (S)-xamoterol.

Examples

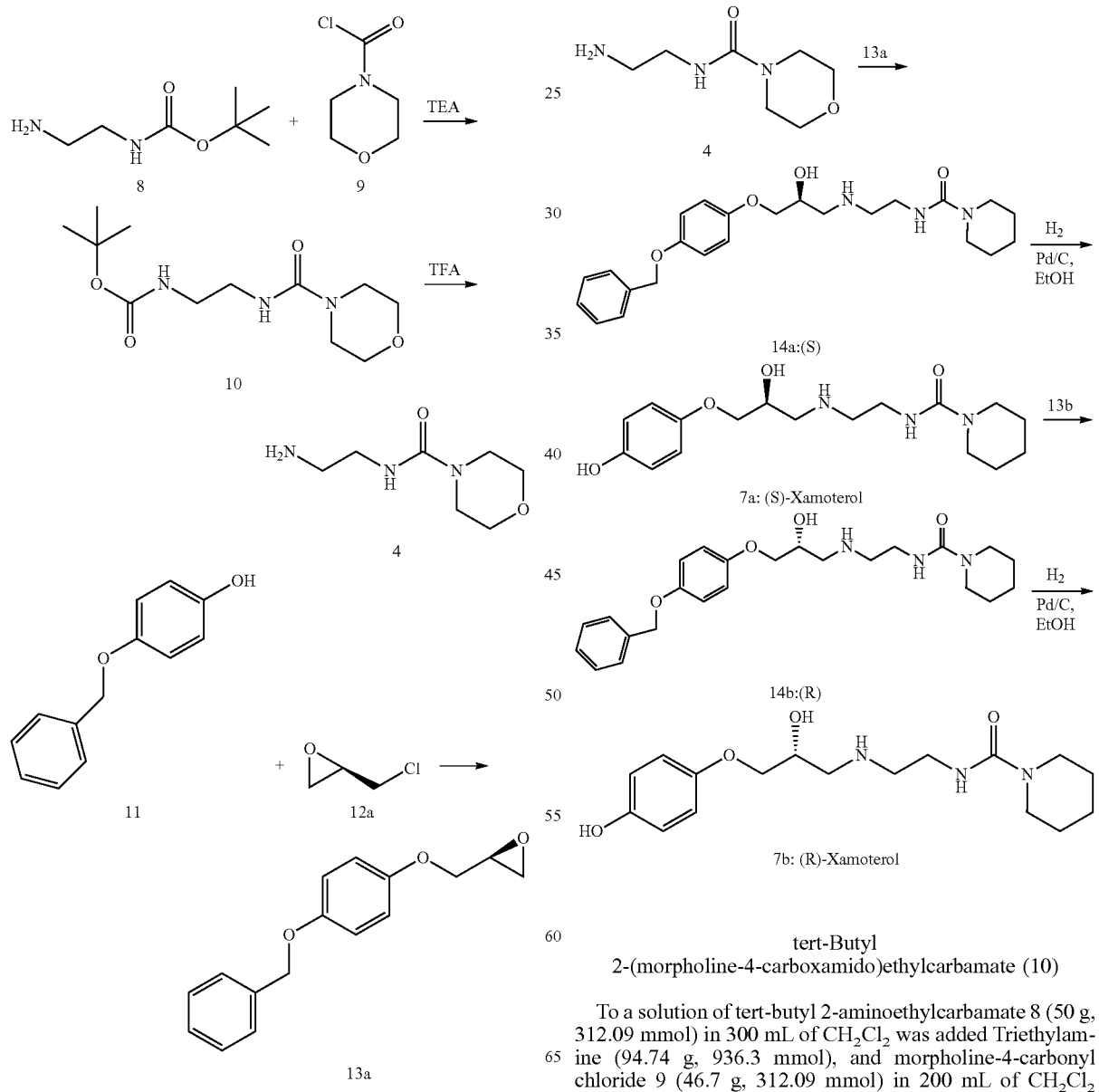

tert-Butyl 2-(morpholine-4-carboxamido)ethylcarbamate (10)

To a solution of tert-butyl 2-aminoethylcarbamate 8 (50 g, 312.09 mmol) in 300 mL of $CH_2Cl_2$ was added Triethylamine (94.74 g, 936.3 mmol), and morpholine-4-carbonyl chloride 9 (46.7 g, 312.09 mmol) in 200 mL of $CH_2Cl_2$ dropwise at 0° C. The reaction mixture was warmed to room temperature and stirred at ambient temperature overnight. The reaction mixture was monitored by TLC. The reaction mixture was then concentrated under reduced pressure and worked up usual. The residue was purified by silica gel column (CH$_2$Cl$_2$:MeOH=10:1) to give tert-butyl 2-(morpholine-4-carboxamido)ethylcarbamate 10 (75 g, 87.9%) as white solid. The 1H NMR was consistent with the structure.

N-(2-aminoethyl) morpholine-4-carboxamide (4)

To a solution of tert-butyl 2-(morpholine-4-carboxamido) ethylcarbamate 3 (75 g, 274.39 mmol) in 500 mL of CH$_2$Cl$_2$ was treated dropwise at 0° C. with TFA (156.0 g, 1.37 mol). The reaction mixture was stirred for 1.5 h. The reaction mixture was then concentrated under reduced pressure, the resulting residue was dissolve in CH$_2$Cl$_2$ and 6M NaOH was added to adjust to pH 8. This mixture was extracted with CH$_2$Cl$_2$ followed by usual work-up to give N-(2-aminoethyl) morpholine-4-carboxamide 4 (43 g, 91%) as a yellow oil. The 1H NMR was consistent with the structure. Some of the free base was converted to 4-(N-beta-aminoethylcarbamoyl)morpholine hydrogen sulfate (mp. 168-169° C.).

(S)-2-((4-(benzyloxy)phenoxy)methyl)oxirane (13a)

A mixture of 4-(benzyloxy)phenol, 11 (50 g, 249.71 mmol) and (R)-2-(chloromethyl)oxirane, 12a (69.31 g, 749.14 mmol) in 500 mL of DMF (was added CsF (113.79 g, 749.14 mmol). The reaction mixture was stirred at 50° C. for 3 days. The resulting reaction mixture was then partitioned between water (1 L) and EtOAc (2 L). The organic layer was washed with 3 times with water (900 mL, each), and brine, and then dried over Na$_2$SO$_4$. The organic extract was concentrated under reduced pressure and purified by silica column (Pet ether:EtOAc, 4:1) to give (S)-2-((4-(benzyloxy)phenoxy)methyl)oxirane, 13a (47 g, 73.4%) as white solid. The 1H NMR was consistent with the structure.

(S)—N-(2-(3-(4-(benzyloxy)phenoxy)-2-hydroxypropylamino)ethyl)morpholine-4-carboxamide (14a)

A mixture of N-(2-aminoethyl)morpholine-4-carboxamide, 4 (30 g, 104.11 mmol) in 120 mL of propan-2-ol was slowly added to a solution of (S)-2-((4-(benzyloxy)phenoxy)methyl)oxirane, 13a (19.72 g, 156.66 mmol) in 230 mL of propan-2-ol below 50° C. over 5 h. The reaction mixture was then cooled to room temperature and thoroughly extracted with EtOAc. The organic layer was washed with water (300 mL), brine, and then dried over Na$_2$SO$_4$. The EtOc extract concentrated under reduced pressure and purified by silica gel column (CH$_2$Cl$_2$:MeOH, 10:1) to give (S)—N-(2-(3-(4-(benzyloxy)phenoxy)-2-hydroxypropylamino)ethyl)morpholine-4-carboxamide, 14a (20.8 g, 63%) as white solid. The 1H NMR was consistent with the structure.

(S)-Xamoterol (7a)

A mixture of (S)—N-(2-(3-(4-(benzyloxy)phenoxy)-2-hydroxypropylamino)ethyl)morpholine-4-carboxamide, 14a (20 g, 46.56 mmol) in 200 mL of EtOH containing 2 mL of acetic acid was added Pd(OH)$_2$/C (5 g). The resulting reaction mixture was subjected to hydrogenation at 55 psi overnight. The catalyst was removed by filtration and the filtrate was concentrated under reduced pressure. The residue was dissolved in EtOH, and converted to hemifumarate with fumaric acid. The hemifumarate salt was recrystallized with EtOH to give (S)-Xamoterol, 7a (12.3 g, 91.7%) as off-white solid. The 1H NMR was consistent with the structure.

(R)-2-((4-(benzyloxy)phenoxy)methyl)oxirane (13b)

This compound was prepared following the procedure as described for 13a from 11 (8 g, 41.9 5 mmol) to give (R)-2-((4-(benzyloxy)phenoxy)methyl)oxirane, 13b (6.3 g, 24.6 mmol, 61%) as white solid.

(R)—N-(2-(3-(4-(benzyloxy)phenoxy)-2-hydroxypropylamino)ethyl)morpholine-4-carboxamide (14b)

The compound 14b was prepared following the procedure described that for the preparation of 14a from 6.3 g, (24.6 mmol) of 7a and (12.77 g (73.80 mmol) of 4 to afford 3 g, (6.98 mmol, 30%) of 14b.

(R)-Xamoterol (7b)

3 g, (6.98 mmol) of 14b was converted to (R)-Xamoterol (7b) following the procedure as described above to give 2.5 g (6.8 mmol, 91%) of 7b as off-white solid as hemifumarate salt.

Scheme 2. Synthesis of racemic Xamoterol:

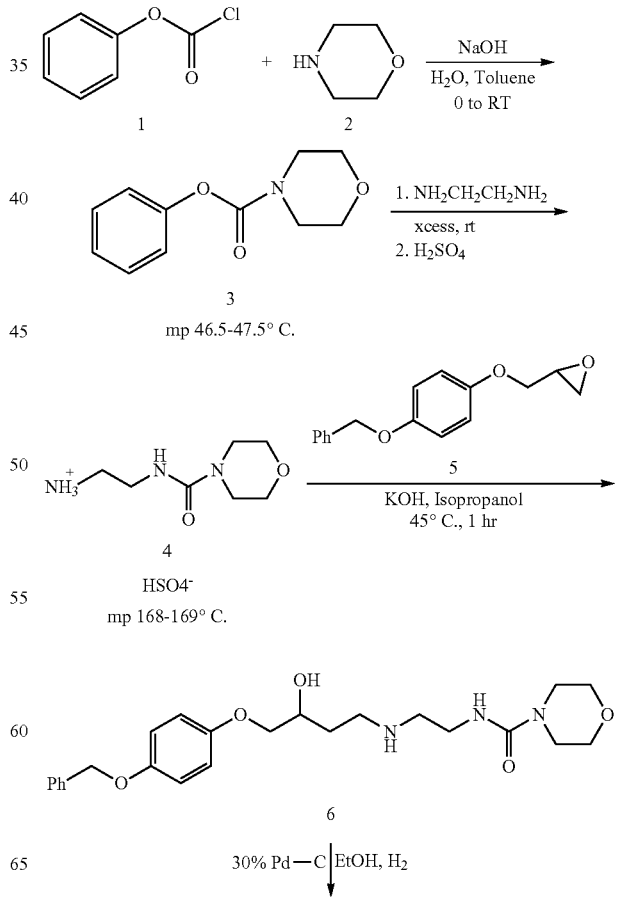

-continued

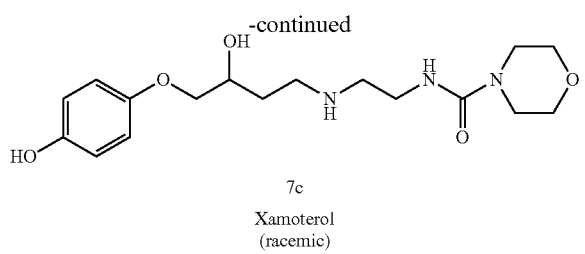

7c

Xamoterol
(racemic)

Preparation of Racemic Xamoterol

N-phenoxycarbonylmorpholine, (3)

Morpholine 2 (4.35 g) and phenyl chloroformate, 1 (6.35 g) are separately and simultaneously added drop wise during 20 min to a stirred mixture of toluene (10 ml), water (5 ml) and sodium hydroxide (2 g) which is maintained at 0° C. The mixture is stirred for a further 2 hours and the temperature is allowed to rise to 20° C. The toluene solution is separated, the aqueous solution is extracted twice with toluene and the combined toluene solutions are washed with water, dried and evaporated to dryness under reduced pressure. The residue is crystallized from petroleum ether (boiling point 60-80° C.) and there is thus obtained N-phenoxycarbonyl-morpholine (3), melting point 46.5-47.5° C.

4-(N-betaaminoethylcarbamoyl) morpholine hydrogen sulfate (4)

A mixture of the above compound 3 (11 g) and ethylene-diamine (27.8 g) is stirred at laboratory temperature for 3 days and the excess of ethylenediamine is removed by evaporation under reduced pressure. The residue is dissolved in methanol, the solution is cooled to 5° C. and concentrated sulfuric acid is added until the pH of the solution is 2. A filter-aid (Celite, 10 g) is added and the mixture is stirred for 1 hour and then filtered. The filtrate is evaporated to dryness under reduced pressure and the residue is stirred with ethyl acetate. The mixture is filtered and there is thus obtained as solid residue 4-(N-beta-aminoeth-ylcarbamoyl)morpholine hydrogen sulfate (4), melting point 168-169° C.

1-p-benzyloxyphenoxy-3-(beta-morpholinocarbona-midoethyl)amino-2-propanol hydrochloride (6)

A suspension of 1-p-benzyloxyphenoxy-2,3-epoxypro-pane 5 (11.5 g) in isopropanol (6 ml) is added to a stirred mixture of 4-(N-betaaminoethylcarbamoyl) morpholine hydrogen sulfate 4 (12.7 g), potassium hydroxide (7.0 g) and isopropanol (10 ml) and the mixture is stirred at 45° C. for 1 hour and then evaporated to dryness under reduced pressure. The residual oil is stirred with water, the mixture is filtered and the solid residue is dissolved in acetone. A 30% solution of hydrogen chloride in propanol is added until the pH of the mixture is less than 2, and the mixture is filtered.

The solid residue is crystallized from water and there is thus obtained 1-p-benzyloxyphenoxy-3-(beta-mor-pholinocarbonamidoethyl)amino-2-propanol hydrochloride 6 (4.9 g).

Xamoterol (7c): (1-p-Hydroxyphenoxy-3-beta-(mor-pholinocarbonamido)ethyl-amino-2-propanol hydrogen fumarate)

A solution of the above compound 6 in a mixture of ethanol (20 ml) and acetic acid (20 ml) is shaken with a 30% palladium-on-charcoal catalyst (0.1 g) in an atmosphere of hydrogen at laboratory temperature and pressure until 250 ml of hydrogen is absorbed. The mixture is filtered, the filtrate is evaporated to dryness under reduced pressure and to the residue is added a hot solution of fumaric acid (1.25 g) in ethanol (15 ml). The mixture is kept at 5° C. for 12 hours and is then filtered, and the solid residue is washed with hot ethanol and then dried. There is thus obtained 1-p-hydroxyphenoxy-3-beta-(morpholinocarbonamido) ethyl-amino-2-propanol hydrogen fumarate (7c), m.p.168-169° C. (with decomposition). See U.S. Pat. No. 4,143,140, which is incorporated herein by reference in the entirety.

In study 2, specific carriers in the brain microvessels are targeted to improve CNS bioavailability of the lead compound. This strategy has the objective of enhancing drug delivery to the brain while reducing exposure and toxicity to other peripheral organs. Specifically, endogenous carriers or transporters expressed on the BBB, such as GLUT-1, LAT-1 and choline transporter, are used in order to conjugate xamoterol, for example, with substrates for the carriers or transporters to deliver the drug specifically to the brain. Examples of targeted prodrugs of xamoterol are shown in FIG. 17.

In study 3, enatiomeric separation of racemic prodrug compounds is effected in order to evaluate the properties of the enatiomeric prodrugs. As noted above, resolution of β1-ADR racemic lead or prodrug compound mixtures into enatiomers may be effected by any known procedure, such as gas chromatography, countercurrent extraction, and also chiral resolution using Mosher's esterification using α-methoxy-α-trifluoromethyl-phenylacetic acid. See Mosher et al., Journal of Organic Chemistry 34(9):2543-2549 (1969).

In fact, the present inventors have discovered that the R- and S-enantiomers of xamoterol exhibit substantially different pharmacological activities. For example, FIG. 23 evidences that xamoterol racemate (R,S) and the (S)-enantiomer stimulated cAMP accumulation with similar potencies with EC50 values in the nanomolar range, i.e., (R,S)-xamoterol, $EC_{50}$=11.6 nM; and (S-)-xamoterol, $EC_{50}$=21.2 nM. In contrast, (R)-xamoterol stimulated cAMP accumulation with an $EC_{50}$ of 11900 nM. This indicates that (S)-xamoterol is about 500 fold more potent than (R)-xamoterol in stimulating cAMP accumulation through β1-ADR. However, the present invention provides enantioselective methods of producing (R)- and (S)-enatiomers of xamoterol prodrugs, but also such enantiomers of β1-ADR agonists, generally, such as noradrenalin, isoprenaline and dobutamine.

Step 2: Select Prodrug Compounds Having Favorable Pharmacokinetic Properties and Improved CNS Bioavailability The compound prodrugs selected in this step must generally exhibit stability in biological media or tissue before reaching the brain, favorable physicochemical properties for either transcellular permeation across the BBB or have structures that are recognized by receptors or transporters expressed in the BBB for active transport, and be readily converted back to the parent or lead compound. C57B1/6 mice are used for in vivo PK studies due to the similarity in xamoterol metabolism between humans and mice.

In study 1, biostabilities of β$_1$-ADR prodrug compounds, such as xamoterol analogs, and their in vitro conversion to the parent drug are assessed. For example, xamoterol analogs are Incubated with mice blood, liver S9 fraction, brain homogenates and isotonic phosphate buffer at 37° C. in a shaker water bath. Aliquots of 100 µl are withdrawn at time zero and every 30 minutes for up to 3 hours after the drug addition. The collected samples are immediately centrifuged and supernatants are carefully removed and stored at −80° C. until analysis. LC-MS/MS analysis is performed to determine the amount of intact prodrug and xamoterol, for example, in the supernatant. Metabolic half-life and bioconversion is also determined.

In study 2, CNS penetration of β1-ADR agonist prodrugs, such as xamoterol analogs, are assessed using a noncontact co-culture model, which shows many features of the BBB including low paracellular permeation, well-developed tight junctions, and expression of efflux transporters. Human brain microvascular endothelial cells (HBMEC) and human astrocytes (HA) are co-cultured using transwell plates with a microporous semi-permeable membrane. HBMEC is seeded onto fibronectin-coated translucent membrane inserts and allowed to establish a polarized monolayer for 3-4 days. The formed layer of endothelial cells separate the system into an apical and basolateral compartment, allowing administration and sampling of test compounds on either side of the model. HA is seeded on the bottom of the carrier plates. On the day of the actual experiment, all medium is removed and the inserts are relocated to a new 24-well plate containing phosphate-buffered saline. The test compounds are dissolved in DMSO and added to the donor compartment at a concentration of 1 μM. To determine the rate of compound appearance on the recipient side, samples are collected from the recipient side at 5, 15, 30, 60, 90 and 120 minutes after drug addition. To maintain a constant volume across the chambers, an equivalent amount of phosphate-buffered saline is added to the recipient chamber after each sampling. The collected samples are analyzed by LC/MS/MS. Apparent apical to basal permeability ($P_{app}$ AB), apparent basal to apical ($P_{app}$ BA), and efflux ration ($P_{app}$ BA/$P_{app}$ AB) is determined. Each drug or drug prodrug tested is tested across a minimum of four different membranes at multiple time points for each membrane.

In study 3, prodrugs, such as xamoterol analogs, that exhibit promising physicochemical properties in in vitro studies are advanced to the in vivo PK studies. For example, xamoterol is administered to C57Bl/6 mice as a single dose of 3 mg/kg either intravenously or subcutaneously. For prodrugs, doses equivalent to 3 mg/kg of xamoterol are administered. Mice are euthanized at 3, 15, 30, 60, 120, 240 and 360 minutes after drug administration. Blood is drawn by cardiac puncture and collected in heparinized tubes. Plasma is immediately separated by centrifugation and stored at −80° C. until assay. For tissue distribution studies, tissue samples from the brain, heart, kidney, liver and spleen are collected 60 and 120 minutes after drug administration. The tissue samples are homogenized using 0.9% saline at a ratio of 1:2. The homogenates are stored at −80° C. until analysis. Concentrations of xamoterol from plasma and tissue samples are analyzed by LC-MS/MS using a known method. See Faizi, et al. Brain Behavior, 2012. 2(2): p. 142-154. Concentrations of xamoterol and its analogs in plasma brain are analyzed by non-comppartmental methods to determine pharmacokinetic parameters. PK parameters of prodrugs including maximum plasma concentration ($C_{max}$), time to maximum concentration ($T_{max}$) and area under curve (AUC) are determined and compared to those of xamoterol. These results afford a BBB permeability index for xamoterol analogs.

Statistical Analysis

All compounds (lead and prodrug/analog compounds) are screened using the in vitro biostability, bioconversion and BBB permeation tests. Only compounds showing potential to exhibit improved CNS bioavailability undergo in vivo PK studies. PK data analysis is effected using WinNonlin software. Student's t-test is used to detect statistical significance between the parameters of the prodrugs and the parent or lead drug using the Prism 3.0 program (Graph Pad Software). Differences are considered to be significant at a level of $p<0.05$.

Step 3: Evaluation of the Effects of Prodrugs on Cognitive Symptoms

In this step, the Thy1-APP$^{Lond/Swe+}$ mouse model of AD is used, which mouse model presents cognitive deficits, mature β-amyloid plaques as well as synaptic degeneration. Thy1-App$^{Lond/Swe+}$ mice are treated with a chronic dosing of xamoterol and at least two prodrugs for four months starting at 6 months of age using osmotic pumps implanted under the skin. FIG. 20 illustrates a scheme with studies 1 and 2 described below.

In study 1, the effects of chronic treatment with xamoterol and prodrugs thereof on the cognitive effects of the mice are tested. This study entails a study of the effects of β$_1$-ADR agonists, such as xamoterol, and prodrugs thereof on working memory (using the Y-maze test), social memory (using the social novelty test) and contextual memory (using the fear conditioning test). The Thy1-APP$^{Lond/Swe+}$ mice exhibit impaired working memory (Y-maze test), social recognition and contextual memory (fear conditioning test) at 6 months age, and are a mouse model of AD. Specifically, chronic treatment with β1-ADR agonists, such as xamoterol, and their prodrugs are tested to assess the effect of each in rescuing cognitive deficits observed in the mouse model for AD. These specific mice and non-Tg (non-transgenic) mice are aged to 6 months and then tested in the three behavioral tests indicated both above and in FIG. 20. After behavioral testing, mice are sacrificed and brain tissue is harvested for study. The values obtained are used as a baseline. Other cohorts of mice receive β$_1$-ADR agonist prodrugs, including xamoterol prodrugs, using s.c osmotic pumps. These cohorts are tested in the 3 cognitive tasks specified at 2 months (mice 8 months old) and 4 months (mice 10 months old) after the beginning of dosing. 12 mice (n=12) per genotype are used, per treatment and per time point. After behavioral testing, mice are sacrificed for brain tissue analysis in study 2 below. Brains are cut sagitally, and half the brain is frozen at −80° C. until use, and other half is placed overnight in 4% para-formaldehyde (PFA) and kept at 4° C. in sucrose until processed.

In study 2, the results of chronic treatment with β1-ADR agonists, including xamoterol, and prodrugs thereof are tested to determine which compounds decrease pathological changes that are associated with AD. (The Thy1-App$^{Lond/Swe+}$ mouse model of AD presents synaptic structural abnormalities and high levels of Aβ42 and of plaque numbers) This study evaluates the extent to which tested prodrugs ameliorate pathological alterations in synaptic structures shown in the mouse model of AD. Further, sandwich ELISA is performed for the presynaptic vesicular protein, synaptophysin, the presynaptic membrane protein SNPA-25 (25 kDa synaptosome-associated protein), and the postsynaptic scaffolding protein PSD-95 (postsynaptic density 95). The reduction in plaque level is also assessed, and quantification of Aβ40 and Aβ42 are performed by ELISA. Immunohistochemical tests are also performed on sagital brain sections using an anti-Aβ antibody and analysis of plaque size, number and load in different brain regions is also performed using ImageJ software.

Also, based on the involvement of NA in migration and phagocytic activity of microglia, it is also determined whether chronic treatment with various β1-ADR agonist prodrugs, including xamoterol prodrugs, affect neuroinflammatory processes.

Microglia activation is also quantified using immunohistochemistry with 1bal-antibody and unbiased stereological counting. Neuroinflammatory mediators such as TNF-α and Interleukin-1(IL-1) ad 6(IL-6) are evaluated by ELISA. 6 to 8 animals/group treatment are analyzed.

In Vivo Statistical Analysis

All in vivo efficacy studies are conducted by experimenters blind to both the genotypes and the treatments to assure reliability of the results. All data are tested for normality with the Shapiro-Wilk test and appropriate parametric or non-parametric tests will be used for intergroup comparisons. All data is analyzed using an ANOVA (parametric) or Kruskal-Wallis test (non-parametric) followed by post-hoc analysis. All analyses are done using Prism software.

The present invention thus provides several inventive aspects, which are all part and parcel of the same invention.

First, the present invention provides bioreversible $β_1$-ADR agonist prodrugs, which agonistic-ally stimulate $β_1$-ADR, after bioconversion to the parent drug, and which have improved lipophilicity and CNS bioavailability as compared to the corresponding β1-ADR agonist. Preferably, the bioreversible β1-ADR agonist prodrugs also stimulate the cAMP pathway more than they stimulate the β-arrestin pathway following bioconversion to the corresponding β1-ADR agonists. Specifically, it is most preferred if the $β_1$-ADR agonist prodrug compounds stimulate the β-arrestin pathway at no more than 50% than they stimulate the cAMP pathway at the same concentration in the range of $10^{-4}$ to $10^{-10}$ M after bioconversion. It is even more preferred that the β-arrestin pathway is stimulated at no more than 20%, and most preferably if there is no stimulation of the β-arrestin pathway at all.

It is also preferred that the bioreversible β1-ADR agonist prodrug stimulate a downstream CREB pathway following bioconversion.

These compounds may be formulated as compositions in injectable form. For example, the compounds may be dissolved in sterile saline solution or dextrose saline solution. Thus, the solutions may be injected intravenously (i.v.) or subcutaneously (s.c.). However, the present β1-ADR prodrugs may be administered by any means of administration, such as by inhalation either by nose drops, nose swab or dry powder inhaler or intranasal delivery generally or even orally.

Second, the present invention provides a method of treating DS in a human, which entails administering one or more $β_1$-ADR agonist prodrugs as described above in an amount effective to improve cognition, including social memory.

Third, the present invention provides a method of treating AD in a human, which entails administering one or more $β_1$-ADR agonist prodrugs as described above in an amount effective to improve cognition, including social memory.

Fourth, the present invention provides a method of treating autism in a human, which entails administering one or more β1-ADR agonist prodrugs as described above in an amount effective to improve cognition, including social memory.

The compounds and compositions of the present invention may be used advantageously in the treatment of AD, DS, ADD, ADHD and autism. All of these disease or conditions benefit from an improvement in cognition, including social memory.

Fifth, the present invention also provides a method of selecting a $β_1$-ADR agonist prodrug for therapeutic use, which entails:

a) selecting one or more prodrug compounds having an enhanced c log P value relative to the corresponding β1-ADR agonist compound;

b) subjecting the selected prodrug compounds from step a) to a battery of ADME tests, and determining SPR for the prodrug compounds;

c) selecting one or more prodrug compounds from step b) and subjecting said prodrug compounds to in vivo biodistribution and pharmacokinetic (PK) evaluation;

d) selecting one or more prodrug compounds from step c) for pre-clinical animal model studies; and e) producing a TPP for each prodrug compound selected from all of steps a)-d), for further development for therapeutic use.

Synthesis of $β_1$-ADR Prodrugs

Generally, the $β_1$-ADR prodrugs of the present invention are selected having c log P values of at least 0, and preferably >1.0. It is more preferred, however, that the prodrugs have a c log P value of >2.0 and higher, such as 3.0-5.0, for example.

The $β_1$-ADR prodrugs of the present invention are prepared by forming ester compounds from substituent hydroxyl groups and/or amide groups from substituent amine groups of the corresponding $β_1$-ADR parent or lead compound. For example, esters and/or amides of xamoterol are formed by esterifying hydroxyl groups of xamoterol, and amides of xamoterol are formed by amidizing amine groups of xamoterol. Well known chemical reactions may be used to prepare both esters and amides of the $β_1$-ADR compounds to form the corresponding $β_1$-ADR prodrugs. Moreover, one or more hydroxyl groups on the $β_1$-ADR compounds may be esterified, and/or one or more amine groups on the $β_1$-ADR compounds may be amidized. Xamoterol, for example, has two free hydroxyl groups and two internal free amino groups (—NH—). Generally, it is advantageous to esterify either the terminal phenyl hydroxy group or secondary hydroxy group or both of xamoterol. The more preferred method of esterification is acylation.

That is, for any β1-ADR agonist compound, one or more free hydroxyl groups thereon are derivatized by forming esters of the general formula: —O—(C=O)—R.

An exemplary synthetic scheme for the preparation of prodrugs is shown below:

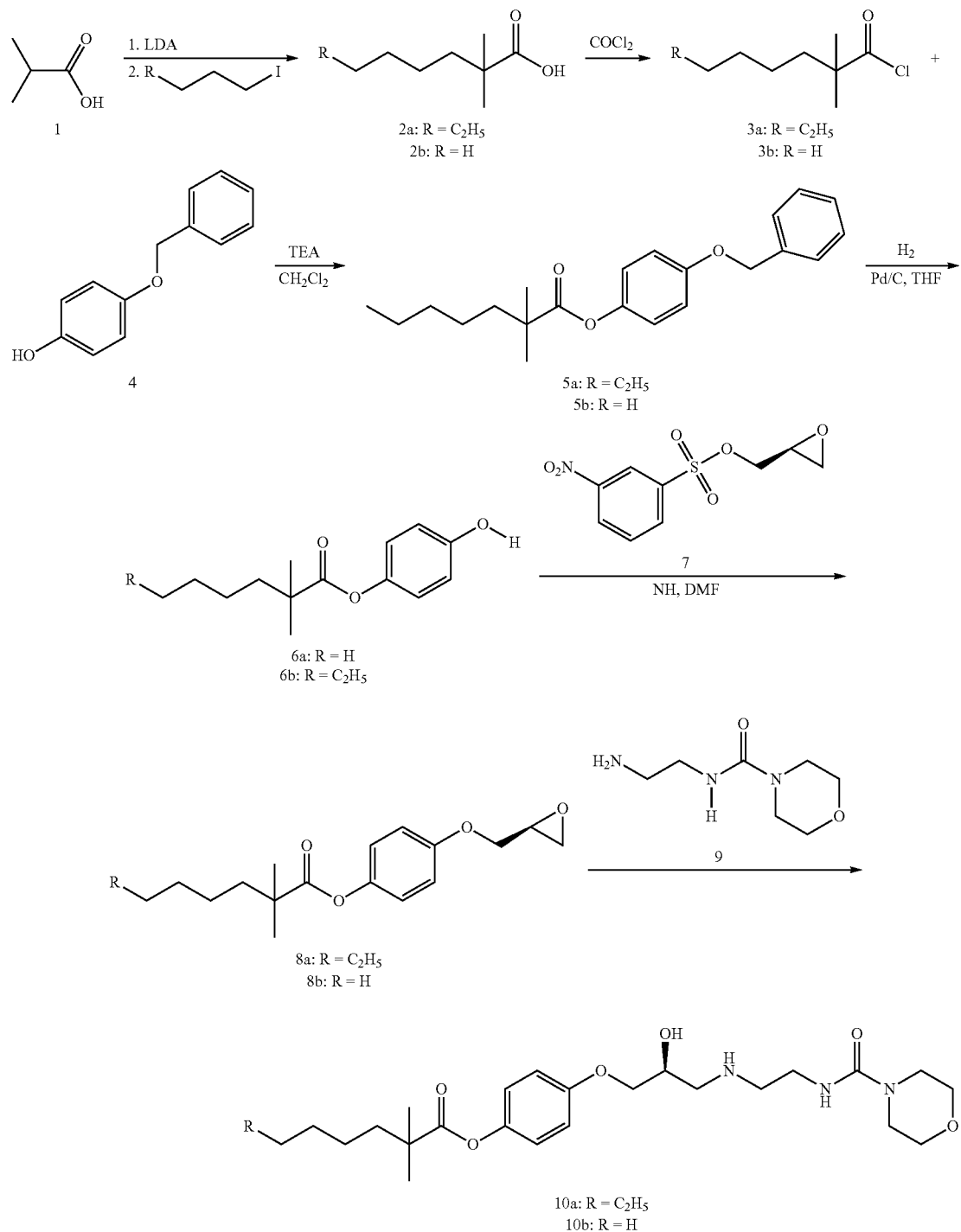

Scheme 3. Synthesis of Phenoxy ester prodrugs of (S)-Xamoterol

Note: Compound 7 in the above scheme is the (S)-enantiomer, i.e., (S)-oxiran-2-ylmethyl 3-nitrobenzenesulfonate.

2,2-Dimethyloctanoic Acid (2a)

Isobutyric acid (2.0 g, 22.7 mmol) was added dropwise to a solution of LDA (7.6 mL) under nitrogen atmosphere at 0° C. The solution was allowed to stir for 15 minutes. 1-Iodo-hexane (4.8 g, 22.7 mmol) was added dropwise to the solution at this temperature and the resulting mixture was allowed to stir for 2 hours at room temperature. The reaction mixture was then treated with 50 mL of water and adjusted to $P_H$~3 with 3 N HCl. The resulting mixture was extracted several times with ethyl acetate. The organic layer separated, dried and evaporated under reduced pressure to afford 2,2-dimethyloctanoic acid (2.48 g, 63.4%) as colourless oil which be used without further purification.

2,2-Dimethylhexanoic Acid (2b)

2,2-Dimethylhexanoic acid (2a) was prepared using procedure as described above to give (2 g, 13.87 mmol, 61%) as colorless oil.

4-(benzyloxy)phenyl 2,2-dimethyloctanoate (5a)

To a solution of 2,2-dimethyloctanoic acid, 2a (2.48 g, 14.4 mmol) in dichloromethane (15 mL) was added oxalyl chloride (3.66 g, 28.8 mmol) dropwise at 0° C. The resulting solution was stirred under nitrogen atmosphere for 2 hours. The resulting mixture was evaporated under reduced pressure to afford 2,2-dimethyloctanoyl chloride (3a) as an unstable intermediate which was used without further purification. Triethylamine (2.91 g, 28.76 mmol) was added dropwise to the solution of 2,2-dimethyloctanoyl chloride (3a) obtained above and then treated with a solution of 4-(benzyloxy)phenol, 4 (3.2 g, 15.98 mmol) in 15 mL of dichloromethane at 0° C. Few drop of Dimethylformamide were added to the solution. After the addition, the resulting solution was allowed to stir for 15 hours at room temperature. The reaction mixture was concentrated under reduced pressure and the residue was thoroughly extracted with dichloromethane. The organic layer was washed with water (150 mL), brine, dried and concentrated under reduced pressure. The residue was purified using flash chromatography (petroleum ether:ethyl acetate=10:1) to afford 4-(benzyloxy)phenyl 2,2-dimethyloctanoate, 5a (2.49 g, 49%) as colourless oil.

4-(benzyloxy)phenyl 2,2-dimethylhexanoate (5b)

2.25 g, of 4-(benzyloxy)phenyl 2,2-dimethylhexanoate (5b) was prepared using the procedure described above that for 5a.

4-hydroxyphenyl 2,2-dimethyloctanoate (6a)

4-(benzyloxy)phenyl 2,2-dimethyloctanoate, 5a (2.49 g, 7.02 mmol) and Pd/C (500 mg) were stirred in THF (100 mL) under hydrogen for 15 hours. The mixture was filtered through a pad of Celite. The filtrate was concentrated under reduced pressure. The residue was purified using flash chromatography (petroleum ether:ethyl acetate=10:1) to afford 4-hydroxyphenyl 2,2-dimethyloctanoate, 6a (1.86 g, 100%) as white solid.

4-hydroxyphenyl 2,2-dimethylheaanoate (6b)

4-hydroxyphenyl 2,2-dimethylhexanoate (6b), 3 g (12.7 mmol, 99%) was prepared from 4 g of 5b using procedure described above and was used as such in the next step.

(S)-4-(oxiran-2-ylmethoxy)phenyl 2,2-dimethyloctanoate (8a)

To a solution of 4-hydroxyphenyl 2,2-dimethyloctanoate, 6a (3.2 g, 12.1 mmol) in dimethylformamide (30 mL) was added NaH (0.32 g, 13.3 mmol) portionwise under nitrogen atmosphere. The mixture was stirred at room temperature for 1 hour then (S)-oxiran-2-ylmethyl 3-nitrobenzenesulfonate, 7 (3.45 g, 13.3 mmol) was added to the solution. The resulting mixture was allowed to stir at room temperature for 15 hours then diluted with 100 mL of water and thoroughly extracted with dichloromethane. The organic layer was washed with water, brine then dried and concentrated under reduced pressure. The residue was purified using flash chromatography (petroleum ether:ethyl acetate=5:1) to give (S)-4-(oxiran-2-ylmethoxy)phenyl 2,2-dimethyloctanoate, 8a (3.04 g, 78%) as colourless oil.

(S)-4-(oxiran-2-ylmethoxy)phenyl 2,2-dimethylhexanoate (8b)

(S)-4-(oxiran-2-ylmethoxy)phenyl 2,2-dimethylhexanoate (8b), 2 g (6.84 mmol, 54%) was prepared as white solid from 3 g of 6b using procedure described above.

2,2-dimethyloctanoate ester of (S)-Xamoterol (10a)

(S)-4-(oxiran-2-ylmethoxy)phenyl-2,2-dimethyloctanoate, 8a (3.07 g, 9.6 mmol) and N-(2-aminoethyl)morpholine-4-carboxamide, 9 (4.98 g, 28.8 mmol) were stirred in isopropyl alcohol (100 mL) at 50° C. for 15 hours. The mixture was concentrated under reduced pressure. The residue was diluted with dichloromethane (100 mL) and washed with water (100 mL). The organic layer was evaporated under reduced pressure. The residue was purified using flash chromatography (petroleum ether:ethyl acetate=10:1) to give 2,2-dimethyloctanoate ester of (S)-Xamoterol, 10a (2.1 g, 44%) as colourless oil. The 1H NMR was consistent with the structure.

Fumaric acid (0.18 g, 1.52 mmol) in ethanol (15 mL) was added to a stirred solution of 10a (1.5 g, 3.04 mmol) in ethanol (15 mL) dropwise. The resulting solution was allowed to stirred at room temperature for 5 hours. The mixture was filtered under reduced pressure. The precipitate was washed with ethanol (10 mL) and dried under reduced pressure. The residue was dissolved in distilled water (10 mL) and dried under vacuum at −78° C. to remove the ethanol residue. Hemifumarate salt of 10a was obtained (1.08 g, 64%) as white solid.

2,2-dimethylhextanoate Ester of (S)-Xamoterol (10b)

This compound 10b, was prepared following the procedure described above for 10a, and converted to hemifumarate salt to give 0.995 g, (1.90 mmol, 28%) of desired product.

Additionally, hydrolytically-degradable carbamate derivatives for amines may be used as described in U.S. Pat. Nos. 5,466,811 and 7,988,956, both of which are incorporated herein in the entirety. Specifically, U.S. Pat. No. 5,466,811 discloses the use of oxodioxolenylmethyl carbamates to produce bioreversible neutral prodrugs from both primary and secondary amines.

Generally, any derivatization of either or both of hydroxyl and/or amine groups of the β1-ADR agonist compounds is acceptable provided that the c log P value of the prodrug produced is greater than 0, and preferably greater than 1.0, and most preferably greater than 2.0. However, as noted above, it is particularly advantageous to use xamoterol prodrugs having an acylated terminal phenyl hydroxyl group. Such compounds have the general formula shown in the lower structural formula of FIG. 17.

Further, the $R_1$ moiety of the $R_1$—(C═O)—O— group and/or the $R_2$ moiety of the R2-(C═O)—O— group (as positionally noted in FIG. 17) are each a lipophilic group of from 5 to 30 carbon atoms, which may be linear, branched or cyclic groups which may be unsubstituted or optionally substituted with lower alkyl, lower alkoxy or halo, preferably fluoro. As used in this application, the term "lower"

means $C_1$-$C_6$. However, cyclic compounds may also be encompassed in the lipophilic group of 5 to 30 carbon atoms, such as a phenyl ring which may be optionally substituted as shown in FIG. 19 (top figure) or a heterocyclic ring such as also shown in FIG. 19 (lower figure). It is preferred that the $R_1$ and/or $R_2$ moiety of the primary or main chain of the acyl group be from 8, 9 or 10 to 30 carbon atoms. The range of the number of primary or main carbon atoms does not include any side chains of carbon atoms. The term "primary or main chain" versus "side chain" is determined herein by standard IUPAC naming nomenclature. Thus, for example, in 2-methyl pentane, the primary or main chain is pentane ($C_5$) and the side chain is methyl ($C_1$).

The cyclic compounds of the $R_1$ and/or $R_2$ moieties may generally be 5- or 6-membered rings containing no heratoms or having 1 or 2 heteroatoms, such as —O— or —N—. Further, the rings containing no heteroatoms may be either saturated or unsaturated and even aromatic. The heteroatoms may also be —O— or —N—. Exemplary ring systems include, for example, pyrrole, furan, imidizoline, imidazole, pyrazolidine, pyrazole, pyridine or pyran, which are unsubstituted or optionally substituted by 1-4 lower alkyl, lower alkoxy, hydroxyl or halo groups, particularly fluoro. All such compounds may be synthesized by well known procedures involving the acylation of the terminal phenyl hydroxy group by reference to Scheme 1 and 2 above using an appropriate acylating compound to prepare the desired corresponding acylated xamoterol prodrug.

By reference to Scheme 3 above, it may be seen that any lipophilic acyl group may be attached to xamoterol using an analogous reaction to compound 2>compound 3>compound 5>compound 6>compound 8 and finally compound 10. That is Scheme 3 may be generally used to convert:

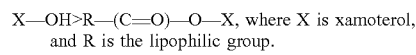

X—OH>R—(C=O)—O—X, where X is xamoterol, and R is the lipophilic group.

Note: In the above simplified reaction, a generic R is used rather than a specific $R_1$ and/or $R_2$, but the mechanism shown fairly represents both.

Known esterification reactions to esterify generally, and acylate, specifically, the secondary hydroxy group of xamoterol, for example, may be used to form the group R2-(C=O)—O— shown in FIG. 17. For example see U.S. Pat. Nos. 3,278,585 and 8,669,311, both of which are incorporated herein in the entirety.

Analogously, the reactions described above in Schemes 1, 2 and 3 may be used to prepare prodrugs of other β1-ADR agonists.

Specific examples of lipophilic R groups corresponding to the formula 10 in Scheme 3 where instead the R group is attached directly to the xamoterol molecule as R—(C=O)—O—X, are as follows:

R may be unsubstituted or optionally substituted linear or branched alkyl, which is $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ or $C_{30}$, or each of these same $C_5$-$C_{30}$ alkyl groups may be unsubstituted or optionally substituted branched or cyclic groups, such as cyclopentyl or cyclohexyl, or with a combination of linear, branched or cyclic groups. Further, these linear, branched or cyclic groups may have one or more intervening —O— or —N— groups in the primary or main chain linking the xamoterol molecule with a ring system, such as phenyl or pyranyl, for example.

Further, compounds having both R1 and R2 groups as exemplified in FIGS. 17 and 18 are specifically contemplated including ring-containing substituents for either of both $R_1$ and $R^2$, such as benzoate esters or pyranyl esters, for example, which ring thereof may be unsubstituted or substituted by 1 to 5 lower alkyl, lower alkoxy, hydroxy or halo groups.

Additionally, groups $R_1$ and/or $R_2$ may contain intermittent linking sequences between and heteroatoms and rings. For example $R_1$ and/or $R_2$ may each be, for example, Phenylalanyl-oxo-(CH$_2$)m-(C=O)—O—, Pyranyl-(CH2)m-(C=O)—O—, where m is from 1-20 carbon atoms, preferably 1-10 carbon atoms). In this instance, the group —(CH$_2$)— is a "linker".

Furthermore, compounds containing an amino acid in group $R_1$ and/or $R_2$ are specifically contemplated. For example, the compound at the top of FIG. 19 contains a phenylalanyl group bridged by an oxyethylcarbonyl group to the terminal phenyl hydroxy group of xamoterol. Any amino acid, preferably L-amino acid, may be used in place of phenyl-alanine in such compounds. Amino acids, such as alanine, aspartic acid, isoleucine, threonine and valine may be mentioned, for example.

All of the prodrug compounds of the present invention may be prepared by reference to Schemes 1, 2 or 3 above with any modifications necessary requiring analogy to these schemes. Further, any modifications required may be effected using well-known reactions Range of Amounts of β1-ADR Prodrug Compounds Used Generally, for treating AD, DS or Autism, one or more β1-ADR prodrug compounds are administered in the amount of from about 1 to 20 mg/kg of body weight of the human for clinical use or animal for pre-clinical testing or drug screening. More preferably, from about 2 to 10 mg/kg of body weight for both human and animal are administered. Moreover, the administration may be multiple times at the discretion of the treating physician for humans, and laboratory scientist or veterinarian for animals. As used herein, "about" means±25%. Hence, "about 1" means from 0.75 to 1.25.

As noted above, the β1-ADR prodrugs are administered either by i.v. or s.c. in the form of a solution in a pharmaceutically acceptable solution of sterile saline or dextrose-5%-saline (D5S). However, for β1-ADR prodrugs of very enhanced lipophilicity, i.e., poor water solubility, various known suspensions may be used. See U.S. Pat. No. 5,679,138, which is incorporated herein in the entirety. Other modes of administration, such as oral or intranasal may be used. Oral administration may be effected with suspensions, tablets or capsules. Intranasal administration may be effected using dry powder inhalers, mist inhalers or by drops or swabs using known methodologies.

Testing for Improved Cognition and Social Memory

Testing for improved cognition and social memory in humans having AD, DS, ADD, ADHD and Autism is effected using known diagnostic methodologies, including observation. Testing for mice, for example, may be conducted using known tests as described hereinabove.

For humans with AD, testing may be done using the Folstein test (also known as the mini-mental state examination). This test utilizes a questionnaire to screen for mental impairment and is published by the Psychological Assessment Resources. Categories tested include, for example, orientation of time and place, attention and calculation, recall, language recognition, repetition and ability to obey complex commands. Individuals tested are rated by points given in each category out of a maximum possible number of points for each category.

For humans with DS, testing is usually done with the Arizona Cognitive Test Battery. See J. Neurodev. Disorder 2010 Sep. 1; 2 (3): 149-164.

For humans having autistic spectrum disorders, testing is usually done with the Social Cognitive Skills Test. See J. Intell. Disability 2008 March; 12(1):49-57. It is explicitly recognized herein that the compounds and compositions of the present invention may be advantageously used to treat individuals representing a full range of autistic spectrum disorders.

Synthetic Example

Preparation of Xamoterol Fumarate from U.S. Pat. No. 4,143,140, which is incorporated herein in the entirety.

A suspension of 1-p-benzyloxyphenoxy-2,3-epoxypropane (11.5 g.) in isopropanol (6 ml) is added to a stirred mixture of 4-(N-β-aminoethylcarbamoyl) morpholine hydrogen sulfate (12.7 g.), potassium hydroxide (7.0 g.) and isopropanol (10 ml) and the mixture is stirred at 45° C. for 1 hour and then evaporated to dryness under reduced pressure. The residual oil is stirred with water, and the mixture is filtered and the solid residue is dissolved in acetone. A 30% solution of hydrogen chloride in propanol is added until the pH of the mixture is less than 2, and the mixture is filtered. The solid residue is crystallized from water and there is thus obtained 1-p-benzyloxyphenoxy-3-(β-morpholinocarbonamidoethyl) amino-2-propanol hydrochloride (4.9 g.).

A solution of the above compound in a mixture of ethanol (20 ml) and acetic acid (20 ml) is shaken with a 30% palladium-on-charcoal catalyst (0.1 g.) in an atmosphere of hydrogen at laboratory temperature and pressure until 250 ml of hydrogen is absorbed. The mixture is filtered, the filtrate is evaporated to dryness under reduced pressure and to the residue is added a hot solution of fumaric acid (1.25 g.) in ethanol (15 ml). The mixture is kept at 5° C. for 12 hours and then is filtered, and the solid residue is washed with hot ethanol and then dried. There is thus obtained 1-p-hydroxyphenoxy-3-β-(morpholinocarbonamido) ethylamino-2-propanol hydrogen fumarate, m.p. 168-169° C. (with decomposition).

The 4-(N-β-aminoethylcarbamoyl)morpholine hydrogen sulfate used as a starting material may be obtained as follows:

Morpholine (4.35 g.) and phenyl chloroformate (6.35 g.) are separately and simultaneously added dropwise during 20 min. to a stirred mixture of toluene (10 ml), water (5 ml) and sodium hydroxide (2 g.) which is maintained at 0° C. The mixture is stirred for a further 2 hours while the temperature is allowed to rise to 20° C. The toluene solution is separated, the aqueous solution is extracted twice with toluene and the combined toluene solutions are washed with water, dried and evaporated to dryness under reduced pressure. The residue is crystallized from petroleum ether (b.p. 60-80° C.) and there is obtained N-phenoxycarbonylmorpholine, m.p. 46.5-47.5° C. A mixture of this compound (11 g.) and ethylenediamine (27.8 g.) is stirred at laboratory temperature for 3 days and the excess of ethylenediamine is removed by evaporation under reduced pressure. The residue is dissolved in methanol, the solution is cooled to 5° C. and concentrated sulfuric acid is added until the pH of the solution is 2. A filter-aid (Celite, 10 g.) is added and the mixture is stirred for 1 hour and then filtered. The filtrate is evaporated to dryness under reduced pressure and the residue is stirred with ethyl acetate. The mixture is filtered and there is thus obtained as solid residue 4-(N-β-aminoehtylcarbamoyl)morpoholine hydrogen sulfate, m.p. 168-169° C.

In the above preparation, any organic or inorganic acid may be used instead of fumaric acid in a stoichiometric manner to prepare the corresponding salt of xamoterol.

Having described the present invention, it is understood that many routine changes and modifications may be made to the above-described embodiments without departing from the spirit and the scope of the present invention.

What is claimed is:

1. A β1-ADR agonist prodrug compound, which is hydrolysable in vivo to release a corresponding β1-ADR agonist compound, and which prodrug compound contains at least one group which imparts greater lipophilicity and CNS bioavailability to the prodrug compound relative to the corresponding β1-ADR agonist compound.

2. The prodrug compound of claim 1, which stimulates cAMP pathway more than the β-arrestin pathway.

3. The prodrug compound of claim 1, which stimulates cAMP signaling cascade at least 50% more than the β-arrestin pathway at the same concentrations in the range of $10^{-4}$ to $10^{-10}$ M.

4. The prodrug compound of claim 1, which stimulates β-arrestin at a level of not more than 20% of the level of cAMP signaling pathway.

5. The prodrug compound of claim 1, which has a c log P value >+1.0.

6. The prodrug compound of claim 5, which has a c log P value which is at least +1.50 greater than that of the β1-ADR agonist compound.

7. The prodrug compound of claim 5, which is a xamoterol prodrug.

8. The prodrug compound of claim 7, which is a racemate compound.

9. The prodrug compound of claim 7, which is an (S)-compound.

10. The prodrug of claim 7, which is a (R)-compound.

11. The prodrug compound of claim 1, which further activates a downstream CREB pathway.

12. The prodrug compound of claim 7, wherein the xamoterol prodrug comprises xamoterol with a terminal phenyl hydroxyl group and/or secondary hydroxy group bonded to an acyl, carbamate or oxoazolidinyl group, which acyl, carbamate or oxoazolidinyl groups are hydrolysable in vivo.

13. The prodrug of claim 12, wherein the xamoterol prodrug is an acylated xamoterol having the terminal phenyl hydroxyl and/or secondary hydroxy group thereof being acylated by the groups R1-(C=O)—O— and/or R2-(C=O)—O—, respectively, wherein $R_1$ and $R_2$ may be the same or different and are each a lipophilic group of from 5 to 30 carbon atoms, which is linear, branched or cyclic or a combination thereof, which are unsubstituted or optionally substituted by 1 to 4 lower alkyl, lower alkoxy, hydroxy, amino, carboxy or halo groups, and wherein the cyclic group is a 5- or 6-membered ring that contains 0, 1 or 2 heteroatoms, said heteroatoms being —O— or —N— or both, said cyclic group being saturated or unsaturated.

14. The prodrug of claim 13, wherein said cyclic ring in R1 and/or R2 comprises pyrrole, furan, imidizolidine, imidazole, pyrazole, pyridine or pyran, each of which are unsubstituted or optionally substituted.

15. The prodrug of claim 13, wherein $R_1$ and/$R_2$ contain an amino acid radical.

16. The prodrug of claim 13, wherein said halo is fluoro.

17. A method of treating DS in a human, which entails administering one or more β1-ADR agonist prodrugs of claim 1, in an amount effective to improve cognition, including social memory.

18. The method of claim 17, wherein said β1-ADR agonist prodrug is a xamoterol prodrug.

19. The method of claim 17, wherein the administering is by subcutaneous injection.

20. A method of treating AD in a human, which entails administering one or more β1-ADR agonist prodrugs of claim 1, in an amount effective to improve cognition, including social memory.

21. The method of claim 20, wherein the β1-ADR agonist prodrug is a xamoterol prodrug.

22. The method of claim 20, wherein the administering is by subcutaneous injection.

23. A method of treating ADD or ADHD in a human, which entails administering one or more β1-ADR agonist prodrugs of claim 1, in an amount effective to improve cognition, and reduce hyperactivity.

24. The method of claim 23, wherein the β1-ADR agonist prodrug is a xamoterol prodrug.

25. The method of claim 23, wherein the administering is by subcutaneous injection.

26. A method of treating autism in a human, which entails administering one or more β1-ADR agonist prodrugs of claim 1, in an amount effective to improve cognition, including social memory.

27. The method of claim 26, wherein said β1-ADR agonist prodrug is a xamoterol prodrug.

28. The method of claim 26, wherein the administering is by subcutaneous injection.

29. A method of selecting one or more β1-ADR agonist prodrugs for therapeutic use, which comprises:

a) selecting one or more prodrug compounds having an enhanced c log P value relative to the corresponding β1-ADR agonist compound;

b) subjecting the selected prodrug compounds from step a) to a battery of ADME tests, and determining SPR values for the prodrug compounds.

c) selecting one or more prodrug compounds from step b) and subjecting said prodrug compounds to in vivo biodistribution and pharmacokinetic evaluation;

d) selecting one or more prodrug compounds from step c) for pre-clinical animal model studies; and e) producing a TPP for each compound selected in all of steps a)-d), for further development and therapeutic use.

30. The method of claim 29, wherein the one or more β1-ADR agonist prodrugs selected are xamoterol prodrugs.

31. A pharmaceutical composition, comprising one or more of the β1-ADR agonist prodrugs of claim 1, and a pharmaceutically-acceptable carrier.

32. The pharmaceutical composition of claim 31, which is in a form of an aqueous-based solution.

33. The pharmaceutical composition of claim 31, which is in a form of a suspension.

34. The pharmaceutical composition of claim 31, wherein the β1-ADR agonist prodrug is a xamoterol prodrug.

35. The pharmaceutical composition of claim 34, wherein the xamoterol prodrug is an (R)-enantiomeric prodrug.

36. The pharmaceutical composition of claim 34, wherein the xamoterol prodrug is an (S)-enantiomeric prodrug.

* * * * *